US010092563B2

United States Patent
Cai et al.

(10) Patent No.: US 10,092,563 B2
(45) Date of Patent: Oct. 9, 2018

(54) PHOSPHATIDYLINOSITOL 3-KINASE INHIBITORS

(71) Applicant: Gilead Sciences, Inc., Foster City, CA (US)

(72) Inventors: Shaopei Cai, Seattle, WA (US); Zhimin Du, Belmont, CA (US); Joshua Kaplan, Foster City, CA (US); Jennifer A. Loyer-Drew, Seattle, WA (US); Devan Naduthambi, San Bruno, CA (US); Barton W. Phillips, San Mateo, CA (US); Gary Phillips, Issaquah, WA (US); Joshua Van Veldhuizen, Seattle, WA (US); William J. Watkins, Saratoga, CA (US); Suet Chung Yeung, Redmond, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/735,254

(22) Filed: Jun. 10, 2015

(65) Prior Publication Data
US 2015/0361054 A1 Dec. 17, 2015

Related U.S. Application Data

(60) Provisional application No. 62/012,222, filed on Jun. 13, 2014.

(51) Int. Cl.
| | |
|---|---|
| *A61K 31/496* | (2006.01) |
| *C07D 239/04* | (2006.01) |
| *C07D 239/80* | (2006.01) |
| *C07D 401/14* | (2006.01) |
| *C07D 413/14* | (2006.01) |
| *C07D 407/14* | (2006.01) |
| *C07D 487/04* | (2006.01) |
| *C07D 239/90* | (2006.01) |
| *C07D 471/04* | (2006.01) |
| *C07D 491/048* | (2006.01) |
| *C07D 495/04* | (2006.01) |
| *C07D 513/04* | (2006.01) |
| *C07D 403/14* | (2006.01) |
| *C07D 405/14* | (2006.01) |

(52) U.S. Cl.
CPC .......... *A61K 31/496* (2013.01); *C07D 239/04* (2013.01); *C07D 239/80* (2013.01); *C07D 239/90* (2013.01); *C07D 401/14* (2013.01); *C07D 407/14* (2013.01); *C07D 413/14* (2013.01); *C07D 471/04* (2013.01); *C07D 487/04* (2013.01); *C07D 491/048* (2013.01); *C07D 495/04* (2013.01); *C07D 513/04* (2013.01); *C07D 403/14* (2013.01); *C07D 405/14* (2013.01)

(58) Field of Classification Search
CPC .. A07D 471/04; A61K 31/496; C07D 239/04; C07D 239/80
USPC ........................................... 514/210.21
See application file for complete search history.

(56) References Cited

U.S. PATENT DOCUMENTS

| | | | |
|---|---|---|---|
| 6,518,277 | B1 | 2/2003 | Sadhu et al. |
| 6,667,300 | B2 | 12/2003 | Sadhu et al. |
| 6,800,620 | B2 | 10/2004 | Sadhu et al. |
| 6,949,535 | B2 | 9/2005 | Sadhu et al. |
| 7,932,260 | B2 | 4/2011 | Fowler et al. |
| 8,138,195 | B2 | 3/2012 | Sadhu et al. |
| 8,207,153 | B2 | 6/2012 | Fowler et al. |

(Continued)

FOREIGN PATENT DOCUMENTS

| | | |
|---|---|---|
| CA | 2895782 A1 | 6/2014 |
| CN | 1440408 A | 9/2003 |

(Continued)

OTHER PUBLICATIONS

Intl. Search Report—Written Opinion dated Aug. 26, 2015 for PCT/US2015/035157.

(Continued)

*Primary Examiner* — Craig D Ricci
*Assistant Examiner* — Janet L. Coppins
(74) *Attorney, Agent, or Firm* — Morrison & Foerster LLP

(57) ABSTRACT

The present application provides the compounds of formula (J),

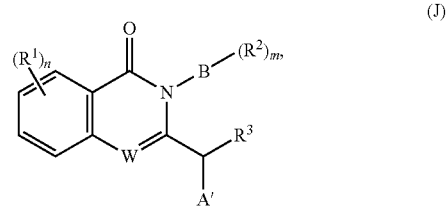

or pharmaceutically acceptable salts, isomers, tautomer, or a mixture thereof, wherein W, B, n, m, A', $R^1$, $R^2$, and $R^3$ are described herein. The compounds are inhibitors to the activities of phosphatidylinositol 3-kinase (PI3K) and are useful for treating conditions mediated by one or more PI3K isoforms. The present application further provides pharmaceutical compositions that include a compound of formula (I), or pharmaceutically acceptable salts, isomers, tautomer, or mixture thereof, and methods of using these compounds and compositions for treating conditions mediated by one or more PI3K isoforms.

11 Claims, No Drawings

(56) References Cited

U.S. PATENT DOCUMENTS

| | | | |
|---|---|---|---|
| 8,435,988 B2 | 5/2013 | Qu et al. | |
| 8,492,389 B2 | 7/2013 | Sadhu et al. | |
| RE44,599 E | 11/2013 | Fowler et al. | |
| 8,586,597 B2 | 11/2013 | Fowler et al. | |
| RE44,638 E | 12/2013 | Fowler et al. | |
| 8,623,881 B2 | 1/2014 | Sadhu et al. | |
| 8,637,533 B2 | 1/2014 | Sadhu et al. | |
| 8,653,077 B2 | 2/2014 | Sadhu et al. | |
| 8,673,906 B2 | 3/2014 | Barlaam et al. | |
| 8,779,131 B2 | 7/2014 | Kesicki et al. | |
| 8,980,901 B2 | 3/2015 | Fowler et al. | |
| 8,993,583 B2 | 3/2015 | Fowler et al. | |
| 9,029,384 B2 | 5/2015 | Evarts et al. | |
| 9,149,477 B2 | 10/2015 | Kesicki et al. | |
| 9,221,795 B2 | 12/2015 | Evarts et al. | |
| 9,266,878 B2* | 2/2016 | Evarts | C07D 471/08 |
| 9,487,772 B2 | 11/2016 | Sadhu et al. | |
| 9,499,523 B2 | 11/2016 | Kim et al. | |
| 9,676,759 B2 | 6/2017 | Aronov et al. | |
| 9,765,060 B2 | 9/2017 | Kaplan et al. | |
| 2002/0161014 A1 | 10/2002 | Sadhu et al. | |
| 2004/0266780 A1 | 12/2004 | Sadhu et al. | |
| 2008/0287469 A1 | 11/2008 | Diacovo et al. | |
| 2009/0312319 A1 | 12/2009 | Ren et al. | |
| 2010/0256167 A1 | 10/2010 | Fowler et al. | |
| 2012/0015964 A1 | 1/2012 | Fowler et al. | |
| 2013/0053362 A1 | 2/2013 | Castro et al. | |
| 2013/0274253 A1 | 10/2013 | Brollo et al. | |
| 2014/0179673 A1* | 6/2014 | Evarts | C07D 471/08 514/210.21 |
| 2015/0361095 A1 | 2/2015 | Evarts et al. | |
| 2015/0087663 A1 | 3/2015 | Xi et al. | |
| 2015/0361054 A1 | 12/2015 | Cai et al. | |
| 2015/0361068 A1 | 12/2015 | Evarts et al. | |
| 2015/0361070 A1 | 12/2015 | Evans et al. | |
| 2016/0075705 A1 | 3/2016 | Kesicki et al. | |
| 2017/0049772 A1 | 2/2017 | Sadhu et al. | |
| 2017/0340633 A1 | 11/2017 | Sadhu et al. | |
| 2018/0065953 A1 | 3/2018 | Evarts et al. | |

FOREIGN PATENT DOCUMENTS

| | | |
|---|---|---|
| CN | 101031569 A | 9/2007 |
| JP | 2003-512461 A | 4/2003 |
| JP | 2005-509635 A | 4/2005 |
| JP | 2007-537291 A | 12/2007 |
| JP | 2013-515074 A | 5/2013 |
| JP | 2013-526586 A | 6/2013 |
| JP | 2013-540746 A | 11/2013 |
| JP | 2016-503805 A | 2/2016 |
| JP | 2016-527238 A | 9/2016 |
| JP | 6125663 B2 | 5/2017 |
| JP | 2017-517527 A | 6/2017 |
| JP | 6207100 B2 | 10/2017 |
| WO | WO-2001/30768 A1 | 5/2001 |
| WO | WO-2001/081346 A2 | 11/2001 |
| WO | WO-2003/035075 A1 | 5/2003 |
| WO | WO-2005/113556 A1 | 12/2005 |
| WO | WO-2006/089106 A2 | 8/2006 |
| WO | WO-2009-088986 A1 | 7/2009 |
| WO | WO-2011/146882 A1 | 11/2011 |
| WO | WO-2012/037204 A1 | 3/2012 |
| WO | WO-2013/032591 A1 | 3/2013 |
| WO | WO-2014/023083 A1 | 2/2014 |
| WO | WO-2014/100767 A1 | 6/2014 |
| WO | WO-2014100765 A1 | 6/2014 |
| WO | WO-2014/128612 A1 | 8/2014 |
| WO | WO-2015/010641 A1 | 1/2015 |
| WO | WO-2015/051241 A1 | 4/2015 |
| WO | WO-2015/081127 A1 | 6/2015 |
| WO | WO-2015/168079 A1 | 11/2015 |
| WO | WO-2015/191726 A1 | 12/2015 |
| WO | WO-2015/191743 A1 | 12/2015 |
| WO | WO-2015/191745 A1 | 12/2015 |
| WO | WO-2015/191752 A1 | 12/2015 |
| WO | WO-2015/191754 A2 | 12/2015 |

OTHER PUBLICATIONS

Office Action dated Apr. 13, 2017 for Australian Appl. No. 2015274635.
Office Action dated Apr. 19, 2017 for New Zealand Appl. No. 726608.
Foreign Office Action dated Sep. 26, 2017 for Eurasian Patent Application No. 201692249, filed on Dec. 6, 2016, 8 pages.
Foreign Office Action dated Sep. 26, 2017 for European Patent Application No. 15739040.2, filed on Dec. 22, 2016, 2 pages.
U.S. Appl. No. 15/680,045, filed Aug. 17, 2017, by Evarts et al.
Chemical Encyclopedia (1988), publisher "Soviet encyclopedia", Moscow, 2:365-369.
Engelman, et al. (Aug. 2009). "Targeting PI3K Signaling in Cancer: Opportunities, Challenges and Limitations", *Nat. Rev. Cancer* 9:550-562.
Foster, A. (Dec. 1984). "Deuterium Isotope Effects in Studies of Drug Metabolism", *Trends Pharmacol. Sci.* 5(12):524-527.
Hiles, I.D. et al. (Aug. 7, 1992). "Phosphatidylinositol 3-kinase: Structure and Expression of the 110 kd Catalytic Subunit," *Cell* 70(3):419-429.
International Preliminary Report dated Dec. 12, 2016, for PCT Patent Application No. PCT/US2015/035157, filed Jun. 10, 2015, 8 pages.
J.G. Cannon, Chapter Nineteen in Burger's Medicinal Chemistry and Drug Discovery, Fifth Edition, vol. I: Principles and Practice, Wiley-Interscience 1995, pp. 783-802 (Year 1995).
McMahon, G. (2000). "VEGF Receptor Signaling the Tumor Angiogenisis," *The Oncologist* 5(Suppl. 1):3-10.
Notice of Acceptance dated Apr. 10, 2018, for Australian Patent Application No. 2015274635, filed Jun. 10, 2015, 3 pages.
Notice of Acceptance dated Apr. 12, 2018, for New Zealand Patent Application No. 2015274635, filed Jun. 10, 2015, 3 pages.
Office Action dated Apr. 19, 2017, for New Zealand Patent Application No. 726608, filed Nov. 21, 2016, 4 pages.
Office Action dated Apr. 7, 2017, for Australian Patent Application No. 2015274637, filed Jun. 10, 2015, 4 pages.
Office Action dated Feb. 27, 2018, for European Patent Application No. 15739040.2, filed Dec. 22, 2016, 5 pages.
Office Action dated Feb. 6, 2018, for Israel Patent Application No. 249078, 5 pages. (including English translation).
Office Action dated Mar. 13, 2018, for New Zealand Patent Application No. 726608, filed Jun. 10, 2015, 2 pages.
Office Action dated Nov. 13, 2017, for New Zealand Patent Application No. 726608, filed Jun. 10, 2015, 4 pages.
Office Action dated Nov. 20, 2017, for Japanese Patent Application No. 2016-572428, filed Jun. 10, 2015, 13, pages. (including English translation).
Office Action dated Nov. 29, 2017, for Canadian Patent Application No. 2,952,037, filed Jun. 10, 2015, 5 pages.
Otsu, M. et al. (Apr. 5, 1991). "Characterization of Two 85 kd Proteins that Associate with Receptor Tyrosine Kinases, Middle-T/pp60c-src Complexes, and P13-Kinase," *Cell* 65:91-104.
Panayotou, G. et al. (Dec. 1992). "Phosphatidyl-Inositol 3-Kinase: A Key Enzyme in Diverse Signaling Processes," *Trends in Cell Biol.* 2:358-360.
Pinedo, H.M. et al. (2000). "Translational Research: The Role of VEGF in Tumor Angiogenesis," *The Oncologist* 5(Suppl. 1):1-2.
Rameh, L.E. et al. (Mar. 26, 1999). "The Role of Phosphoinositide 3-Kinase Lipid Products in Cell Function," *J. Biol. Chem.* 274(13):8347-8350.
Office Action dated May 17, 2018, for Korean Patent Application No. 10-2017-7000691, filed on Jan. 10, 2017, 20 pages. (including English translation).
Office Action dated Jun. 4, 2018, for Eurasian Patent Application No. 201692249, filed Jun. 10, 2015, 5 pages. (including English translation).

\* cited by examiner

PHOSPHATIDYLINOSITOL 3-KINASE INHIBITORS

CROSS REFERENCE TO RELATED APPLICATIONS

This application claims priority to and the benefit under 35 U.S.C. 119(e) of U.S. Provisional Patent Application Ser. No. 62/012,222, filed Jun. 13, 2014, the disclosure of which is hereby incorporated by reference in its entirety.

FIELD

The present application relates to novel compounds that selectively inhibit the activities of PI3K isoforms and their uses in therapeutic treatments.

BACKGROUND

Cell signaling via 3'-phosphorylated phosphoinositides has been implicated in a variety of cellular processes, e.g., malignant transformation, growth factor signaling, inflammation, and immunity (Rameh et al., *J. Biol. Chem.*, 274: 8347-8350, 1999). Phosphatidylinositol 3-kinase (PI 3-kinase or PI3K) is responsible for generating these phosphorylated signaling products. PI3K was initially identified as a protein associated with viral oncoproteins and growth factor receptor tyrosine kinases that phosphorylate phosphatidylinositol (PI) and its phosphorylated derivatives at the 3'-hydroxyl of the inositol ring (Panayotou et al., *Trends Cell Biol.*, 2:358-60, 1992).

Three classes of the PI 3-kinase (PI3K) are proposed based on the substrate specificities. Class I PI3Ks phosphorylate phosphatidylinositol (PI), phosphatidylinositol-4-phosphate, and phosphatidylinositol-4,5-biphosphate ($PIP_2$) to produce phosphatidylinositol-3-phosphate (PIP), phosphatidylinositol-3,4-biphosphate, and phosphatidylinositol-3,4,5-triphosphate, respectively. Also, Class II PI3Ks phosphorylate PI and phosphatidylinositol-4-phosphate, and Class III PI3Ks phosphorylate PI.

The initial purification and molecular cloning of PI 3-kinase revealed that it was a heterodimer consisting of p85 and p110 subunits (Otsu et al., *Cell*, 65:91-104, 1991; Hiles et al., *Cell*, 70:419-29, 1992). Later, four distinct Class I PI3Ks were identified and designated as PI3Kα, β, δ, and γ isoforms. Each isoform consists of a distinct 110 kDa catalytic subunit and a regulatory subunit. The catalytic subunits of PI3Kα, β, and δ (i.e., p110α, p110β, and p110δ, respectively) interacts, individually, with the same regulatory subunit p85, whereas the catalytic subunit of PI3Kγ (p110γ) interacts with a distinct regulatory subunit p101.

Studies have also showed that each PI3K isoform has distinct expression pattern. For example, PIK3CA which encodes PI3Kα is frequently mutated in human cancers (Engelman, *Nat. Rev. Cancer*, 9: 550-562, 2009). Also, PI3Kδ is generally expressed in hematopoietic cells. Moreover, PI3K isoforms are shown to be associated with proliferation or survival signaling in cancers, inflammatory, or autoimmune diseases. As each PI3K isoform has different biological function, PI3K isoforms are potential targets to treat cancer or disorder (U.S. Pat. Nos. 6,800,620; 8,435,988; 8,673,906; US Patent Application Publication No. US2013/0274253).

Therefore, there is a need for developing therapeutic agents that inhibit PI3K isoforms to treat diseases, disorders, or conditions that are mediated by PI3K.

SUMMARY

The present application provides novel compounds that are inhibitors of PI3K isoforms. The application also provides compositions, including pharmaceutical compositions, kits that include the compounds, and methods of using and making the compounds. The compounds provided herein are useful in treating diseases, disorders, or conditions that are mediated by PI3K isoforms. The application also provides compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition that is mediated by PI3K isoforms.

The applications provides the compounds having the structure of formula (I):

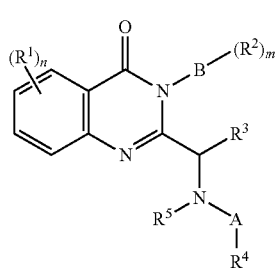

wherein
n is 0, 1, 2, or 3;
m is 0, 1, or 2;
A is a single bond or C(O);
B is three- to ten-membered heterocycloalkyl having at least one heteroatom selected from N or O, wherein heterocycloalkyl is optionally substituted with halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl;
each $R^1$ is independently selected from halo, cyano, optionally substituted $C_{1-6}$ alkyl, optionally substituted $C_{1-6}$ haloalkyl, optionally substituted $C_{1-6}$ alkoxy, optionally substituted sulfonyl, optionally substituted $C_{3-8}$ aryl, optionally substituted $C_{3-8}$ heteroaryl, optionally substituted $C_{3-8}$ cycloalkyl, and optionally substituted $C_{3-8}$ heterocycloalkyl;
each $R^2$ is independently hydrogen, halo, —$NH_2$, optionally substituted $C_{1-6}$ alkyl, and optionally substituted $C_{1-6}$ haloalkyl;
$R^3$ is hydrogen, optionally substituted $C_{1-6}$ alkyl, $C_{3-8}$ cycloalkyl, or $C_{6-10}$ aryl;
$R^4$ is a six- to twelve-membered heteroaryl having at least one aromatic group and at least two heteroatoms selected from N, O, or S, wherein the heteroaryl is optionally substituted with one, two, or three members independently selected from halo, cyano, optionally substituted $C_{1-6}$ haloalkyl, optionally substituted $C_{1-6}$ alkyl, optionally substituted $C_{2-4}$ alkynyl, and —$NH_2$; and
$R^5$ is hydrogen or optionally substituted $C_{1-6}$ alkyl, wherein $R^5$ and $R^3$ together with the atoms to which they are attached optionally form a four- to eight-membered heterocyclic ring;
or a pharmaceutically acceptable salt, isomer, or a mixture thereof.

The application also provide the compound having the structure of formula (I), wherein:

B is a four- to eight-membered heterocycloalkyl having at least one heteroatom selected from N or O, wherein the heterocycloalkyl moiety is optionally substituted with halo, $C_{1-6}$ alkyl, $C_{3-8}$ heterocycloalkyl, $C_{1-6}$ haloalkyl, and $C_{3-8}$ cycloalkyl, wherein each of the $C_{1-6}$ alkyl moiety is optionally substituted with $C_{6-10}$ aryl, $C_{1-6}$ alkoxy, wherein $C_{6-10}$ aryl is optionally substituted with one or two members independently selected from halo, $C_{1-6}$ alkyl, $C_{1-6}$ haloalkyl, $C_{3-8}$ heterocycloalkyl, $C_{3-8}$ cycloalkyl moiety, wherein $C_{3-8}$ heterocycloalkyl is optionally substituted with $C_{1-6}$ alkyl;

n is 1 or 2;

m is 0, 1, or 2;

each $R^1$ is independently selected from halo, $C_{1-6}$ alkyl, and $C_{1-6}$ haloalkyl;

each $R^2$ is independently selected from halo, $-NH_2$, $C_{1-6}$ alkyl, and $C_{1-6}$ haloalkyl;

$R^3$ is hydrogen, $C_{1-6}$ alkyl, $C_{3-8}$ cycloalkyl, or $C_{6-10}$ aryl;

$R^4$ is a six- to twelve-membered heteroaryl having at least one aromatic ring and at least two nitrogen atoms, wherein the heteroaryl is optionally substituted with one, two, or three members independently selected from halo, cyano, $-NH_2$, $C_{1-6}$ haloalkyl, $C_{1-6}$ alkyl, and $C_{2-4}$ alkynyl wherein the alkynyl moiety is optionally substituted with $C_{6-10}$ aryl or $C_{6-10}$ heteroaryl, each of which is optionally substituted with one, two, or three members independently selected from halo, $C_{1-6}$ alkyl, and $C_{1-6}$ haloalkyl; and $R^5$ is hydrogen, methyl, ethyl, or propyl, wherein $R^3$, $R^5$ and the atoms they attached to may optionally form a five-membered heterocyclic group;

or a pharmaceutically acceptable salt, isomer, or a mixture thereof.

In one aspect, the compounds have the structure of formula (I) wherein each $R^1$ is selected from chloro, bromo, fluoro, methyl, ethyl, and propyl. In other aspect, the compounds have the structure of formula (I) wherein each $R^2$ is selected from fluoro, chloro, bromo, $-NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, fluoropropyl. In some aspect, the compounds have the structure of formula (I) wherein $R^3$ is selected from hydrogen, methyl, ethyl, propyl, butyl, cyclopropyl, or cyclobutyl. In certain aspect, the compounds have the structure of formula (I) wherein $R^5$ is selected from hydrogen, methyl, ethyl, or propyl. In other aspect, the compounds have the structure of formula (I) wherein $R^3$ and $R^5$ together with the atoms to which they are attached optionally form pyrrolidinyl. In some other aspect, the compounds have the structure of formula (I) wherein $R^4$ is a heteroaryl having at least one aromatic ring and at least two nitrogen atoms, wherein $R^4$ is optionally substituted with two or three members independently selected from the group consisting of halo, cyano, $-NH_2$, $C_{1-4}$ alkyl, and $C_{2-4}$ alkynyl which is substituted with $C_{6-10}$ aryl or $C_{3-8}$ heteroaryl, each of which is optionally substituted with one member of halo or $C_{1-4}$ haloalkyl. In yet other aspect, the compounds have the structure of formula (I) wherein $R^4$ is a pyrimidinyl or pyrazinyl; wherein each of the pyrimidinyl or pyrazinyl moieties is optionally substituted with two or three members independently selected from bromo, chloro, fluoro, cyano, methyl, ethyl, propyl, $-NH_2$, and $C_{2-4}$ alkynyl, wherein the $C_{2-4}$ alkynyl moiety is substituted with pyridinyl, phenyl, pyrazolyl, pyrazinyl, and pyrimidinyl, where each of the pyridinyl, phenyl, pyrazolyl, pyrazinyl, and pyrimidinyl moieties is optionally substituted with one or two members independently selected from fluoro, chloro, bromo, iodo, fluoromethyl, difluoromethyl, trifluoromethyl, fluoroethyl, difluoroethyl, trifluoroethyl, fluoropropyl, difluoropropyl, and trifluoropropyl. In further aspect, the compounds have the structure of formula (I), wherein $R^4$ is selected from purinyl, thiazolopyrimidinyl, pyridopyrimidinyl, thienopyrimidinyl, pyrrolopyrimidinyl, furopyrimidinyl, or imidazotriazinyl; wherein each of the purinyl, thiazolopyrimidinyl, pyridopyrimidinyl, thienopyrimidinyl, pyrrolopyrimidinyl, furopyrimidinyl, or imidazotriazinyl moieties is optionally substituted with one or two members independently selected from bromo, chloro, fluoro, methyl, ethyl, propyl, and $-NH_2$. In some further aspect, the compounds have the structure of formula (I) wherein B is a six- to eight-membered fused-heterocycloalkyl, bridged-heterocycloalkyl, or spiro-heterocycloalkyl, wherein each of fused-heterocycloalkyl, bridged-heterocycloalkyl, or spiro-heterocycloalkyl is optionally substituted with one or two members independently selected from halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl. In certain further aspect, the compounds have the structure of formula (I) wherein B is azepanyl, diazepanyl, pyrrolidinyl, tetrahydrofuranyl, oxetanyl, piperidinyl, or piperazinyl; each of the azepanyl, diazepanyl, pyrrolidinyl, tetrahydrofuranyl, oxetanyl, piperidinyl, and piperazinyl moieties is optionally substituted with one or two members independently selected from halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl.

In certain embodiments, the PI3K inhibitors are the compounds selected from Table 1, a pharmaceutically acceptable salt, isomer, or a mixture thereof. In certain embodiments, the PI3K inhibitors are the compounds selected from Table 1a, a pharmaceutically acceptable salt, isomer, or a mixture thereof. In additional embodiments, the compound is an (S)-enantiomer. In other embodiments, the compound is an (R)-enantiomer. In other additional embodiments, the compound is an atropisomer.

The application also provides a pharmaceutical composition that comprises a compound of formula (I), a pharmaceutically acceptable salt, isomer, or a mixture thereof, together with at least one pharmaceutically acceptable vehicle. Examples of a pharmaceutically acceptable vehicle may be selected from carriers, adjuvants, and excipients.

Further provided herein is a method of treating a disease, disorder, or condition in a human in need thereof by administering to the human a therapeutically effective amount of a compound of formula (I) or a pharmaceutically acceptable salt, isomer, or a mixture thereof. Further provided is a compound of formula (I) for use in a method of treating a disease, disorder or condition that is mediated by PI3K isoforms. The application also provides the use of a compound of formula (I) in the manufacture of a medicament for the treatment of a disease, disorder or condition that is mediated by PI3K isoforms. In certain embodiments, the disease, disorder, or condition is associated or mediated by PI3K. In some embodiments, the disease, disorder, or condition is an inflammatory disorder. In other embodiments, the disease, disorder, or condition is a cancer.

Also provided herein is a method of inhibiting the activity of a phosphatidylinositol 3-kinase polypeptide by contacting the polypeptide with a compound of formula (I) or a pharmaceutically acceptable salt, isomer, or a mixture thereof.

Further provided is a method of inhibiting excessive or destructive immune reactions, comprising administering an effective amount of a compound of formula (I) or a pharmaceutically acceptable salt, isomer, or a mixture thereof.

Also provided is a method of inhibiting growth or proliferation of cancer cells comprising contacting the cancer cells with an effective amount of a compound of formula (I) or a pharmaceutically acceptable salt, isomer, or a mixture thereof.

Also provided is a kit that includes a compound of formula (I) or a pharmaceutically acceptable salt, isomer, or a mixture thereof. The kit may further comprise a label and/or instructions for use of the compound in treating a disease, disorder, or condition in a human in need thereof. In some embodiments, the disease, disorder, or condition may be associated or mediated by PI3K activity.

Also provided are articles of manufacture that include a compound of formula (I) or a pharmaceutically acceptable salt, isomer, or a mixture thereof, and a container. In one embodiment, the container may be a vial, jar, ampoule, preloaded syringe, or an intravenous bag.

DETAILED DESCRIPTION

The following description sets forth exemplary methods, parameters and the like. Such description is not intended as a limitation on the scope of the present application but is instead provided as exemplary embodiments.

As used herein, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e. $C_{1-6}$ alkyl), or 1 to 4 carbon atoms (i.e., $C_{1-4}$ alkyl). Examples of alkyl, groups include methyl, ethyl, propyl, isopropyl, n-butyl, sec-butyl, iso-butyl, tert-butyl, pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" includes n-butyl, sec-butyl, isobutyl and t-butyl; "propyl" includes n-propyl and isopropyl.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., C2-4 alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one alkenyl). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocycloalkyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. The term "heterocycloalkyl" includes heterocycloalken groups (i.e. the heterocycloalkyl group having at least one alkenyl). A heterocycloalkyl may be a single ring or multiple rings wherein the multiple rings may be fused, bridged, or spirt). As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocycloalkyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl. As used herein, the term "bridged-heterocycloalkyl" refers to a four- to ten-membered heterocycloalkyl connected at two non-adjacent atoms of the heterocycloalkyl with one or more (e.g. 1 or 2) four- to ten-membered heterocycloalkyl. Examples of the bridged-heterocycloalkyl include bicyclic and tricyclic ring systems, such as 8-azabicyclo[3.2.1]octane, 7-azabicyclo[2.2.1]heptane, and, 2-azabicyclo[2.2.1]heptane]. Also used herein, the term "spiro-heterocycloalkyl" refers to a ring system in which a three- to ten-membered heterocycloalkyl has one or more additional ring, wherein the one or more additional ring is three- to ten-membered cycloalkyl or three- to ten-membered heterocycloalkyl, where a single atom of the one or more additional ring is also an atom of the three- to ten-membered heterocycloalkyl. Examples of the spiro-heterocycloalkyl include bicyclic and tricyclic ring systems, such as 4,7-diazaspiro[2.5]octane, 2-azaspiro[3.3]heptane, and 2',3',5',6'-tetrahydrospiro[indoline-3,4'-pyran].

"Hydroxy" or "hydroxyl" refers to the group —OH.

"Oxo" refers to the group (=O) or (O).

"Sulfonyl" refers to the group —S(O)$_2$R, where R is alkyl, haloalkyl, cycloalkyl, heterocycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. By way of example, there may be one, two, three, four, five, or six substitutents. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocycloalkyl, aryl, and heteroaryl. In additional embodiments, "substituted cycloalkyl" refers to a cycloalkyl group having one or more substituents including alkyl, haloalkyl, heterocycloalkyl, aryl, heteroaryl, alkoxy, halo, hydroxyl; "substituted aryl" refers to an aryl group having one or more substituents including halo, alkyl, haloalkyl, heterocycloalkyl, heteroaryl, alkoxy, and cyano, and "substituted sulfonyl" refers to a group —S(O)$_2$R, in which R is substituted with alkyl, cycloalkyl, heterocycloalkyl, aryl or heteroaryl. In other embodiments, the one or more substituents may be further substituted with halo, alkyl, haloalkyl, alkoxy, cycloalkyl, heterocycloalkyl, aryl, or heteroaryl, each of which is substituted. In other embodiments, the substituents may be further substituted with halo, alkyl, haloalkyl, alkoxy, cycloalkyl, heterocycloalkyl, aryl, or heteroaryl, each of which is unsubstituted.

PI3K Inhibitor Compounds

The present application provides the compounds that function as inhibitors of PI3K isoforms. In one aspect, the PI3K inhibitors are the compounds having the structure of formula (1):

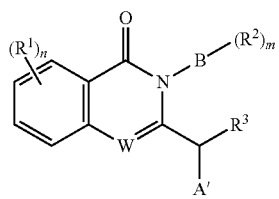

(J)

wherein:

n is 0, 1, 2, 3, or 4;

m is 0, 1, 2, or 3;

W is CH or N;

A' is a OR$^4$, N(R$^5$)C(O)R$^4$, or NR$^5$R$^4$;

B is optionally substituted heterocycloalkyl;

each R$^1$ is independently selected from halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, optionally substituted heterocycloalkyl;

each R$^2$ is independently selected from halo, optionally substituted alkyl, optionally optionally substituted haloalkyl, and —NH$_2$;

R$^3$ is hydrogen, optionally substituted alkyl, optionally substituted haloalkyl, optionally substituted cycloalkyl, or optionally substituted aryl;

R$^4$ is heteroaryl optionally substituted with one, two, or three members independently selected from halo, cyano, optionally substituted haloalkyl, optionally substituted alkyl, optionally substituted alkynyl, and —NH$_2$; and R$^5$ is hydrogen or optionally substituted alkyl, wherein R$^5$ and R$^3$ together with the atoms to which they are attached optionally form a heterocyclic ring;

or a pharmaceutically acceptable salt, isomer, or a mixture thereof.

In another aspect, the PI3K inhibitors are the compound having the structure of formula (I)

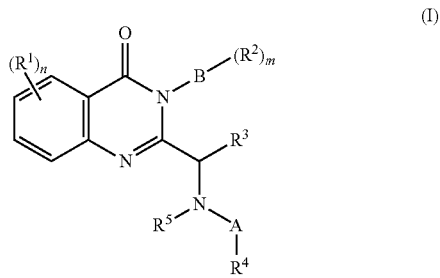

(I)

wherein n is 0, 1, 2, or 3;

m is 0, 1, or 2;

A is a single bond or C(O);

B is three- to ten-membered heterocycloalkyl having at least one heteroatom selected from N or O, wherein heterocycloalkyl is optionally substituted with halo, optionally substituted C$_{1-6}$ alkyl, optionally substituted C$_{3-8}$ heterocycloalkyl, C$_{1-6}$ haloalkyl, and optionally substituted C$_{3-8}$ cycloalkyl;

each R$^1$ is independently selected from halo, cyano, optionally substituted C$_{1-6}$ alkyl, optionally substituted C$_{1-6}$ haloalkyl, optionally substituted C$_{1-6}$ alkoxy, optionally substituted sulfonyl, optionally substituted C$_{3-8}$ aryl, optionally substituted C$_{3-8}$ heteroaryl, optionally substituted C$_{3-8}$ cycloalkyl, and optionally substituted C$_{3-8}$ heterocycloalkyl;

each R$^2$ is independently halo, optionally substituted C$_{1-6}$ alkyl, C$_{1-6}$ haloalkyl, and —NH$_2$;

R$^3$ is hydrogen, optionally substituted C$_{1-6}$ alkyl, C$_{3-8}$ cycloalkyl, or C$_{6-10}$ aryl;

R$^4$ is a six- to twelve-membered heteroaryl having at least one aromatic group and at least two heteroatoms selected from N, O, or S, wherein the heteroaryl is optionally substituted with one, two, or three members independently selected from halo, cyano, optionally substituted C$_{1-6}$ haloalkyl, optionally substituted C$_{1-6}$ alkyl, optionally substituted C$_{2-4}$ alkynyl, and —NH$_2$; and R$^5$ is hydrogen or optionally substituted C$_{1-6}$ alkyl, wherein R$^5$ and R$^3$ together with the atoms to which they are attached optionally form a four- to eight-membered heterocyclic ring;

or a pharmaceutically acceptable salt, isomer, or a mixture thereof.

In other aspect, the compounds having the structure of formula (I), wherein

B is a four- to eight-membered heterocycloalkyl having at least one heteroatom selected from N or O, wherein heterocycloalkyl is optionally substituted with halo, C$_{1-6}$ alkyl, C$_{3-8}$ heterocycloalkyl, C$_{1-6}$ haloalkyl, and C$_{3-8}$ cycloalkyl, wherein each of the C$_{1-6}$ alkyl moiety is optionally substituted with C$_{6-10}$ aryl, C$_{1-6}$ alkoxy, wherein C$_{6-10}$ aryl is optionally substituted with one or two members independently selected from halo, C$_{1-6}$ alkyl, C$_{1-6}$ haloalkyl, C$_{3-8}$ heterocycloalkyl, C$_{3-8}$ cycloalkyl moiety, wherein C$_{3-8}$ heterocycloalkyl is optionally substituted with C$_{1-6}$ alkyl;

n is 1 or 2;

m is 0, 1, or 2;

each R$^1$ is independently selected from halo, C$_{1-6}$ alkyl, and C$_{1-6}$ haloalkyl;

each R$^2$ is independently selected from halo, —NH$_2$, C$_{1-6}$ alkyl, and C$_{1-6}$ haloalkyl;

R$^3$ is hydrogen, C$_{1-6}$ alkyl, C$_{3-8}$ cycloalkyl, or C$_{6-10}$ aryl;

R$^4$ is a six- to twelve-membered heteroaryl having at least one aromatic ring and at least two nitrogen atoms, wherein the heteroaryl is optionally substituted with one, two, or three members independently selected from halo, cyano, —$NH_2$, $C_{1-6}$ haloalkyl, $C_{1-6}$ alkyl, and $C_{2-4}$ alkynyl, wherein the alkynyl moiety is optionally substituted with $C_{6-10}$ aryl or $C_{6-10}$ heteroaryl, each of which is optionally substituted with one, two, or three members independently selected from halo, $C_{1-6}$ alkyl, and $C_{1-6}$ haloalkyl; and $R^5$ is hydrogen, methyl, ethyl, or propyl, wherein $R^3$, $R^5$ and the atoms they attached to may optionally form a five-membered heterocyclic group;

or a pharmaceutically acceptable salt, isomer, or a mixture thereof.

In some aspect, the compound having the structure of the formula (I) wherein:

B is a four- to eight-membered heterocycloalkyl having at least one nitrogen atom, wherein heterocycloalkyl is optionally substituted with halo, methyl, ethyl, propyl, butyl, oxetanyl, fluoromethyl, difluoromethyl, trifluoromethyl, fluoroethyl, difluoroethyl, trifluoroethyl, cyclopropyl, cyclobutyl, and piperidinyl, wherein each of methyl, ethyl, propyl is optionally substituted with phenyl, methoxy, ethoxy, butoxy, wherein phenyl is optionally substituted with fluoro, chloro, methyl, ethyl, propyl, fluoromethyl, difluoromethyl, trifluoromethyl, fluoroethyl, difluoroethyl, trifluoroethyl, methoxy, ethoxy, butoxy, and wherein piperidinyl is optionally substituted with methyl, ethyl, or propyl;

n is 1 or 2;

each $R^1$ is independently selected from chloro, bromo, fluoro, methyl, ethyl, and propyl;

each $R^2$ is independently selected from —$NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl;

$R^3$ is hydrogen, methyl, ethyl, propyl, butyl, cyclopropyl, or cyclobutyl;

$R^4$ is a six- to twelve-membered heteroaryl having at least one aromatic ring and at least two nitrogen atoms, wherein the heteroaryl is optionally substituted with one, two, or three members independently selected from bromo, chloro, fluoro, cyano, methyl, ethyl, propyl, —$NH_2$, and the $C_{2-4}$ alkynyl moiety substituted with pyridinyl, phenyl, pyrazolyl, pyrazinyl, and pyrimidinyl, where each of the pyridinyl, phenyl, pyrazolyl, pyrazinyl, and pyrimidinyl moiety is optionally substituted with fluoro, chloro, bromo, iodo, fluoromethyl, difluoromethyl, trifluoromethyl, fluoroethyl, difluoroethyl, trifluoroethyl, fluoropropyl, difluoropropyl, or trifluoropropyl; and $R^5$ is hydrogen, wherein $R^5$ and $R^3$ together with the atoms to which they are attached optionally form pyrrolidinyl.

The compounds of formulae (J) or (I) may have the structure of formula (II):

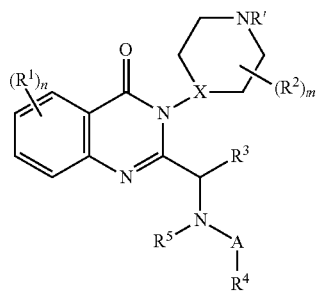

(II)

wherein n, m, A, $R^1$, $R^2$, $R^3$, $R^4$, and $R^5$ are described herein;

X is CH or N;

R' is hydrogen, optionally substituted alkyl, optionally substituted heterocycloalkyl, optionally substituted aryl, optionally substituted haloalkyl, or optionally substituted cycloalkyl;

or a pharmaceutically acceptable salt, isomer, or a mixture thereof.

The compounds of formulae (J) or (I) may have the structure of formula (IIa):

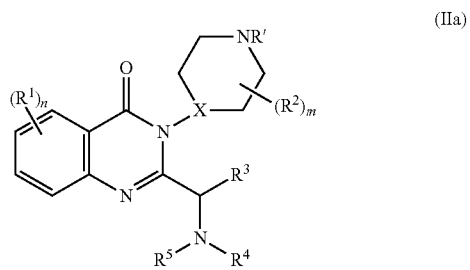

(IIa)

wherein n, m, X, R', $R^1$, $R^2$, $R^3$, $R^4$, and $R^5$ are described herein;

or a pharmaceutically acceptable salt, isomer, or a mixture thereof.

The compound of formulae (J) or (I) may also have the structure of formula (IIb):

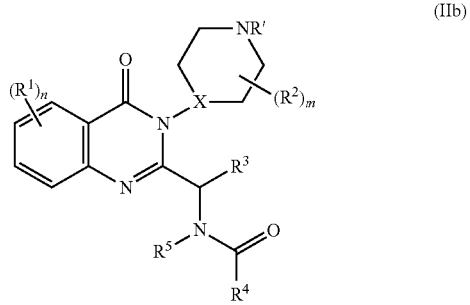

(IIb)

wherein n, m, X, R', $R^1$, $R^2$, $R^3$, $R^4$, and $R^5$ are described herein;

or a pharmaceutically acceptable salt, isomer, or a mixture thereof.

The compounds of formulae (J) or (I) may have the structure of formula (IIc):

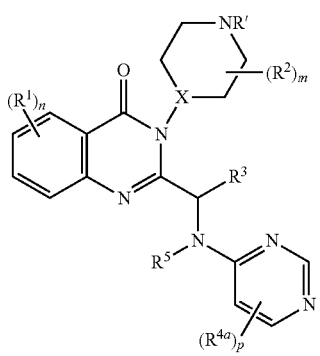

(IIc)

wherein n, m, X, R', $R^1$, $R^2$, $R^3$, and $R^5$ are described herein;

p is 0, 1, 2, or 3;

each $R^{4a}$ is independently selected from halo, cyano, optionally substituted $C_{1-6}$ alkyl, optionally substituted $C_{2-4}$ alkynyl, or —$NH_2$;

or a pharmaceutically acceptable salt, isomer, or a mixture thereof.

The compounds of formulae (J) or (I) may have the structure of formula (IId):

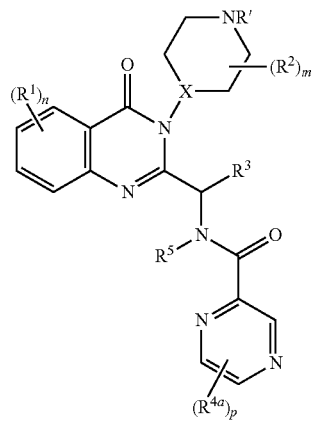

(IId)

wherein n, m, p, X, R', $R^1$, $R^2$, $R^3$, $R^{4a}$, and $R^5$ are described herein;

or a pharmaceutically acceptable salt, isomer, or a mixture thereof.

The compounds of formulae (J) or (I) may have the structure of formula (III):

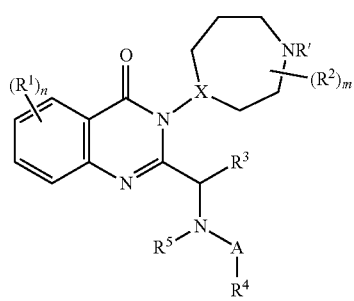

(III)

wherein n, m, A, X, R', $R^1$, $R^2$, $R^3$, $R^4$, and $R^5$ are described herein;

or a pharmaceutically acceptable salt, isomer, or a mixture thereof.

In some embodiments, the compounds have the structure of formula (III), wherein, B is a four- to eight-membered heterocycloalkyl having at least one nitrogen atom, wherein heterocycloalkyl is optionally substituted with halo, methyl, ethyl, propyl, butyl, oxetanyl, fluoromethyl, difluoromethyl, trifluoromethyl, fluoroethyl, difluoroethyl, trifluoroethyl, cyclopropyl, cyclobutyl, and piperidinyl, wherein each of methyl, ethyl, propyl is optionally substituted with phenyl, methoxy, ethoxy, butoxy, wherein phenyl is optionally substituted with fluoro, chloro, methyl, ethyl, propyl, fluoromethyl, difluoromethyl, trifluoromethyl, fluoroethyl, difluoroethyl, trifluoroethyl, methoxy, ethoxy, butoxy, and wherein piperidinyl is optionally substituted with methyl, ethyl, or propyl;

n is 1 or 2;

m is 0, 1, or 2;

A is a single bond or C(O);

each $R^1$ is independently selected from chloro, bromo, fluoro, methyl, ethyl, and propyl;

each $R^2$ is independently selected from —$NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl;

$R^3$ is hydrogen, methyl, ethyl, propyl, butyl, cyclopropyl, or cyclobutyl;

$R^4$ is a six- to twelve-membered heteroaryl having at least one aromatic ring and at least two nitrogen atoms, wherein the heteroaryl is optionally substituted with one, two, or three members independently selected from bromo, chloro, fluoro, cyano, methyl, ethyl, propyl, —$NH_2$, and the $C_{2-4}$ alkynyl moiety substituted with pyridinyl, phenyl, pyrazolyl, pyrazinyl, and pyrimidinyl, where each of the pyridinyl, phenyl, pyrazolyl, pyrazinyl, and pyrimidinyl moiety is optionally substituted with fluoro, chloro, bromo, iodo, fluoromethyl, difluoromethyl, trifluoromethyl, fluoroethyl, difluoroethyl, trifluoroethyl, fluoropropyl, difluoropropyl, or trifluoropropyl; and $R^5$ is hydrogen, wherein $R^5$ and $R^3$ together with the atoms to which they are attached optionally form pyrrolidinyl;

when Y is $CH_2$, X is N; when X is CH, Y is O or NR' wherein R' is hydrogen, optionally substituted alkyl, optionally substituted heterocycloalkyl, optionally substituted aryl, optionally substituted haloalkyl, or optionally substituted cycloalkyl; or a pharmaceutically acceptable salt, isomer, or a mixture thereof.

The compounds of formulae (J) or (I) may have the structure of formula (IIa):

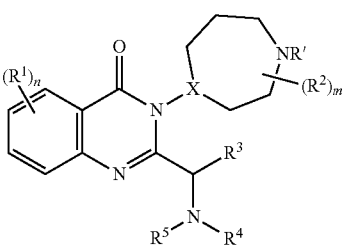

(IIIa)

wherein n, m, X, R', R¹, R², R³, R⁴, and R⁵ are described herein;

or a pharmaceutically acceptable salt, isomer, or a mixture thereof.

The compounds of formulae (J) or (I) may have the structure of formula (IIb):

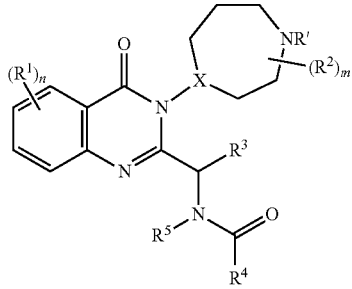

(IIIb)

wherein n, m, X, R', R¹, R², R³, R⁴, and R⁵ are described herein;

or a pharmaceutically acceptable salt, isomer, or a mixture thereof.

The compounds of formulae (J) or (I) may have the structure of formula (IIc):

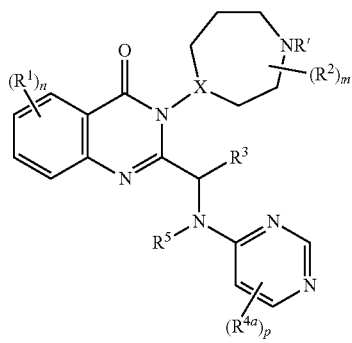

(IIIc)

wherein n, m, p, X, R', R¹, R², R³, R⁴ᵃ, and R⁵ are defined herein;

or a pharmaceutically acceptable salt, isomer, or a mixture thereof.

The compounds of formulae (J) or (I) may have the structure of formula (IIId):

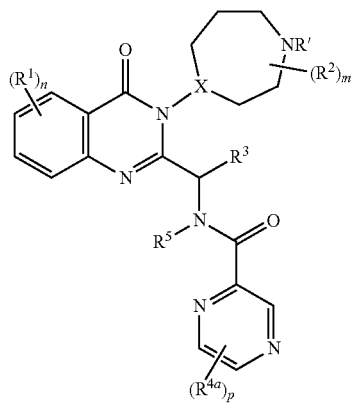

(IIId)

wherein n, m, p, X, R', R¹, R², R³, R⁴, and R⁵ are defined herein;

or a pharmaceutically acceptable salt, isomer, or a mixture thereof.

The compounds of formulae (J) or (I) may have the structure of formula (IV):

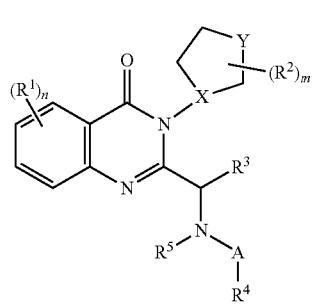

(IV)

wherein n, m, A, X, R¹, R², R³, R⁴, and R⁵ are defined herein;

Y is O, NR', or CH₂, wherein R' is defined herein;

or a pharmaceutically acceptable salt, isomer, or a mixture thereof.

In some embodiments, the compounds have the structure of formula (IV), wherein,

B is a four- to eight-membered heterocycloalkyl having at least one nitrogen atom, wherein heterocycloalkyl is optionally substituted with halo, methyl, ethyl, propyl, butyl, oxetanyl, fluoromethyl, difluoromethyl, trifluoromethyl, fluoroethyl, difluoroethyl, trifluoroethyl, cyclopropyl, cyclobutyl, and piperidinyl, wherein each of methyl, ethyl, propyl is optionally substituted with phenyl, methoxy, ethoxy, butoxy, wherein phenyl is optionally substituted with fluoro, chloro, methyl, ethyl, propyl, fluoromethyl, difluoromethyl, trifluoromethyl, fluoroethyl, difluoroethyl, trifluoroethyl, methoxy, ethoxy, butoxy, and wherein piperidinyl is optionally substituted with methyl, ethyl, or propyl;

n is 1 or 2;

m is 0, 1, or 2;

A is a single bond or C(O);

each R¹ is independently selected from chloro, bromo, fluoro, methyl, ethyl, and propyl;

each R² is independently selected from —NH₂, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl;

R$^3$ is hydrogen, methyl, ethyl, propyl, butyl, cyclopropyl, or cyclobutyl;

R$^4$ is a six- to twelve-membered heteroaryl having at least one aromatic ring and at least two nitrogen atoms, wherein the heteroaryl is optionally substituted with one, two, or three members independently selected from bromo, chloro, fluoro, cyano, methyl, ethyl, propyl, —NH$_2$, and the C$_{2-4}$ alkynyl moiety substituted with pyridinyl, phenyl, pyrazolyl, pyrazinyl, and pyrimidinyl, where each of the pyridinyl, phenyl, pyrazolyl, pyrazinyl, and pyrimidinyl moiety is optionally substituted with fluoro, chloro, bromo, iodo, fluoromethyl, difluoromethyl, trifluoromethyl, fluoroethyl, difluoroethyl, trifluoroethyl, fluoropropyl, difluoropropyl, or trifluoropropyl; and R$^5$ is hydrogen, wherein R$^5$ and R$^3$ together with the atoms to which they are attached optionally form pyrrolidinyl;

when Y is CH$_2$, X is N; when X is CH, Y is O or NR' wherein R' is hydrogen, optionally substituted alkyl, optionally substituted heterocycloalkyl, optionally substituted aryl, optionally substituted haloalkyl, or optionally substituted cycloalkyl;

or a pharmaceutically acceptable salt, isomer, or a mixture thereof.

The compounds of formulae (J) or (I) may have the structure of formula (IVa):

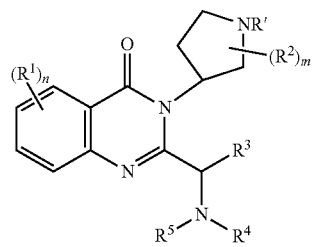

(IVa)

wherein n, m, R', R$^1$, R$^2$, R$^3$, R$^4$, and R$^5$ are described herein;

or a pharmaceutically acceptable salt, isomer, or a mixture thereof.

The compounds of formulae (J) or (I) may have the structure of formula (IVb):

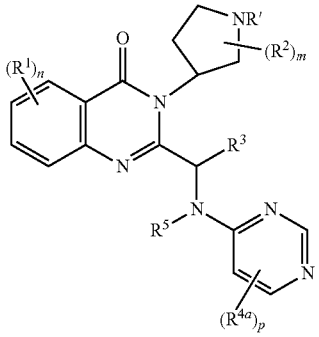

(IVb)

wherein n, m, p, R', R$^1$, R$^2$, R$^3$, R$^{4a}$, and R$^5$ are described herein;

or a pharmaceutically acceptable salt, isomer, or a mixture thereof.

The compounds of formulae (J) or (I) may have the structure of formula (IVc):

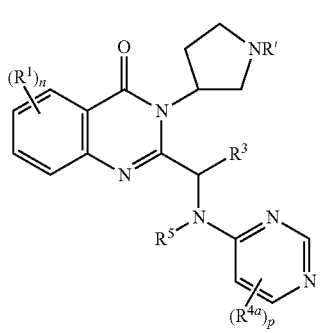

(IVc)

wherein n, p, R', R$^1$, R$^2$, R$^3$, R$^{4a}$, and R$^5$ are defined herein;

or a pharmaceutically acceptable salt, isomer, or a mixture thereof.

The compounds of formulae (J) or (I) may have the structure of formula (IVd):

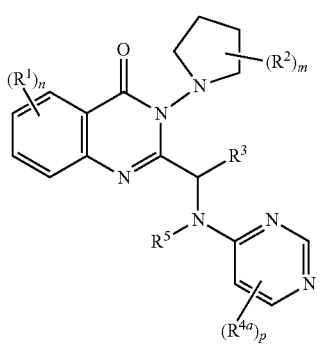

(IVd)

wherein n, m, p, R$^1$, R$^2$, R$^3$, R$^{4a}$, and R$^5$ are described herein;

or a pharmaceutically acceptable salt, isomer, or a mixture thereof.

The compounds of formulae (J) or (I) may have the structure of formula (IVe):

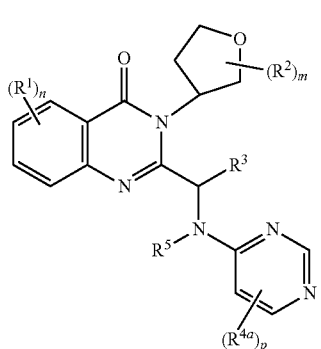

(IVe)

wherein n, m, p, R$^1$, R$^2$, R$^3$, R$^{4a}$, and R$^5$ are described herein;

or a pharmaceutically acceptable salt, isomer, or a mixture thereof.

The compounds of formulae (J) or (I) may have the structure of formula (V):

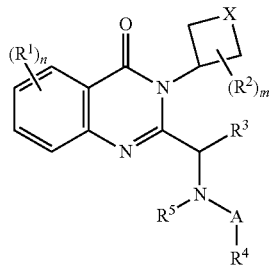

(V)

wherein n, m, A, X, $R^1$, $R^2$, $R^3$, $R^4$, and $R^5$ are described herein;

or a pharmaceutically acceptable salt, isomer, or a mixture thereof.

In certain embodiments, the compounds have the structure of formula (V), wherein X and Y is O or NR'; and n, m, A, $R^1$, $R^2$, $R^3$, $R^4$, $R^5$, and R' are defined herein;

or a pharmaceutically acceptable salt, isomer, or a mixture thereof.

In some embodiments, the compounds have the structure of formula (V), wherein,

B is a four- to eight-membered heterocycloalkyl having at least one nitrogen atom, wherein heterocycloalkyl is optionally substituted with halo, methyl, ethyl, propyl, butyl, oxetanyl, fluoromethyl, difluoromethyl, trifluoromethyl, fluoroethyl, difluoroethyl, trifluoroethyl, cyclopropyl, cyclobutyl, and piperidinyl, wherein each of methyl, ethyl, propyl is optionally substituted with phenyl, methoxy, ethoxy, butoxy, wherein phenyl is optionally substituted with fluoro, chloro, methyl, ethyl, propyl, fluoromethyl, difluoromethyl, trifluoromethyl, fluoroethyl, difluoroethyl, trifluoroethyl, methoxy, ethoxy, butoxy, and wherein piperidinyl is optionally substituted with methyl, ethyl, or propyl;

n is 1 or 2;

m is 0, 1, or 2;

A is a single bond or C(O);

each $R^1$ is independently selected from chloro, bromo, fluoro, methyl, ethyl, and propyl;

each $R^2$ is independently selected from —$NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl;

$R^3$ is hydrogen, methyl, ethyl, propyl, butyl, cyclopropyl, or cyclobutyl;

$R^4$ is a six- to twelve-membered heteroaryl having at least one aromatic ring and at least two nitrogen atoms, wherein the heteroaryl is optionally substituted with one, two, or three members independently selected from bromo, chloro, fluoro, cyano, methyl, ethyl, propyl, —$NH_2$, and the $C_{2-4}$ alkynyl moiety substituted with pyridinyl, phenyl, pyrazolyl, pyrazinyl, and pyrimidinyl, where each of the pyridinyl, phenyl, pyrazolyl, pyrazinyl, and pyrimidinyl moiety is optionally substituted with fluoro, chloro, bromo, iodo, fluoromethyl, difluoromethyl, trifluoromethyl, fluoroethyl, difluoroethyl, trifluoroethyl, fluoropropyl, difluoropropyl, or trifluoropropyl; and $R^5$ is hydrogen, wherein $R^5$ and $R^3$ together with the atoms to which they are attached optionally form pyrrolidinyl;

when Y is $CH_2$, X is N; when X is CH, Y is O or NR' wherein R' is hydrogen, optionally substituted alkyl, optionally substituted heterocycloalkyl, optionally substituted aryl, optionally substituted haloalkyl, or optionally substituted cycloalkyl;

or a pharmaceutically acceptable salt, isomer, or a mixture thereof.

The compounds of formulae (J) or (I) may have the structure of formula (Va):

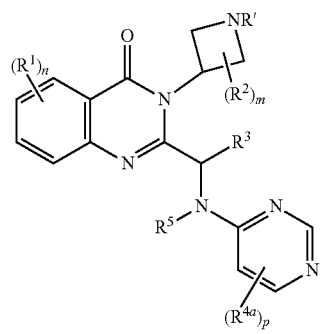

(Va)

wherein n, m, p, R', $R^1$, $R^2$, $R^3$, $R^{4a}$, and $R^5$ are described herein;

or a pharmaceutically acceptable salt, isomer, or a mixture thereof.

The compounds of formulae (J) or (I) may have the structure of formula (VI):

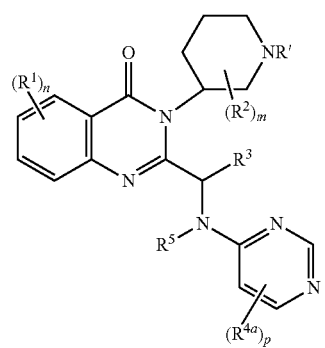

(VI)

wherein n, m, p, R', $R^1$, $R^2$, $R^3$, $R^{4a}$, and $R^5$ are described herein;

or a pharmaceutically acceptable salt, isomer, or a mixture thereof.

In some embodiments, the compounds have the structure of formula (VI), wherein,

B is a four- to eight-membered heterocycloalkyl having at least one nitrogen atom, wherein heterocycloalkyl is optionally substituted with halo, methyl, ethyl, propyl, butyl, oxetanyl, fluoromethyl, difluoromethyl, trifluoromethyl, fluoroethyl, difluoroethyl, trifluoroethyl, cyclopropyl, cyclobutyl, and piperidinyl, wherein each of methyl, ethyl, propyl is optionally substituted with phenyl, methoxy, ethoxy, butoxy, wherein phenyl is optionally substituted with fluoro, chloro, methyl, ethyl, propyl, fluoromethyl, difluoromethyl, trifluoromethyl, fluoroethyl, difluoroethyl, trifluoroethyl, methoxy, ethoxy, butoxy, and wherein piperidinyl is optionally substituted with methyl, ethyl, or propyl;

n is 1 or 2;
m is 0, 1, or 2;
A is a single bond or C(O);
each $R^1$ is independently selected from chloro, bromo, fluoro, methyl, ethyl, and propyl;
each $R^2$ is independently selected from —$NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl;
$R^3$ is hydrogen, methyl, ethyl, propyl, butyl, cyclopropyl, or cyclobutyl;
$R^4$ is a six- to twelve-membered heteroaryl having at least one aromatic ring and at least two nitrogen atoms, wherein the heteroaryl is optionally substituted with one, two, or three members independently selected from bromo, chloro, fluoro, cyano, methyl, ethyl, propyl, —$NH_2$, and the $C_{2-4}$ alkynyl moiety substituted with pyridinyl, phenyl, pyrazolyl, pyrazinyl, and pyrimidinyl, where each of the pyridinyl, phenyl, pyrazolyl, pyrazinyl, and pyrimidinyl moiety is optionally substituted with fluoro, chloro, bromo, iodo, fluoromethyl, difluoromethyl, trifluoromethyl, fluoroethyl, difluoroethyl, trifluoroethyl, fluoropropyl, difluoropropyl, or trifluoropropyl; and
$R^5$ is hydrogen, wherein $R^5$ and $R^3$ together with the atoms to which they are attached optionally form pyrrolidinyl;
when Y is $CH_2$, X is N; when X is CH, Y is O or NR' wherein R' is hydrogen, optionally substituted alkyl, optionally substituted heterocycloalkyl, optionally substituted aryl, optionally substituted haloalkyl, or optionally substituted cycloalkyl;
or a pharmaceutically acceptable salt, isomer, or a mixture thereof.

In one embodiment, n is 0. In some embodiments, n is 1, 2, 3, or 4. In some embodiments, n is 1, 2, or 3. In other embodiments, n is 1 or 2. In certain embodiments, n is 1 and the $R^1$ moiety may be located on any position of the phenyl of the quinazolinone ring. In another embodiment, n is 2. Both of the $R^1$ substituents or moieties may be the same or different. Two $R^1$ moieties may be located on any two positions of the phenyl of the quinazolinone ring. By way of example, the first $R^1$ may be ortho, meta, or para to the second $R^1$. In yet another embodiment, n is 3. All of the $R^1$ substituents or moieties may be the same or different, or two $R^1$ may be the same and different from the third $R^1$. Three $R^1$ moieties may be located on any three positions of the phenyl of the quinazolinone ring. For example, the first $R^1$ may be ortho to the second $R^1$, and the first $R^1$ may be para to the third $R^1$. In yet another embodiment, n is 4. All $R^1$ substituents may be the same or different, three $R^1$ may be the same and different from the fourth $R^1$, two $R^1$ may be the same and different from the third and the fourth $R^1$.

In some other embodiments, each $R^1$ is independently halo, cyano, optionally substituted $C_{1-6}$ alkyl, optionally substituted $C_{1-6}$ haloalkyl, optionally substituted $C_{1-6}$ alkoxy, hydroxy, optionally substituted $C_{3-6}$ cycloalkyl, optionally substituted $C_{3-6}$ heterocycloalkyl, optionally substituted $C_{6-10}$ aryl, optionally substituted $C_{4-8}$ heteroaryl, or optionally substituted $C_{1-6}$ alkylsulfonyl. In certain embodiments, each $R^1$ is independently halo, cyano, optionally substituted $C_{1-4}$ alkyl, optionally substituted $C_{1-4}$ haloalkyl, optionally substituted $C_{1-4}$ alkoxy, optionally substituted $C_{3-6}$ cycloalkyl, or optionally substituted $C_{1-4}$ alkylsulfonyl. In other embodiments, each $R^1$ is independently halo, cyano, $C_{1-4}$ haloalkyl, $C_{1-4}$ alkyl, or $C_{1-4}$ alkylsulfonyl. In certain embodiments, each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl. In some embodiments, each $R^1$ is independently fluoro, chloro, iodo, cyano, methyl, ethyl, difluoromethyl (—$CHF_2$), trifluoromethyl (—$CF_3$), methoxy, methylsulfonyl (—$SO_2CH_3$), cyclopropylmethyl, or cyclopropyl. In one embodiment, each $R^1$ is independently fluoro, chloro, cyano, methylsulfonyl, methyl, or trifluoromethyl.

In one embodiment, m is 0. In some embodiments, m is 1, 2, or 3. In certain other embodiments, m is 1 or 2. In certain embodiments, m is 1. In other embodiments, m is 2. In yet other embodiments where m is 1, 2, or 3, the $R^2$ substituent or moiety may be located on any position of the B heterocycloalkyl, including the heteroatom in the B heterocycloalkyl.

In certain embodiments, each $R^2$ is independently selected from —$NH_2$, halo, optionally substituted alkyl, and optionally substituted haloalkyl. In some embodiments, each $R^2$ is independently selected from halo, —$NH_2$, $C_{1-6}$ alkyl, and $C_{1-6}$ haloalkyl. In additional embodiments, each $R^2$ independently selected from chloro, fluoro, bromo, —$NH_2$, methyl, ethyl, propyl, butyl, pentyl, trifluoromethyl, difluoromethyl, fluoromethyl, trifluoroethyl, difluoroethyl, fluoroethyl, trifluoropropyl, difluoropropyl, and fluoropropyl.

In certain embodiments, $R^3$ is hydrogen, optionally substituted $C_{1-6}$ alkyl, optionally substituted $C_{3-8}$ cycloalkyl, or optionally substituted $C_{6-10}$ aryl. In one embodiment, $R^3$ is hydrogen, $C_{3-6}$ cycloalkyl, $C_{6-10}$ aryl, or $C_{1-4}$ alkyl optionally substituted with hydroxy, $C_{6-10}$ aryl$C_{1-4}$ alkoxy, or $C_{3-6}$ cycloalkyl. In some embodiments, $R^3$ is hydrogen, methyl, ethyl, propyl, butyl, cyclopropylmethyl, cyclopropylethyl, cyclobutylmethyl, cyclobutylethyl, cyclopropyl, cyclobutyl, cyclopentyl, cyclohexyl, —$CH_2OH$, —$C_2H_4OH$, —$C_3H_6OH$, benzyloxymethy

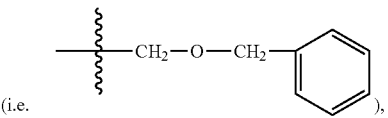 [SMILES: *COCc1ccccc1]

(i.e. ), or phenyl

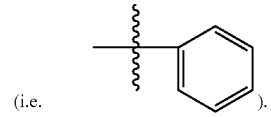 [SMILES: *c1ccccc1]

(i.e. ).

In additional embodiments, $R^5$ is hydrogen or optionally substituted $C_{1-6}$ alkyl. In some embodiments, $R^5$ is hydrogen or $C_{1-4}$ alkyl. In certain embodiments, $R^5$ is hydrogen, methyl, ethyl, propyl or butyl. In certain other embodiments, $R^5$ is hydrogen.

In further embodiments, $R^3$ and $R^5$ with the atoms to which they are attached (e.g. carbon and nitrogen, respectively) optionally form a heterocyclic ring. In other embodiments, the $R^3$-$R^5$ heterocyclic ring is a three- to eight-membered heterocycloalkyl (i.e. heterocycloalkyl having three to eight ring members and at least one ring member is a heteroatom). In other embodiments, the $R^3$-$R^5$ heterocyclic ring is a four- to seven-membered heterocycloalkyl (i.e. heterocycloalkyl having four to seven ring members and at least one ring member is a heteroatom). In one embodiment, the R³-R⁵ heterocyclic ring is a five-membered heterocycloalkyl. In certain other embodiments, the R³-R⁵ heterocyclic ring is $C_{3-8}$ heterocycloalkyl optionally substituted with halo. In some embodiments, the R³-R⁵ heterocyclic ring is azepanyl, azetidinyl, piperidinyl, and pyrrolidinyl, each of which is optionally substituted with fluoro, chloro, bromo, or iodo. In some other embodiments, the R³-R⁵ heterocyclic ring is pyrrolidinyl. In one other embodiment, the R³-R⁵ heterocyclic ring is a five-membered heterocycloalkyl substituted with halo. In other additional embodiments, the R³-R⁵ heterocyclic ring is pyrrolidinyl substituted with fluoro, chloro, bromo, or iodo.

In one embodiment, R⁴ is heteroaryl having at least two nitrogen atoms and at least one aromatic ring and R⁴ heteroaryl is optionally substituted one, two, or three members independently selected from halo, cyano, —NH₂, $C_{1-6}$ alkyl, and $C_{1-6}$ haloalkyl. In certain embodiments, R⁴ heteroaryl is a six- to twelve-membered heteroaryl (i.e. heteroaryl having six to twelve ring members). R⁴ heteroaryl may be a monocyclic or bicyclic heteroaryl. In some embodiments, R⁴ heteroaryl is a monocyclic heteroaryl having at least two nitrogen atoms. In certain embodiments, R⁴ heteroaryl is a bicyclic heteroaryl having at least one aromatic ring, at least two nitrogen atoms, and at least one additional heteroatom selected from N, O, or S. In certain other embodiments, R⁴ heteroaryl is selected from purinyl, pyrimidinyl, thiazolopyrimidinyl, pyridopyrimidinyl, thienopyrimidinyl, pyrrolopyrimidinyl, furopyrimidinyl, and imidazotriazinyl.

In any of the foregoing formulae, R⁴ is heteroaryl optionally substituted with one, two, or three members independently selected from halo, cyano, —NH₂, $C_{1-6}$ alkyl, $C_{1-6}$ haloalkyl, $C_{2-6}$ alkynyl, wherein $C_{2-6}$ alkynyl is optionally substituted with $C_{6-10}$ aryl or $C_{4-8}$ heteroaryl, wherein each of the $C_{6-10}$ aryl or $C_{3-8}$ heteroaryl moieties is optionally substituted with fluoro, chloro, bromo, iodo, fluoromethyl, difluoromethyl, trifluoromethyl, fluoroethyl, difluoroethyl, or trifluoroethyl, wherein the R⁴ heteroaryl is selected from the group consisting of

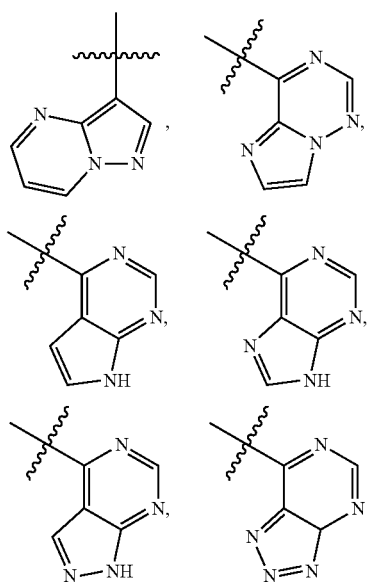

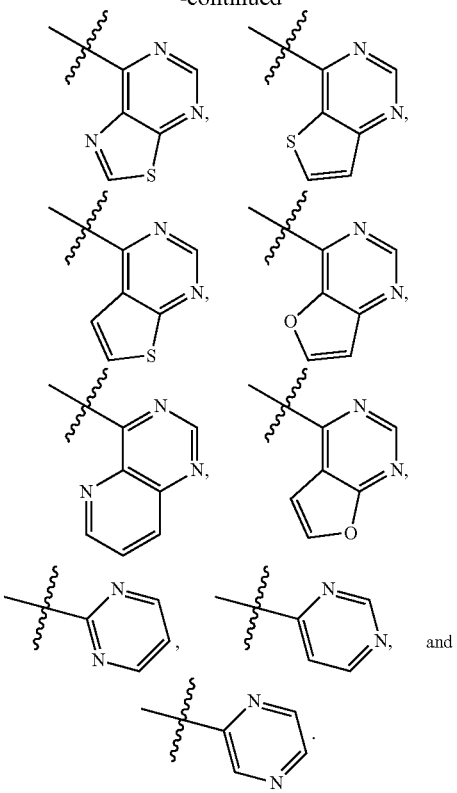

In any of the foregoing formulae, R⁴ heteroaryl is optionally substituted with $C_{2-6}$ alkynyl optionally substituted with $C_{6-10}$ aryl or $C_{4-8}$ heteroaryl, each of which is optionally substituted with one or two members independently selected from halo and $C_{1-6}$ haloalkyl. In some embodiment, R⁴ is heteroaryl optionally substituted with one member of $C_{2-6}$ alkynyl substituted with $C_{6-10}$ aryl or $C_{4-8}$ heteroaryl, wherein each of the $C_{6-10}$ aryl or $C_{3-8}$ heteroaryl moieties is optionally substituted with one member of fluoro, chloro, bromo, iodo, fluoromethyl, difluoromethyl, trifluoromethyl, fluoroethyl, difluoroethyl, or trifluoroethyl.

In some other embodiments, R⁴ is optionally substituted with one to three members independently selected from fluoro, chloro, bromo, iodo, cyano, methyl, ethyl, propyl, fluoromethyl, difluoromethyl, trifluoromethyl, fluoroethyl, difluoroethyl, —NH₂, and optionally substituted with

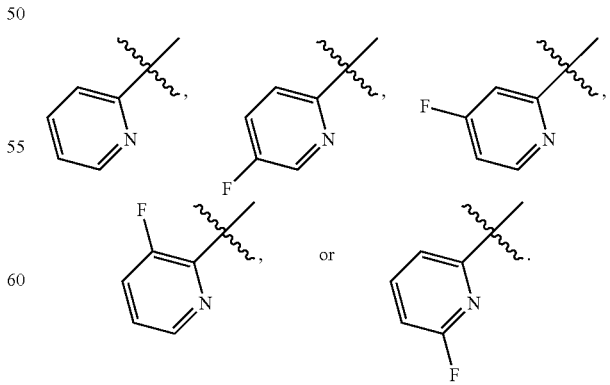

In certain other embodiments, R⁴ is selected from purinyl, pyrimidinyl, thiazolopyrimidinyl, pyridopyrimidinyl, thienopyrimidinyl, pyrrolopyrimidinyl, furopyrimidinyl, and imidazotriazinyl, each of which is optionally substituted with one, two, or three members independently selected from chloro, fluoro, bromo, iodo, methyl, ethyl, propyl, cyano, and —$NH_2$. In certain other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with one or two members independently selected from chloro, fluoro, bromo, iodo, methyl, ethyl, propyl, and —$NH_2$. In other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with two members independently selected from chloro, fluoro, bromo, iodo, methyl, ethyl, propyl, and —$NH_2$. In other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with one member selected from chloro, fluoro, bromo, iodo, and —$NH_2$. In some other embodiments, $R^4$ is pyrimidinyl or pyrazinyl and $R^4$ is optionally substituted with at least one —$NH_2$. In certain other embodiments, $R^4$ is pyrimidinyl or pyrazinyl, each of which is substituted with two or three members independently selected from chloro, fluoro, bromo, iodo, methyl, ethyl, propyl, cyano, and —$NH_2$.

In one embodiment, p is 0. In certain embodiments, p is 1, 2, or 3. In some embodiments, p is 1 or 2. In some embodiments, p is 1 and $R^{4a}$ moiety may be located on any position of the pyrimidinyl or pyrazinyl ring. In another embodiment, p is 2 and both $R^{4a}$ substituents or moieties may be the same or different; each of the two $R^{4a}$ moiety may be located on any position of the pyrimdinyl or pyrazinyl ring. In yet another embodiment, p is 3 and all $R^{4a}$ substituents may be the same or different, or two $R^{4a}$ may be the same and different from the third $R^{4a}$.

In the present application, each $R^{4a}$ is independently selected from halo, —$NH_2$, cyano, $C_{2-4}$ alkynyl, $C_{1-4}$ haloalkyl, and $C_{1-4}$ alkyl, wherein the $C_{2-4}$ alkynyl moiety is optionally substituted with $C_{6-10}$ aryl or $C_{4-8}$ heteroaryl, wherein each of the $C_{6-10}$ aryl or $C_{3-8}$ heteroaryl moieties is optionally substituted with fluoro, chloro, bromo, iodo, fluoromethyl, difluoromethyl, trifluoromethyl, fluoroethyl, difluoroethyl, or trifluoroethyl. In some embodiments, each $R^{4a}$ is independently selected from fluoro, chloro, bromo, iodo, cyano, —$NH_2$, methyl, ethyl, propyl, fluoromethyl, difluoromethyl, trifluoromethyl, fluoroethyl, and difluoroethyl, wherein at least one $R^{4a}$ is —$NH_2$. In additional embodiments, p is 2 or 3, and at least one $R^{4a}$ is —$NH_2$. Each and every variation of p and $R^{4a}$ may be combined with each and every variation of n, m, $R^1$, $R^2$, $R^3$, and $R^5$ as described above.

In some embodiments, A is C(O). In certain embodiments, A is a single bond. Each and every variation of A may be combined with each and every variation of n, m, X, R', $R^1$, $R^2$, $R^3$, $R^4$, and $R^5$ as described above. In some other embodiments, A is C(O) and $R^4$ heteroaryl is a bicyclic group defined above. In other embodiments, A is a single bond and $R^4$ heteroaryl is a bicyclic group defined above. In additional embodiments, A is C(O) and $R^4$ heteroaryl is a monocyclic group selected from pyrimidinyl and pyrazinyl. In other embodiments, A is a single bond and $R^4$ heteroaryl is a monocyclic group selected from pyrimidinyl and pyrazinyl.

In further embodiments, A' is $OR^4$. In some further embodiments, A' is $N(R^5)C(O)R^4$. In yet further embodiments, A' is $NR^5R^4$. Each and every variation of A' may be combined with each and every variation of n, $R^1$, $R^2$, $R^3$, $R^4$, and $R^5$ as described above.

In additional embodiments, B is a four- to ten-membered heterocycloalkyl which is optionally substituted one to three members independently selected from independently selected from halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl. In yet additional embodiments, B is a four- to eight-membered heterocycloalkyl which is optionally substituted with one or two members independently selected from halo, $C_{1-6}$ alkyl, $C_{3-8}$ heterocycloalkyl, $C_{1-6}$ haloalkyl, and $C_{3-8}$ cycloalkyl, wherein each of the $C_{1-6}$ alkyl moiety is optionally substituted with $C_{6-10}$ aryl, $C_{1-6}$ alkoxy, wherein $C_{6-10}$ aryl is optionally substituted with one or two members independently selected from halo, $C_{1-6}$ alkyl, $C_{1-6}$ haloalkyl, $C_{3-8}$ heterocycloalkyl, $C_{3-8}$ cycloalkyl moiety, and wherein $C_{3-8}$ heterocycloalkyl is optionally substituted with $C_{1-6}$ alkyl. The B heterocycloalkyl may be a single ring or multiple rings that are fused, bridged, or spiro. In some embodiments, B heterocycloalkyl is selected from azepanyl, diazepanyl, pyrrolidinyl, tetrahydrofuranyl, oxetanyl, piperidinyl, and piperazinyl. In certain embodiments, B is azepanyl, diazepanyl, pyrrolidinyl, tetrahydrofuranyl, oxetanyl, piperidinyl, or piperazinyl; each of the azepanyl, diazepanyl, pyrrolidinyl, tetrahydrofuranyl, oxetanyl, piperidinyl, and piperazinyl moieties is optionally substituted with one or two members independently selected from halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl. In any of the foregoing embodiments, B heteroaryl is optionally substituted with methyl, ethyl, propyl, butyl, pentyl, trifluoromethyl, difluoromethyl, fluoromethyl, trifluoroethyl, difluoroethyl, fluoroethyl, trifluoropropyl, difluoropropyl, fluoropropyl, butoxyethyl, methylpiperidinyl, ethylpiperidinyl, propylpiperidinyl, phenylmethyl, phenylethyl, trifluormethylphenylmethyl, difluoromethylphenylmethyl, fluoromethylphenylmethyl, trifluorethylphenylmethyl, difluoroethylphenylmethyl, fluoroethylphenylmethyl, methoxyphenylmethyl, ethoxyphenylmethyl, methoxyphenylethyl, and ethoxyphenylethyl.

In any of the foregoing embodiments, B is optionally substituted with one, two, or three members of $R^2$ substituents. In additional embodiments, B heterocycloalkyl is a fused-heterocycloalkyl, bridged-heterocycloalkyl, or spiroheterocycloalkyl. In some additional embodiments, B heterocycloalkyl is an eight-membered spiro-heterocycloalkyl having at least one N ring atom. In further embodiments, B is a six- to eight-membered fused-heterocycloalkyl, bridged-heterocycloalkyl, or spiro-heterocycloalkyl, wherein each of fused-heterocycloalkyl, bridged-heterocycloalkyl, or spiro-heterocycloalkyl is optionally substituted with one or two members independently selected from halo, optionally substituted $C_{1-6}$ alkyl, optionally substituted $C_{3-8}$ heterocycloalkyl, $C_{1-6}$ haloalkyl, and optionally substituted $C_{3-8}$ cycloalkyl. In certain additional embodiments, B heterocycloalkyl is an eight-membered bridged-heterocycloalkyl having at least one N ring atom. In yet additional embodiments, B heterocycloalkyl is a six-membered fused-heterocycloalkyl having at least one N ring atom. The carbon or the heteroatom ring atoms on B heterocycloalkyl may be further substituted with $R^2$. In addition, B may be attached to the quinazolinone ring by the carbon or the heteroatom ring atoms. Each and every variation of B may be combined with each and every variation of n, m, A', $R^1$, $R^2$, and $R^3$ as described above.

In other embodiments, X is CH or N. In one embodiment, X is CH and the attachment point to the quinazolinone ring. In another embodiment, X is N and the attachment point to the quinazolinone ring. In additional embodiments, Y is O, NR' or CH₂. In some additional embodiments, Y is O. In certain additional embodiments, Y is NR'. In other additional embodiments, Y is CH₂.

In some embodiments, R' is hydrogen, optionally substituted alkyl, optionally substituted haloalkyl, optionally substituted heterocycloalkyl, optionally substituted aryl, and optionally substituted cycloalkyl. In other embodiments, each R' is independently selected from hydrogen, $C_{1-6}$ alkyl, $C_{3-8}$ heterocycloalkyl, $C_{1-6}$ haloalkyl, and $C_{3-8}$ cycloalkyl, wherein each of the $C_{1-6}$ alkyl moiety is optionally substituted with $C_{6-10}$ aryl, $C_{1-6}$ alkoxy, wherein $C_{6-10}$ aryl is optionally substituted with one or two members independently selected from halo, $C_{1-6}$ alkyl, $C_{1-6}$ haloalkyl, $C_{3-8}$ heterocycloalkyl, $C_{3-8}$ cycloalkyl moiety, and wherein $C_{3-8}$ heterocycloalkyl is optionally substituted with $C_{1-6}$ alkyl. In additional embodiments, each R' independently selected from hydrogen, methyl, ethyl, propyl, butyl, pentyl, cyclopropyl, cyclobutyl, oxetanyl, trifluoromethyl, difluoromethyl, fluoromethyl, trifluoroethyl, difluoroethyl, fluoroethyl, trifluoropropyl, difluoropropyl, fluoropropyl, butoxyethyl, methylpiperidinyl, ethylpiperidinyl, propylpiperidinyl, phenylmethyl, phenylethyl, trifluormethylphenylmethyl, difluoromethylphenylmethyl, fluoromethylphenylmethyl, trifluorethylphenylmethyl, difluoroethylphenylmethyl, fluoroethylphenylmethyl, methoxyphenylmethyl, ethoxyphenylmethyl, methoxyphenylethyl, and ethoxyphenylethyl. In other embodiments, each R□ independently selected from methyl, ethyl, propyl, butyl, pentyl, trifluoromethyl, difluoromethyl, fluoromethyl, trifluoroethyl, difluoroethyl, fluoroethyl, trifluoropropyl, difluoropropyl, fluoropropyl, butoxyethyl, methylpiperidinyl, ethylpiperidinyl, propylpiperidinyl, phenylmethyl, phenylethyl, trifluormethylphenylmethyl, difluoromethylphenylmethyl, fluoromethylphenylmethyl, trifluorethylphenylmethyl, difluoroethylphenylmethyl, fluoroethylphenylmethyl, methoxyphenylmethyl, ethoxyphenylmethyl, methoxyphenylethyl, and ethoxyphenylethyl.

In certain embodiments, W is CH or N. In certain other embodiments, W is CH. In yet other embodiments, W is N. Each and every variation of W may be combined with each and every variation of n, m, A', R¹, R², and R³ as described above.

The compounds of the present application may bear one or more chiral centers. The compounds bearing the chiral center have the same molecular formula and the same chemical name with different stereoisomer designations. For example, the below 2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile bearing one chiral center can be resolved into the (S) and (R) enantiomers, (S)-2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile and ((R)-2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile.

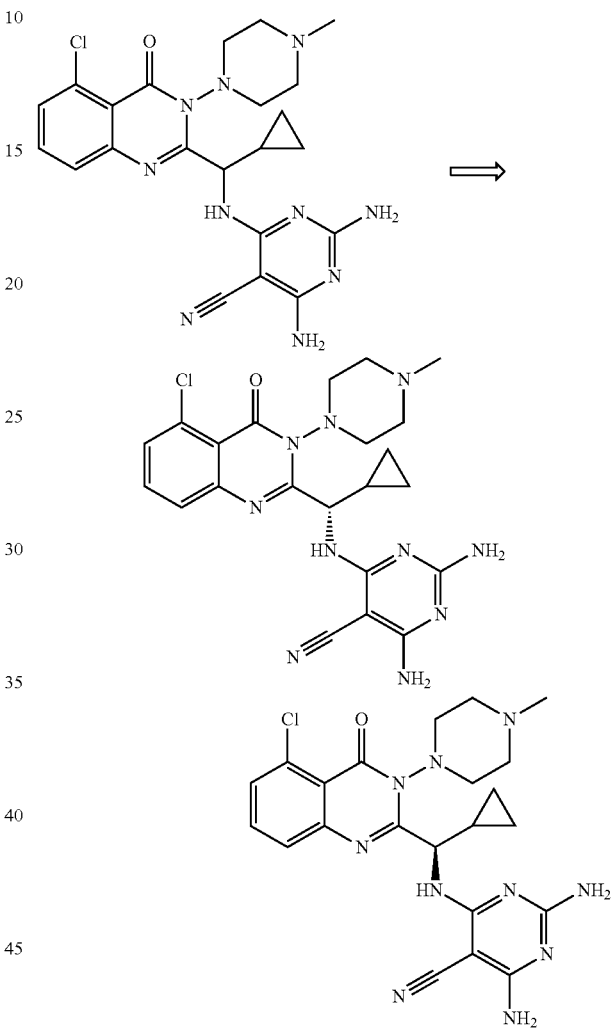

Representative compounds of the present application are listed in Table 1 below. Additional compounds are listed in Table 1a. The compounds may be named using the nomenclature systems and symbols that are commonly recognized in the art of chemistry including, for example, ChemBioDraw Ultra 12.0, Chemical Abstract Service (CAS), and International Union of Pure and Applied Chemistry (IUPAC). For example, compound 1 in Table 1 may be named as 2,4-diamino-6-[[(S)-[5-chloro-3-(4-methylpiperazin-1-yl)-4-oxo-quinazolin-2-yl]-cyclopropyl-methyl]amino]pyrimidine-5-carbonitrile or (S)-2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile using IUPAC or ChemBioDraw Ultra 12.0, respectively.

TABLE 1

Representative Compounds

| Compound | Structure |
|---|---|
| 1 | (chemical structure) |
| 2 | (chemical structure) |
| 3 | (chemical structure) |
| 4 | (chemical structure) |
| 5 | (chemical structure) |
| 6 | (chemical structure) |
| 7 | (chemical structure) |
| 8 | (chemical structure) |

TABLE 1-continued

Representative Compounds

| Compound | Structure |
|---|---|
| 9 | *(chemical structure)* |
| 10 | *(chemical structure)* |
| 11 | *(chemical structure)* |
| 12 | *(chemical structure)* |
| 13 | *(chemical structure)* |
| 14 | *(chemical structure)* |
| 15 | *(chemical structure)* |
| 16 | *(chemical structure)* |

TABLE 1-continued

Representative Compounds

| Compound | Structure |
|---|---|
| 17 | (chemical structure) |
| 18 | (chemical structure) |
| 19 | (chemical structure) |
| 20 | (chemical structure) |
| 21 | (chemical structure) |
| 22 | (chemical structure) |
| 23 | (chemical structure) |
| 24 | (chemical structure) |

TABLE 1-continued

Representative Compounds

| Compound | Structure |
|---|---|
| 25 | (chemical structure) |
| 26 | (chemical structure) |
| 27 | (chemical structure) |
| 28 | (chemical structure) |
| 29 | (chemical structure) |
| 30 | (chemical structure) |
| 31 | (chemical structure) |
| 32 | (chemical structure) |

TABLE 1-continued

Representative Compounds

| Compound | Structure |
|---|---|
| 33 | (structure) |
| 34 | (structure) |
| 35 | (structure) |
| 36 | (structure) |
| 37 | (structure) |
| 38 | (structure) |
| 39 | (structure) |
| 40 | (structure) |

TABLE 1-continued
Representative Compounds
| Compound | Structure |
|---|---|
| 41 | 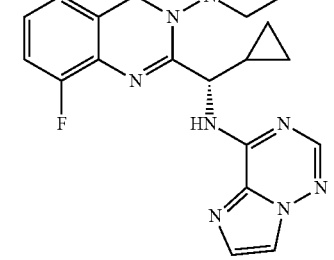 |
| 42 | 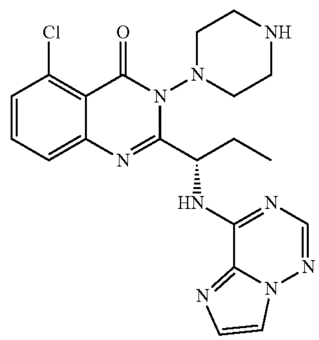 [SMILES: CC[C@H](Nc1ncnn2ccnc12)c1nc2cccc(Cl)c2c(=O)n1N1CCNCC1] |
| 43 | 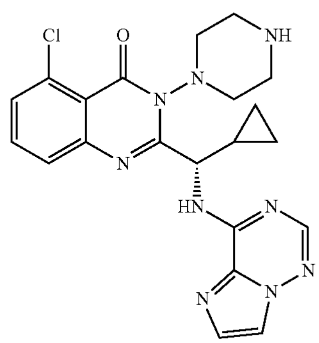 [SMILES: O=c1c2c(Cl)cccc2nc([C@@H](Nc2ncnn3ccnc23)C2CC2)n1N1CCNCC1] |
| 44 | 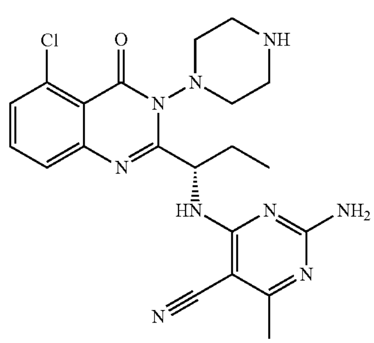 [SMILES: CC[C@H](Nc1nc(N)nc(C)c1C#N)c1nc2cccc(Cl)c2c(=O)n1N1CCNCC1] |
| 46 | 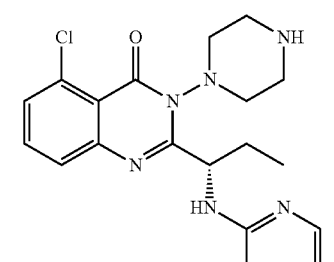 |
| 47 | |
| 48 | |
| 49 | |

TABLE 1-continued
Representative Compounds
| Compound | Structure |
|---|---|
| 50 | 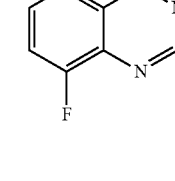 |
| 51 | 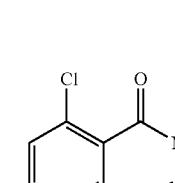 |
| 52 | 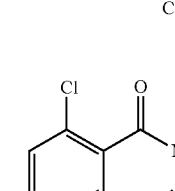 |
| 53 | 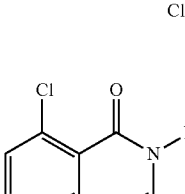 |
| 54 | 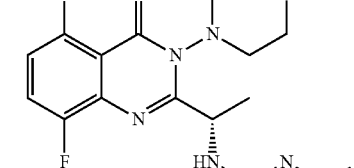 |
| 55 | 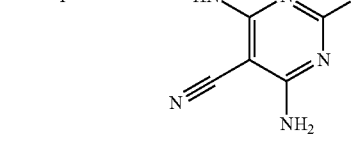 |
| 56 | 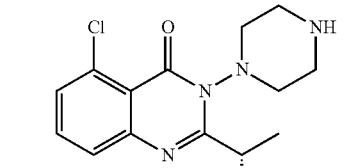 |
| 57 | 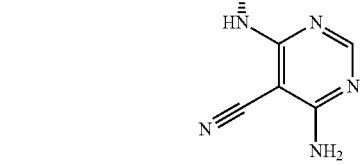 |

TABLE 1-continued
Representative Compounds
| Compound | Structure |
|---|---|
| 58 | 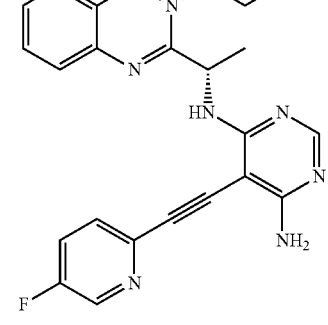 |
| 59 | 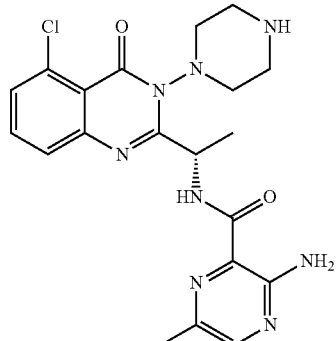 |
| 60 | 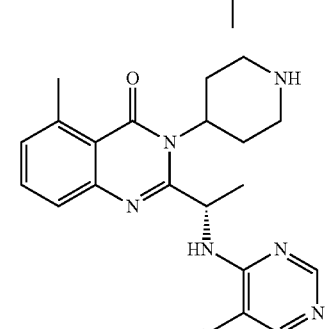 |
| 61 | 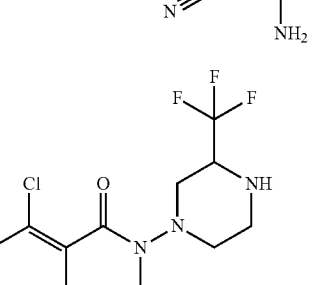 |
| 62 | 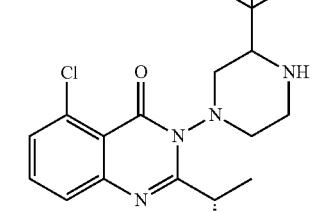 |
| 63 | 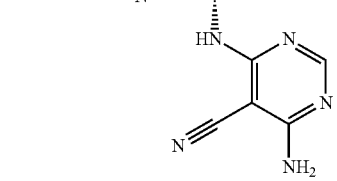 |
| 64 | 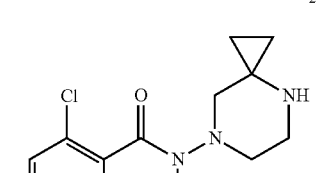 |
| 65 | 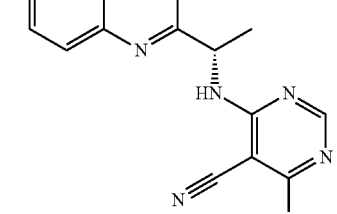 |

TABLE 1-continued

Representative Compounds

| Compound | Structure |
|---|---|
| 66 | (chemical structure) |
| 67 | (chemical structure) |
| 68 | (chemical structure) |
| 69 | (chemical structure) |
| 70 | (chemical structure) |
| 71 | (chemical structure) |
| 72 | (chemical structure) |
| 73 | (chemical structure) |

TABLE 1-continued

Representative Compounds

| Compound | Structure |
|---|---|
| 74 | (chemical structure) |
| 75 | (chemical structure) |
| 76 | (chemical structure) |
| 77 | (chemical structure) |
| 78 | (chemical structure) |
| 79 | (chemical structure) |
| 80 | (chemical structure) |
| 81 | (chemical structure) |

TABLE 1-continued
Representative Compounds
| Compound | Structure |
|---|---|
| 82 | 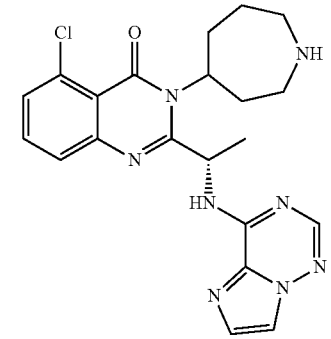 [SMILES: C[C@H](Nc1ncnn2ccnc12)c1nc2cccc(Cl)c2c(=O)n1C1CCCNCC1] |
| 83 | 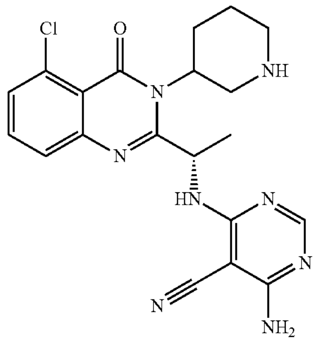 [SMILES: C[C@H](Nc1ncnc(N)c1C#N)c1nc2cccc(Cl)c2c(=O)n1C1CCCNC1] |
| 84 | 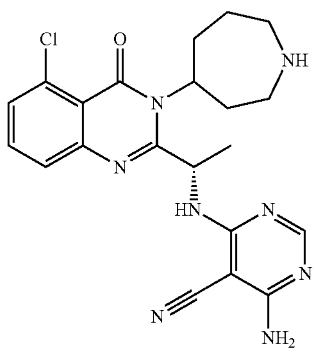 |
| 85 | 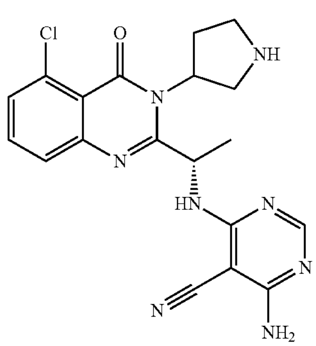 [SMILES: C[C@H](Nc1ncnc(N)c1C#N)c1nc2cccc(Cl)c2c(=O)n1C1CCNC1] |
TABLE 1-continued
Representative Compounds
| Compound | Structure |
|---|---|
| 86 | 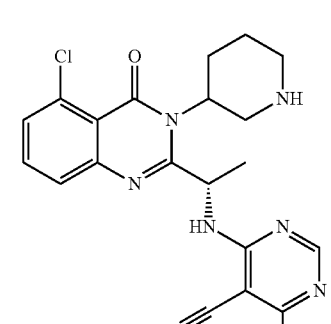 |
| 87 | 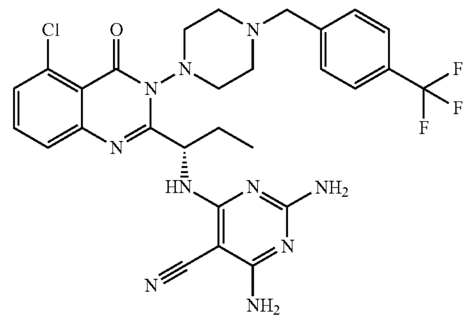 [SMILES: CC[C@H](Nc1nc(N)nc(N)c1C#N)c1nc2cccc(Cl)c2c(=O)n1N1CCN(Cc2ccc(C(F)(F)F)cc2)CC1] |
| 88 | 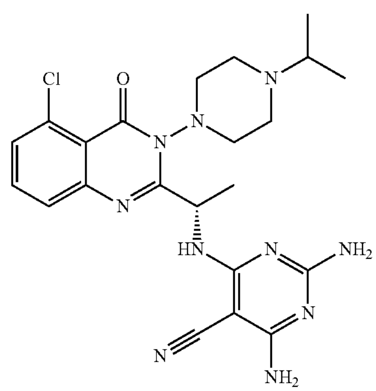 [SMILES: CC(C)N1CCN(n2c([C@H](C)Nc3nc(N)nc(N)c3C#N)nc3cccc(Cl)c3c2=O)CC1] |
| 89 | 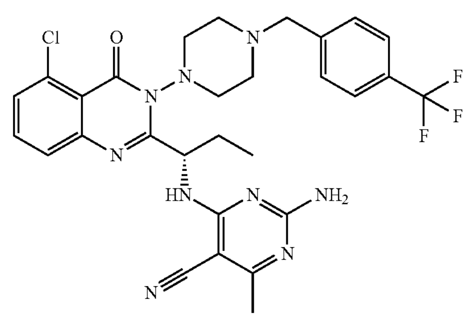 [SMILES: CC[C@H](Nc1nc(N)nc(C)c1C#N)c1nc2cccc(Cl)c2c(=O)n1N1CCN(Cc2ccc(C(F)(F)F)cc2)CC1] |

TABLE 1-continued
Representative Compounds
| Compound | Structure |
|---|---|
| 90 | 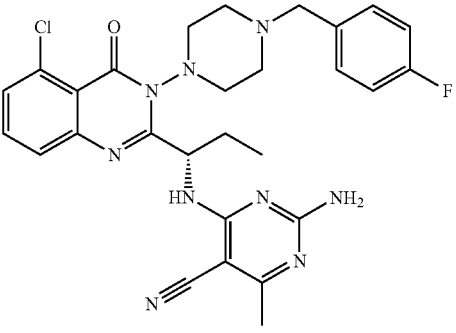 [SMILES: CC[C@H](Nc1nc(N)nc(C)c1C#N)c1nc2cccc(Cl)c2c(=O)n1N1CCN(Cc2ccc(F)cc2)CC1] |
| 91 | 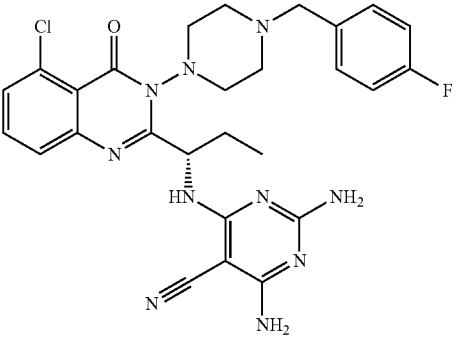 [SMILES: CC[C@H](Nc1nc(N)nc(N)c1C#N)c1nc2cccc(Cl)c2c(=O)n1N1CCN(Cc2ccc(F)cc2)CC1] |
| 92 | 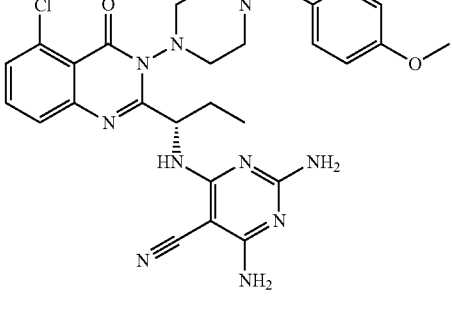 |
| 93 | 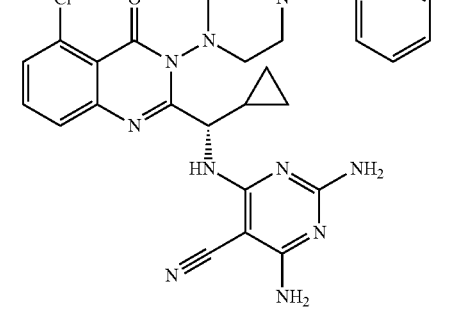 |
| 94 | 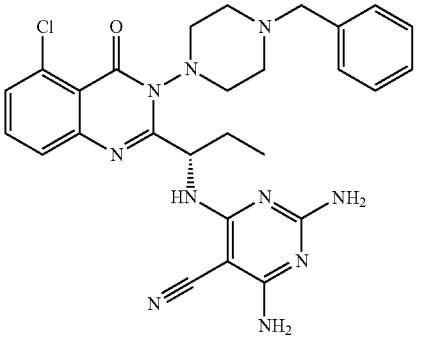 [SMILES: CC[C@H](Nc1nc(N)nc(N)c1C#N)c1nc2cccc(Cl)c2c(=O)n1N1CCN(Cc2ccccc2)CC1] |
| 95 | 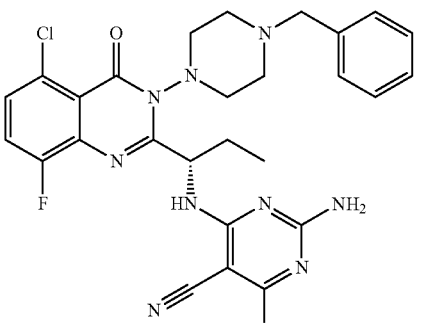 |
| 96 | 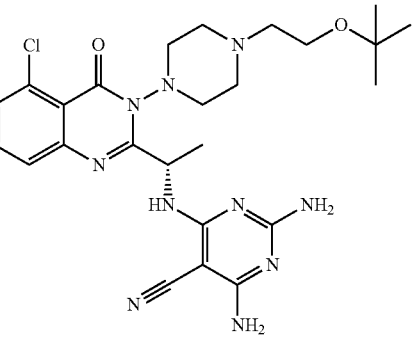 |
| 97 | 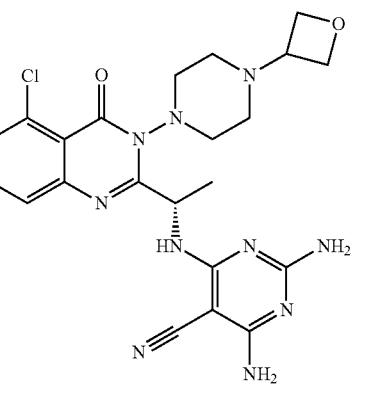 |

TABLE 1-continued
Representative Compounds
| Compound | Structure |
|---|---|
| 98 | 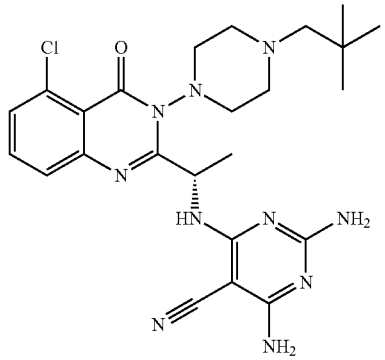 [SMILES: C[C@H](Nc1nc(N)nc(N)c1C#N)c1nc2cccc(Cl)c2c(=O)n1N1CCN(CC(C)(C)C)CC1] |
| 99 | 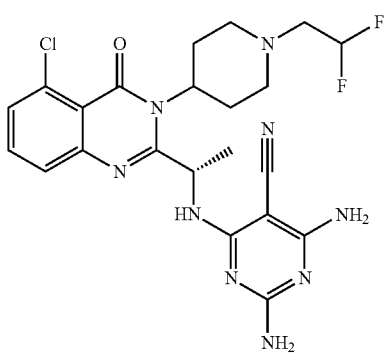 [SMILES: C[C@H](Nc1nc(N)nc(N)c1C#N)c1nc2cccc(Cl)c2c(=O)n1C1CCN(CC(F)F)CC1] |
| 100 | 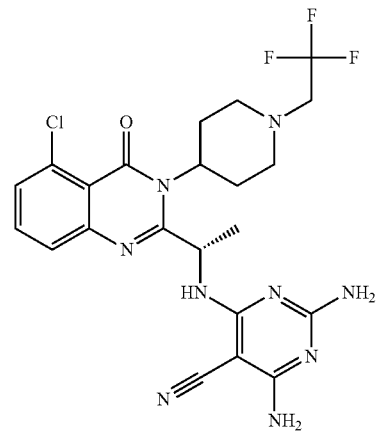 [SMILES: C[C@H](Nc1nc(N)nc(N)c1C#N)c1nc2cccc(Cl)c2c(=O)n1C1CCN(CC(F)(F)F)CC1] |
| 101 | 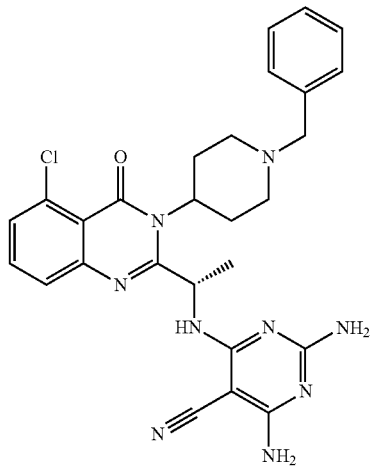 [SMILES: C[C@H](Nc1nc(N)nc(N)c1C#N)c1nc2cccc(Cl)c2c(=O)n1C1CCN(Cc2ccccc2)CC1] |
| 102 | 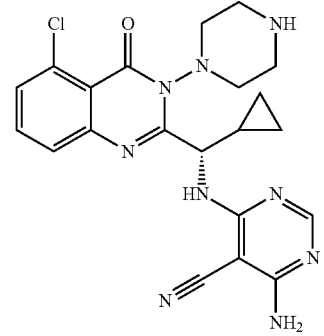 [SMILES: N#Cc1c(N)ncnc1N[C@H](c1nc2cccc(Cl)c2c(=O)n1N1CCNCC1)C1CC1] |
| 103 |  |

TABLE 1-continued

Representative Compounds

| Compound | Structure |
|---|---|
| 104 | 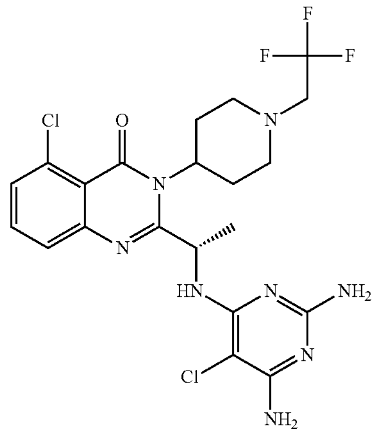 [SMILES: C[C@H](Nc1nc(N)nc(N)c1Cl)c1nc2cccc(Cl)c2c(=O)n1C1CCN(CC(F)(F)F)CC1] |
| 105 | 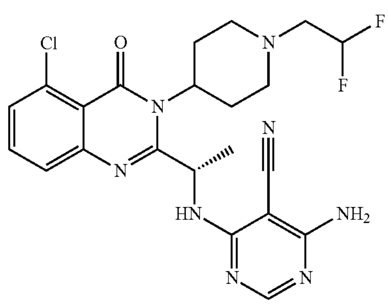 [SMILES: C[C@H](Nc1ncnc(N)c1C#N)c1nc2cccc(Cl)c2c(=O)n1C1CCN(CC(F)F)CC1] |
| 106 | 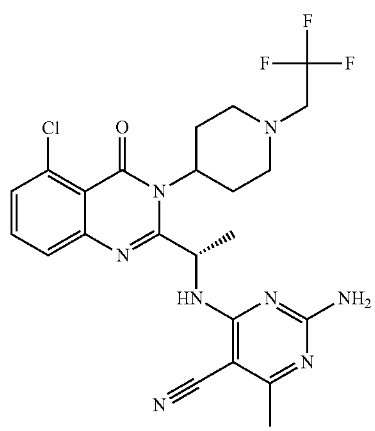 [SMILES: Cc1nc(N)nc(N[C@@H](C)c2nc3cccc(Cl)c3c(=O)n2C2CCN(CC(F)(F)F)CC2)c1C#N] |
| 107 | 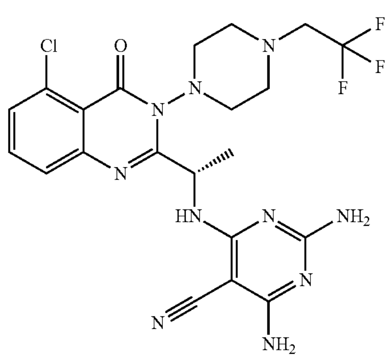 [SMILES: C[C@H](Nc1nc(N)nc(N)c1C#N)c1nc2cccc(Cl)c2c(=O)n1N1CCN(CC(F)(F)F)CC1] |
| 108 | |
| 109 | |
| 110 | |
| 111 | |

TABLE 1-continued

Representative Compounds

| Compound | Structure |
|---|---|
| 112 | 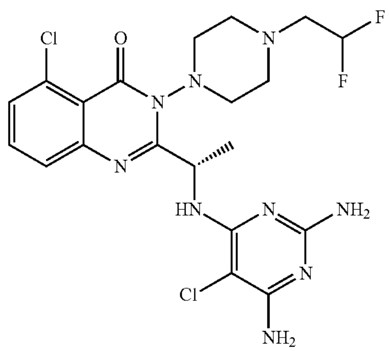 [SMILES: C[C@H](Nc1nc(N)nc(N)c1Cl)c1nc2cccc(Cl)c2c(=O)n1N1CCN(CC(F)F)CC1] |
| 113 | 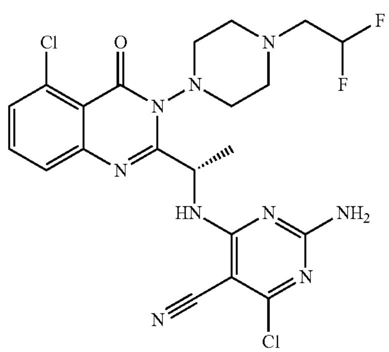 [SMILES: C[C@H](Nc1nc(N)nc(Cl)c1C#N)c1nc2cccc(Cl)c2c(=O)n1N1CCN(CC(F)F)CC1] |
| 114 | 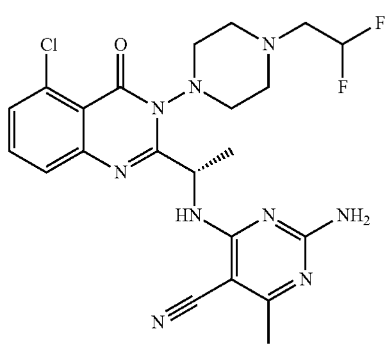 [SMILES: Cc1nc(N)nc(N[C@@H](C)c2nc3cccc(Cl)c3c(=O)n2N2CCN(CC(F)F)CC2)c1C#N] |
| 115 | 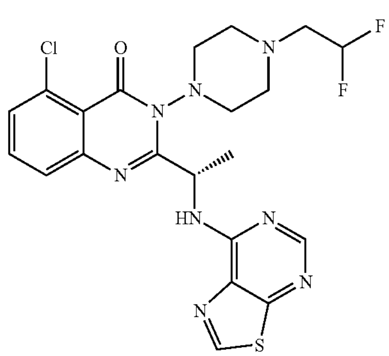 [SMILES: C[C@H](Nc1ncnc2scnc12)c1nc2cccc(Cl)c2c(=O)n1N1CCN(CC(F)F)CC1] |
| 116 | |
| 117 | |
| 118 | |
| 119 | |

TABLE 1-continued
Representative Compounds
| Compound | Structure |
|---|---|
| 120 | 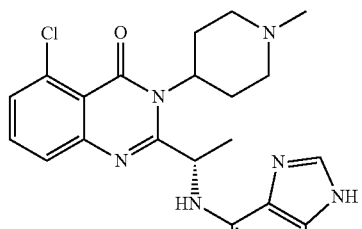 |
TABLE 1a
Representative Compounds
| Compound | Structure |
|---|---|
| 121 | 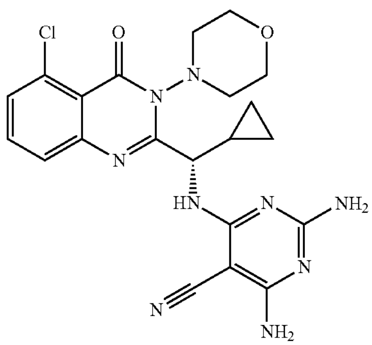 [SMILES: N#Cc1c(N)nc(N)nc1N[C@H](c1nc2cccc(Cl)c2c(=O)n1N1CCOCC1)C1CC1] |
| 122 | 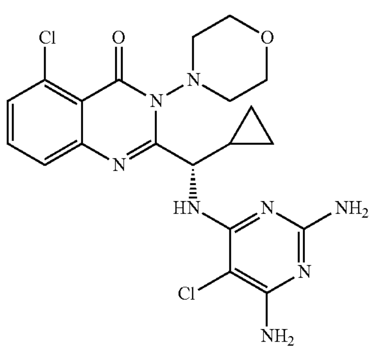 [SMILES: Nc1nc(N)c(Cl)c(N[C@H](c2nc3cccc(Cl)c3c(=O)n2N2CCOCC2)C2CC2)n1] |
| 124 | 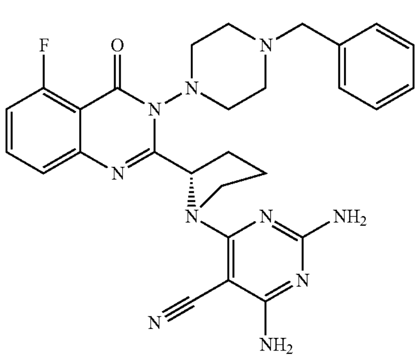 |
TABLE 1a-continued
Representative Compounds
| Compound | Structure |
|---|---|
| 125 | 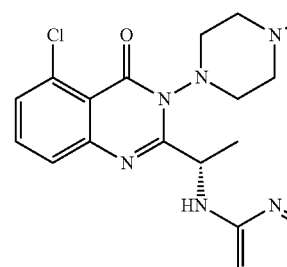 |
| 126 | 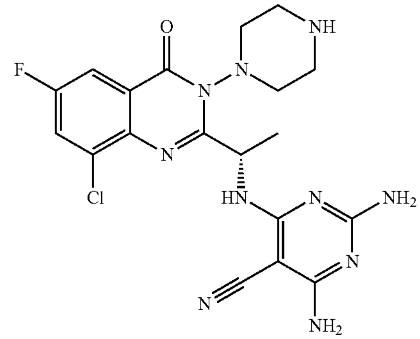 [SMILES: C[C@H](Nc1nc(N)nc(N)c1C#N)c1nc2c(Cl)cc(F)cc2c(=O)n1N1CCNCC1] |
| 127 | 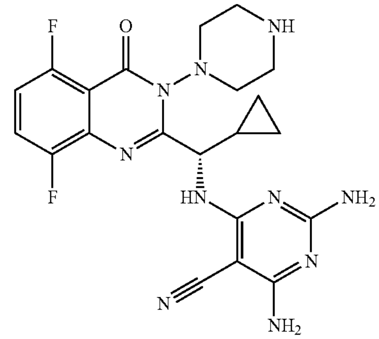 |
| 128 | 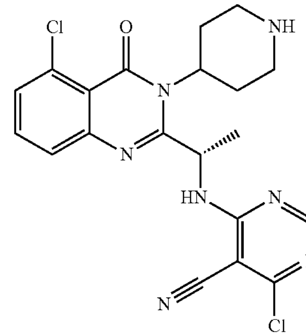 |

TABLE 1a-continued

Representative Compounds

| Compound | Structure |
|---|---|
| 129 | 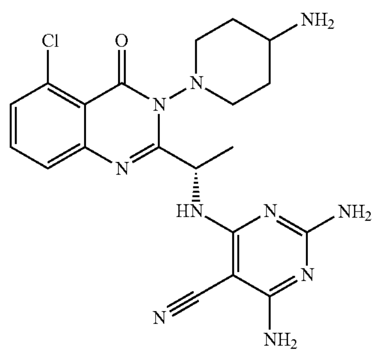 [SMILES: C[C@H](Nc1nc(N)nc(N)c1C#N)c1nc2cccc(Cl)c2c(=O)n1N1CCC(N)CC1] |
| 130 | 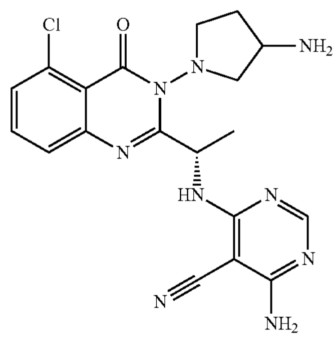 [SMILES: C[C@H](Nc1ncnc(N)c1C#N)c1nc2cccc(Cl)c2c(=O)n1N1CCC(N)C1] |
| 131 | 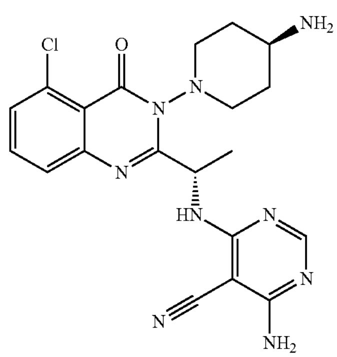 |
| 132 | 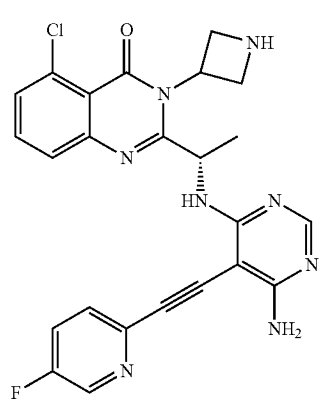 [SMILES: C[C@H](Nc1ncnc(N)c1C#Cc1ccc(F)cn1)c1nc2cccc(Cl)c2c(=O)n1C1CNC1] |
| 133 | |
| 134 | |
| 135 | |
| 136 | |

TABLE 1a-continued

Representative Compounds

| Compound | Structure |
|---|---|
| 137 | 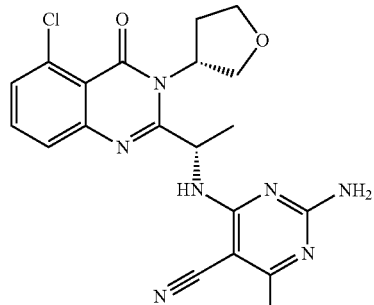 |

The present application provides pharmaceutically acceptable salts, hydrates, solvates, isomers, tautomers, stereoisomers, enantiomers, racemates, atropisomers, polymorphs, prodrugs, or a mixture thereof, of the compounds described herein. In addition, the present application provides the compounds in which from 1 to n hydrogen atoms attached to a carbon atom may be replaced by a deuterium atom or D, in which n is the number of hydrogen atoms in the molecule. It is known that the deuterium atom is a non-radioactive isotope of the hydrogen atom. Such compounds may increase resistance to metabolism, and thus may be useful for increasing the half-life of the compounds of any of the formulae described herein or pharmaceutically acceptable salts, isomers, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The terms "a compound of the present application," "a compound described herein," "a compound of any of the formulae described herein," or variant thereof refer to a compound having the structure of any of the formulae (J), (I), (II), (IIa), (IIb), (IIc), (IId), (III), (IIIa), (IIIb), (IIIc), (IIId), (IV), (IVa), (IVb), (IVc), (IVd), (IVe), (V), (Va), and (VI). In some embodiments, compounds of the present application are Compounds 1-138 as described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources. If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

"Isomers" refers to compounds that have the same molecular formula. As used herein, the term isomers include double bond isomers, racemates, stereoisomers, enantiomers, diastereomers, and atropisomers. Single isomers, such as enantiomers or diastereomers, can be obtained by asymmetric synthesis or by resolution of a mixture of isomers. Resolution of a mixture of isomers (e.g. racemates) maybe accomplished, for example, by conventional methods such as crystallization in the presence of a resolving agent, or chromatography, using, for example a chiral high pressure liquid chromatography (HPLC) column "Double bond isomers" refer to Z- and E-forms (or cis- and trans-forms) of the compounds with carbon-carbon double bonds.

"Atropisomers" refers to conformational stereoisomers which occur when rotation about a single bond in the molecule is prevented, or greatly hindered, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers may be separated by the methods well known in the art. Unless otherwise indicated, the description is intended to include individual atropisomers as well as mixtures. Also, as understood by those skilled in the art, the atropisomers may be represented by the same chemical name with different atropisomer designations. By way of example, the below structures, compound 66 and 67, (S)-4-amino-6-((1-(5-chloro-3-(1,4-diazepan-1-yl)-4-oxo-3,4-dihydroquinazolin-2-yl)ethyl)amino)pyrimidine-5-carbonitrile are atropisomers.

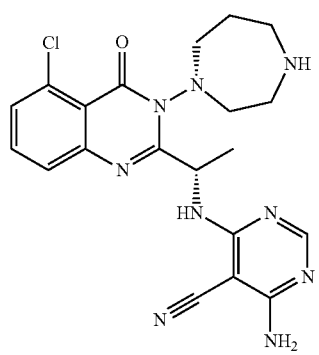

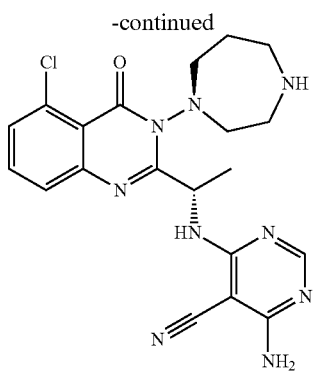

"Racemates" refers to a mixture of enantiomers.

"Stereoisomers" or "stereoisomeric forms" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomers" or "tautomeric formers" refer to alternate forms of a compound that differ in the position of a proton, such as enol-keto and imine-enamine tautomers, or heteroaryls such as pyrazoles, imidazoles, benzimidazoles, triazoles, and tetrazoles.

A "solvate" is formed by the interaction of a solvent and a compound. Solvates of salts of the compounds of any of the formulae described herein are also provided. Hydrates of the compounds of any of the formulae are also provided.

A "prodrug" is defined in the pharmaceutical field as a biologically inactive derivative of a drug that upon administration to the human body is converted to the biologically active parent drug according to some chemical or enzymatic pathway.

In any one of the foregoing embodiments, the compound described herein or a pharmaceutically acceptable salt thereof is an (S)-enantiomer. In any one of the foregoing embodiments, the compound described herein or a pharmaceutically acceptable salt thereof is an (R)-enantiomer. In any one of the foregoing embodiments, the compound described herein or a pharmaceutically acceptable salt thereof is an atropisomer.

The application also provides a composition containing a mixture of enantiomers of the compound or a pharmaceutically acceptable salt thereof. In one embodiment, the mixture is a racemic mixture. In other embodiments, the composition comprises the (S)-enantiomer of a compound in excess of over the corresponding the (R)-enantiomer of the compound. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound according to any of the formulae described herein, or a pharmaceutically acceptable salt thereof, may also contain the compound in enantiomeric excess (e.e.). By way of example, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%.

In any one of the foregoing embodiments, the compound or a pharmaceutically acceptable salt thereof, is an atropisomer. Another embodiment provides the composition containing a mixture of atropisomers of the compound or a pharmaceutically acceptable salt thereof. By way of example, a compound with 95% of one atropisomer and 5% of the other atropisomers. In some embodiments, a compound with about 90, 80, 70, 60, 50, 40, 30, 20, or 10% of one atropisomer and 10, 20, 30, 40, 50, 60, 70, 80, or 90%, respectively, of the other atropisomers.

The application also provides the free base forms of the compounds described herein. In certain embodiments, provided herein are the enantiomers, (R) or (S), of the compounds of the formulae described herein. In other embodiments, provided herein are the atropisomers of the compounds of the formulae described herein.

The application further provides compositions comprising the compounds described herein or a pharmaceutically acceptable salt, isomer, prodrug, or solvate thereof. The composition may include racemic mixtures, mixtures containing an enantiomeric excess of one enantiomer or single diastereomers or diastereomeric mixtures. All such isomeric forms of these compounds are expressly included herein, the same as if each and every isomeric form were specifically and individually listed.

In certain embodiments, provided herein are also polymorphs, such as crystalline and amorphous forms, of the compounds described herein. In some embodiments, provided are also chelates, non-covalent complexes, and mixtures thereof, of the compounds of the formula described herein or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds of the formulae described herein or a pharmaceutically acceptable salt, isomer, prodrug, or solvate thereof may be used for the treatment of diseases and/or conditions mediated by PI3K isoforms. In addition, the application provides the compounds for use in therapy. Also, provided herein are methods for inhibiting one or more PI3K isoforms. In one embodiment, provided are methods for inhibiting PI3Kδ activity using the compound described herein or a pharmaceutically acceptable salt, isomer, prodrug, or solvate thereof. In other embodiment, provided are methods for inhibiting PI3Kδ and/or PI3Kβ activities using the compound or a pharmaceutically acceptable salt, isomer, prodrug, or solvate thereof. The application further provides methods for use in such methods. The PI3K isoforms may be selectively or specifically inhibited. Additionally, the compounds may be used to inhibit PI3K activity therapeutically or prophylactically, such as PI3Kδ and/or PI3Kβ.

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof. In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Auroa kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or C1(2) inhibitor, a DDR (discoidin domain receptor, including DDR1 and/or DDR2) inhibitor, a EGFR inhibitor, a FXR (farnesoid x receptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (1-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXL5) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L1 (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2, TLR-3, TLR-4, TLR-5, TLR-6, TLR-7, TLR-8, TLR-9, TLR-10, TLR-11, TLR-12, and/or TLR-13) inhibitor, a TK (tyrosine kinase) inhibitor, a TPL2 (serine/threonine kinase) inhibitor, a NEK9 inhibitor, an Abl inhibitor, a p38 kinase inhibitor, a PYK inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the JAK inhibitor is N-(cyanomethyl)-4-[2-(4-morpholinoanilino)pyrimidin-4-yl]benzamide as named by ChemDraw (may also be referred to as CYT0387 or momelotinib) and may be synthesized by the methods described in U.S. Pat. No. 8,486,941. In certain embodiment, the SyK inhibitor is 6-(1H-indazol-6-yl)-N-(4-morpholinophenyl)imidazo[1,2-a]pyrazin-8-amine as named by ChemDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amino-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, Pseudomonas exotoxin, Bordetella pertussis adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammall and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycins, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK®; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL® and docetaxel (TAXOTERE®); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproternase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, obinutuzumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents include aldesleukin, alvocidib, antineoplaston AS2-1, antineoplaston A10, antithymocyte globulin, amifostine trihydrate, aminocamptothecin, arsenic trioxide, beta alethine, Bcl-2 family protein inhibitor ABT-263, ABT-199, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the methods include administering a compound of the formula described herein or a pharmaceutically acceptable salt, isomer, prodrug, or solvate thereof, in a therapeutically effective amount to a human in need thereof. The method can be employed to treat a patient who has or is believed to have a disease or condition whose symptoms or pathology is mediated by expression or activity of PI3Kβ and/or PI3Kδ. The patient may be a mammal or a human. In certain embodiment, the patient may be a human.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing the effect of another medication, delaying the progression of the disease, increasing the quality of life, and/or prolonging survival.

"Prevention" or "preventing" mean any treatment of a disease or condition that causes the clinical symptoms of the disease or condition not to develop. Compounds may, in some embodiments, be administered to a subject (including a human) who is at risk or has a family history of the disease or condition.

"Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases, or disorders, or conditions that would benefit from certain treatment; for example, being treated with the PI3K inhibitor of the compounds according to the present application. In certain embodiments, the subject may be a human who (i) has not received any treatment including chemotherapy treatment, (ii) is substantially refractory to at least one chemotherapy treatment, (iii) is in relapse after treatment with chemotherapy, or both (i) and (ii). In some of embodiments, the subject is refractory to at least one, at least two, at least three, or at least four chemotherapy treatments (including standard or experimental chemotherapies).

The terms "therapeutically effective amount" or "effective amount" of a compound of the present application or a pharmaceutically acceptable salt, isomers, prodrug, or solvate thereof, mean an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ and PI3Kβ activity. The therapeutically effective amount may vary depending on the subject, and disease or condition being treated, the weight and age of the subject, the severity of the disease or condition, and the manner of administering, which can readily be determined by one or ordinary skill in the art.

In addition to the therapeutic uses, the compounds described herein have the selectivity or selective inhibition to certain PI3K isoforms. In one embodiment, the compounds have selectivity to PI3Kβ. In some embodiments, the compounds have selectivity to PI3Kδ. In yet other embodiments, the compounds have selectivity to PI3Kβ and PI3Kδ. The selectivity to PI3K isoforms may be determined by measuring the compound's activity in inhibiting certain PI3K isoforms using the assay described in the example below or the methods commonly used. It is understood that the conditions (e.g. the reagent concentration or the incubation temperature) may be varied and the results of the assay may vary. In some instances, the value may vary within a range of one to three-folds.

The term "inhibition" indicates a decrease in the baseline activity of a biological activity or process. The term "inhibition of activity of PI3K isoforms" or variants thereof refer to a decrease in activity in any PI3K isoform (e.g., alpha, beta, gamma, or delta) as a direct or indirect response to the presence of a compound of any of the formula described herein relative to the activity of PI3K isoform in the absence of such compound "Inhibition of PI3Kδ and/or PI3Kβ activities" or variants thereof refer to a decrease in PI3Kδ and/or PI3Kβ activities as a direct or indirect response to the presence of the compounds described herein, relative to the activities of PI3Kδ and/or PI3Kβ in the absence of such compound. In some embodiments, the inhibition of PI3K isoform activities may be compared in the same subject prior to treatment, or other subjects not receiving the treatment.

Without being bound to any theory, the decrease in the activity of PI3K may be due to the direct interaction of the compound with PI3K, or due to the interaction of the compounds described herein with one or more other factors that affect PI3K activity. For example, the presence of the compounds may decrease the activities of PI3Kδ and/or PI3Kβ by directly binding to PI3Kδ and/or PI3Kβ, by causing (directly or indirectly) another factor to decrease PI3Kδ and/or PI3Kβ activities, or by (directly or indirectly) decreasing the amount of PI3Kδ and/or PI3Kβ present in the cell or organism.

The term "PI3K inhibitor" or variant thereof refers to a compound that inhibits the activity of PI3K. The term "PI3K isoform selective inhibitor" or variant thereof refers to a compound that inhibits the activity of one or more PI3K isoforms more effectively than the other remaining PI3K isoforms. By way of example, the term "PI3Kβ selective inhibitor" generally refers to a compound that inhibits the activity of the PI3Kβ isoform more effectively than other isoforms of the PI3K family, and the term "PI3Kδ selective inhibitor" generally refers to a compound that inhibits the activity of the PI3Kδ isoform more effectively than other isoforms of the PI3K family. The term "dual PI3Kδ/β selective inhibitor" generally refers to a compound that inhibits the activity of both PI3Kδ and PI3Kβ isoforms more effectively than other isoforms of the PI3K family (e.g., PI3Kα or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the compound concentration that inhibits 50% of the activity in a biochemical assay, i.e., the 50% inhibitory concentration or "$IC_{50}$". The determination of $IC_{50}$ values can be accomplished using conventional techniques known in the art, including the techniques described in the Examples below. In general, an $IC_{50}$ can be determined by measuring the activity of a given enzyme in the presence of a range of concentrations of the compound under the study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

According to the present application, a PI3Kβ selective inhibitor is a compound that exhibits a 50% inhibitory concentration ($IC_{50}$) with respect to PI3Kβ that is at least 10-fold, at least 20-fold, at least 30-fold, at least 50-fold, at least 100-fold, at least 200-fold, or at least 500-fold lower than the $IC_{50}$ with respect to either PI3Kα or PI3Kγ or both PI3Kα and PI3Kγ. In addition, a PI3Kδ/β selective inhibitor is a compound that exhibits a 50% inhibitory concentration ($IC_{50}$) with respect to PI3Kβ and PI3Kδ that is at least 10-fold, at least 20-fold, at least 30-fold, at least 50-fold, at least 75-fold, at least 100-fold, at least 200-fold, and at least 500-fold lower than the $IC_{50}$ with respect to either PI3Kα or PI3Kγ. The dual PI3Kδ/β selective inhibitor may have the same or similar $IC_{50}$ to both PI3Kδ and PI3Kβ or may have different $IC_{50}$ to either PI3Kδ or PI3Kβ. As used herein, the term "potency," "potent," or variants thereof refer to the compound exhibiting an $IC_{50}$ value that is less than 100 nM. When comparing two compounds, the compound that exhibits a lower $IC_{50}$ value is referred to as a more potent inhibitor.

The compounds of the present application exhibit unexpected selectivity to PI3Kβ. As shown in the example, certain compounds in Table 1 exhibit low $IC_{50}$ values (e.g. 1 to 100 nM) to both PI3Kβ and PI3Kδ. Certain compounds in Table 1a also exhibited such selectivity to PI3K isoforms. Also, certain compounds of the present application exhibited at least between 10-fold to 400-fold lower $IC_{50}$ values for PI3Kβ than PI3Kγ, suggesting the compounds exhibit more selectivity to PI3Kβ compared to PI3Kγ(i.e., inhibits the activity of the PI3Kβ isoform more effectively than the PI3Kγ isoform as shown by the PI3Kγ/PI3Kβ ratio). Moreover, the compounds described herein exhibit selectivity to both PI3Kβ and PI3δ. The compound of (S)-2,4-diamino-6-((1-(5-chloro-4-oxo-3-phenyl-3,4-dihydroquinazolin-2-yl)ethyl)amino)pyrimidine-5-carbonitrile, described in U.S. Provisional Application No. 61/745,437, exhibited less selectivity to PI3Kγ (e.g. the PI3Kγ/PI3Kβ ratio is less than 1-fold). The results of the present application suggest that certain compounds described herein are dual selective inhibitors of PI3Kδ and PI3Kβ and exhibit more selectivity to PI3Kβ compared to PI3Kγ. All of patents and patent publications disclosed in the present application are incorporated herein by reference in their entireties.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, it may be used ex vivo to determine the optimal schedule and/or dosing of administration of a PI3K selective inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The compounds of the formula described herein or a pharmaceutically acceptable salt, prodrug, or solvate thereof, may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Also, PI3Kβ is generally mis-regulated in certain cancer cells. Aberrant proliferation of cells often interferes with normal tissue function, which may result in abnormal cellular response such as immunity, inflammation, and/or apoptosis. The selective inhibitors to PI3Kδ and/or PI3Kβ are useful in treating, inhibiting, or preventing aberrant proliferation of cancerous and/or hematopoietic cells and ameliorating the symptoms and secondary conditions.

The compounds described herein may be used to treat subjects having various disease states, disorders, and conditions (also collectively referred to as "indications") associated with PI3K isoforms or their activities. As used herein, the terms "diseases," "disorders," "conditions" are used interchangeably. Such indications may include, for example, cancer, including hematologic malignancies (e.g. leukemias and lymphomas, myeloproliferative disorders, myelodysplastic syndromes, plasma cell neoplasms) and solid tumors, inflammation, fibrosis, allergic conditions (including hypersensitivity), cardiovascular diseases, neurodegenerative diseases, renal disorders, viral infections, obesity, and autoimmune diseases.

In other embodiments, the compounds described herein may be used to treat cancers that are mediated by, dependent on, or associated with PI3K activity. In certain embodiments, the disease or condition is an autoimmune disease, an inflammatory disease, or a cancer. In some embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors.

In other embodiments, the disease is a solid tumor. By way of examples, the solid tumor includes but is not limited to pancreatic cancer, bladder cancer, colorectal cancer, breast cancer, prostate cancer, renal cancer, hepatocellular cancer, lung cancer, ovarian cancer, cervical cancer, rectum cancer, liver cancer, kidney cancer, stomach cancer, skin cancer, gastric cancer, esophageal cancer, head and neck cancer, melanoma, neuroendocrine cancers, CNS cancers (e.g., neuroblastoma), brain tumors (e.g., glioma, anaplastic oligodendroglioma, adult glioblastoma multiforme, and adult anaplastic astrocytoma), bone cancer, or soft tissue sarcoma. In some embodiments, the solid tumor is non-small cell lung cancer, small-cell lung cancer, colon cancer, CNS cancer, melanoma, ovarian cancer, renal cancer, pancreatic cancer, prostate cancer, or breast cancer.

The present application also provides a method for treating a human in need thereof, who has or is suspected of having a disease or condition responsive or believed to be responsive to the inhibition of PI3Kδ and/or PI3Kβ activity by administering to the subject a compound of the formulae described herein or a pharmaceutically acceptable salt, enantiomer, atropisomer, tautomer, prodrug, or solvate thereof.

Additionally, the application provides a method of inhibiting kinase activity of a PI3Kδ and/or PI3Kβ polypeptides by contacting the polypeptides with a compound of the formulae described herein or a pharmaceutically acceptable salt, isomer, prodrug, solvate, or a mixture thereof.

Moreover, the application provides a method of decreasing cell viability, increasing cell death or apoptosis, increasing interference with PI3K signaling pathways (including AKT, S6RP, ERK phosphorylation), and/or reduction in chemokine production with an effective amount of a compound of any of the formulae described herein or a pharmaceutically acceptable salt, isomer, prodrug, solvate, or a mixture thereof.

The application further provides a method of disrupting leukocyte function comprising contacting the leukocytes with an effective amount of a compound of any of the formulae described herein or a pharmaceutically acceptable salt, isomer, prodrug, solvate, or a mixture thereof, in a human in need thereof.

Provided is also a method of inhibiting growth or proliferation of cancer cells comprising contacting the cancer cells with an effective amount of a compound of the formulae described herein or a pharmaceutically acceptable salt, isomer, prodrug, solvate, or a mixture thereof.

Kits

Provided herein are also kits that include a compound of the formulae of the present application or a pharmaceutically acceptable salt, isomer, prodrug, or solvate thereof and suitable packaging. In one embodiment, a kit further includes instructions for use. In one aspect, a kit includes a compound of the formulae described herein or a pharmaceutically acceptable salt, isomer, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, isomer, prodrug, or solvate thereof, in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds of any of the formulae disclosed herein or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders. In certain embodiments, the pharmaceutical composition is in the form of tablets.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, isomer, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 100 to 150 mg/day, between about 1 to 100 mg/day, between about between about 1 to 50 mg/day, between about 50 to 100 mg/day, between about 100 to 125 mg/day, between about 100 to 150 mg/day, between about 100 to 175 mg/day, between about 100 to 200 mg/day, between about 100 to 225 mg/day, between about 100 to 250 mg/day, between about 100 to 350 mg/day, between about 100 to 400 mg/day, between about 100 to 450 mg/day, or between about 100 to 500 mg/day.

When administered orally, the total daily dosage for a human subject may be between 1 mg and 1,000 mg/day, between about 1 to 100 mg/day, between about 1 to 50 mg/day, between about 50 to 100 mg/day, between 100 to 200 mg/day, between about 200 to 300 mg/day, between about 300 to 400 mg/day, between about 400 to 500 mg/day, between about 100 to 150 mg/day, between about 150 to 200 mg/day, between about 200 to 250 mg/day, between about 75 to 150 mg/day, or between about 150 to 300 mg/day.

The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. In some treatment, the compound or the composition thereof is administered continuously, i.e. every day. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of the above formula and increasing the dose by increments until clinical efficacy is achieved. Increments of about 1, 5, 10, 25, 50, 75, or 100 mg can be used to increase the dose. The dosage can be increased daily, every other day, twice per week, or once per week.

Synthesis of the Compounds

The compounds of the present application may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The compounds of formula (I) may be prepared using the method shown in Reaction Scheme I.

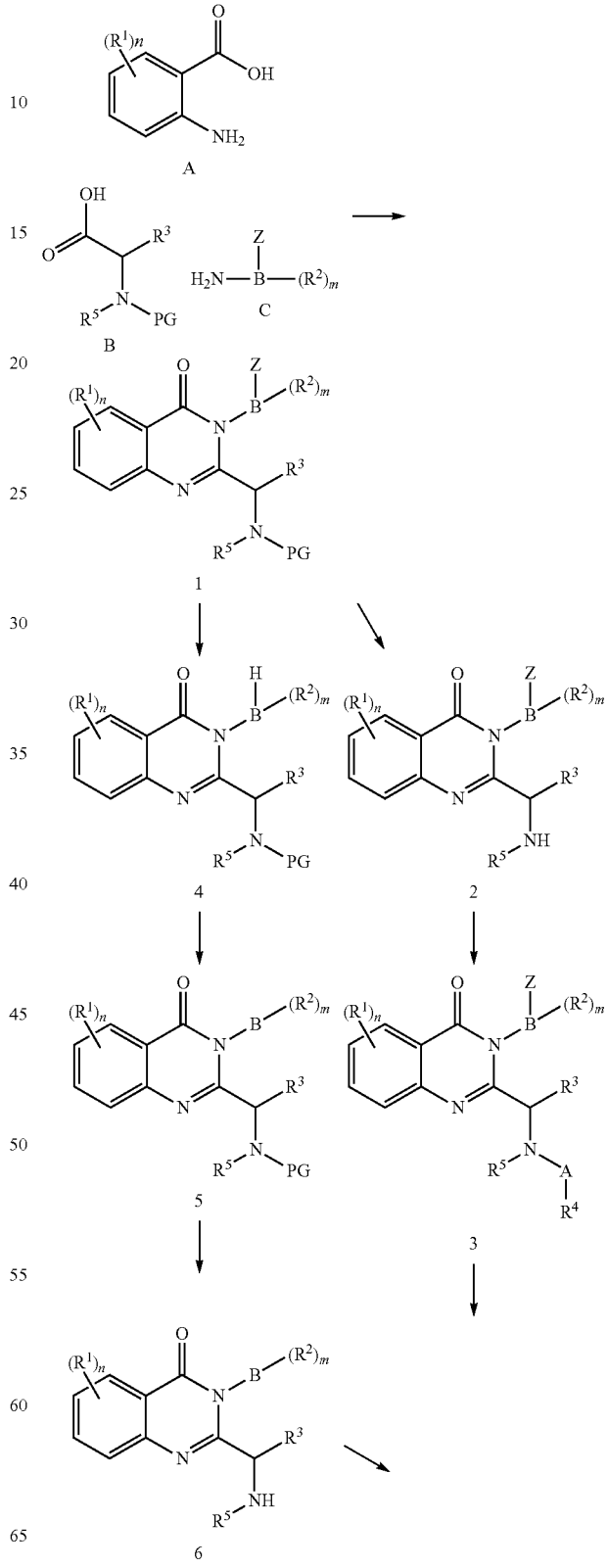

Reaction Scheme I

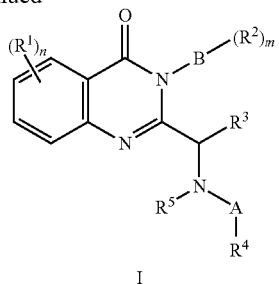

I

Preparation of a Compound of Formula (1)

The compound of formula (1) can be made by combining compounds (A), (B) and (C) in the presence of a dehydrating agent. PG may be a protecting group such as t-butoxycarbonyl (Boc) or fluorenylmethoxycarbonyl (Fmoc). Compounds (A), (B) and (C) are commercially available or can be made by the methods that are commonly known or used by one skilled in the art. B, $R^1$, $R^2$, $R^3$, and $R^5$ are defined herein. B' is B or a group that may be converted to B by chemical transformation as described herein, in which case B'—Z is B and Z is a protecting group such as Boc or Fmoc if further manipulation is necessary. Compound (A) is mixed with Compound (B) in the presence of a coupling agent such as diphenyl phosphite in a solvent such as pyridine. After stirring at a temperature between ambient and 100° C. for 1 to 5 hours, compound (C) is added. The mixture is further stirred at a temperature between ambient and 100° C. for 5 to 24 hours and cooled to room temperature. To extract the compound of formula (1), an organic solvent such as ethyl acetate (EtOAc) is added. Then the reaction is washed with mild acid, water, and brine. The organic phase is concentrated to obtain the compound of formula (1). The compound of formula (1) is purified by any suitable methods known in the art, such as chromatography on silica gel. Alternatively, the compound of formula (1) is purified directly without an aqueous work-up. Alternatively, the compound of formula (1) is used in the next step without purification.

Preparation of a Compound of Formula (2)

The compound of formula (2) can be made by removing the protecting group(s) from the compound of formula (1). Different conditions will be used depending on the protecting group being utilized. If it is desired to remove a Boc group, the compound of formula (1) is dissolved in a suitable solvent and treated with a suitable acid. By way of example, suitable solvents include dichloromethane or dioxane, and suitable acids include trifluoroacetic acid, hydrochloric acid, or boron tribromide ($BBr_3$). The reaction is carried out at temperatures between −78° C. to ambient temperature. After the reaction is complete, solvent is removed to obtain the compound of formula (2). If it is desired to remove an Fmoc group the compound of formula (1) is dissolved in a suitable solvent and treated with a suitable base. By way of example, suitable solvents include dichloromethane or DMF, and suitable bases include piperidine. The reaction is carried out at temperatures between 0° C. to 50° C. for between 0.5 and 24 hours. After the reaction is complete, the reaction may be diluted with water and a suitable solvent for extraction such as EtOAc or dichloromethane. The solvent is removed to obtain the compound of formula (2) and used without further purification or purified via methods known, such as chromatography.

Preparation of a Compound of Formula (3) and (I)

The compound of formula (3) can generally be prepared by coupling compound of formula (2) and an appropriately substituted $R^4$—X, where X is a halo, in the presence of a suitable base in a suitable solvent. An example of a suitable base is diisopropylethylamine, triethylamine or N-methylmorpholine. An example of a suitable solvent is N-methylpyrrolidone (NMP), DMF, DMSO, or isopropanol. Also, an additive such as potassium fluoride may be used. The reaction is typically performed at a temperature between 50° C. to 150° C. for about 30 minutes to 24 hours. Alternatively the reaction can be performed in a microwave at a temperature between 100° C. to 150° C. for about 30 minutes to 24 hours. In instances where Z is $R^2$, this step will result in compounds of formula (I). The compound of formula (3) may also be prepared by coupling a compound of formula (2) with a suitable acid in the presence of a coupling agent, such as HATU, DCC, or carbonyl diimidazole in the presence of a base such as triethylamine or diisopropylethylamine in a suitable solvent such as dichloromethane or THF. Water can be added to quench the reaction upon completion, and the precipitate may be filtered then dissolved in an organic solvent such as dichloromethane (DCM). Alternatively the reaction may be isolated by dilution with an inert organic solvent such as EtOAc of dichloromethane, followed by an aqueous work-up. The product can be isolated by methods known in the art, for example by removal of solvent under reduced pressure. The product can be purified using any suitable methods known in the art, for example, recrystallization, precipitation, or chromatography of the residue. In some instances this step will result in compounds of formula (I). If the compound of formula (3) contains a BOC group, the Boc group may be removed by methods known to one of skill in the art and described above in step 2 to give compounds of formula (I) where $R^2$ is H.

Preparation of a Compound of Formula (4)

The compound of formula (4), in which Z is Boc, can be made by removing the protecting group(s) from the compound of formula (1). The compound of formula (1) is dissolved in a suitable solvent and treated with a suitable acid. By way of example, suitable solvents include dichloromethane or dioxane, and suitable acids include trifluoroacetic acid, hydrochloric acid, or boron tribromide ($BBr_3$). The reaction is carried out at temperatures between −78° C. to ambient temperature. After the reaction is complete, solvent is removed to obtain the compound of formula (4).

Preparation of a Compound of Formula (5)

The compound of formula (5) can be made by methods known to one of skill in the art, such as reaction of the compound of formula (4) with an acid and a coupling agent, such as HATU, as described above. Furthermore, the amine may be alkylated by methods known to one of skill in the art through the reaction of the amine with an aldehyde or ketone containing compound in the presence of a reducing agent, such as $NaCNBH_3$ or sodium triacetoxyborohydride, in a suitable solvent such as methanol or dichloromethane. After the reaction is complete, the reaction may be diluted with water and a suitable solvent for extraction such as EtOAc or dichloromethane. The solvent is removed to obtain the compound of formula (5) and used without further purification or purified via methods known, such as chromatography.

Preparation of a Compound of Formula (6)

The compound of formula (6) can be made by removing the protecting group(s) from the compound of formula (5) in which the protecting group is Fmoc. The compound of formula (5) is dissolved in a suitable solvent and treated with a suitable base. By way of example, suitable solvents include dichloromethane or DMF, and suitable bases include piperidine. The reaction is carried out at temperatures between 0° C. to 50° C. for between 0.5 and 24 hours. After the reaction is complete, the reaction may be diluted with water and a suitable solvent for extraction such as EtOAc or dichloromethane. The solvent is removed to obtain the compound of formula (6) and used without further purification or purified via methods known, such as chromatography.

It should be understood that the compounds of formula (I) can be prepared according to the methods provided in Reaction Scheme 1, starting from materials known to one of skill in the art.

After synthesis, the compounds may be isolated in the form of a free base or a trifluoroacetic acid salt and further characterized by NMR. The resulting compounds and their NMR characterizations may represent either the free base or salt form. The ratio of parent compound and corresponding salt is not determined.

Example 1. Preparation of a Compound of Formula (1)

A. Preparation of a Compound of Formula (1) wherein n is 1, R1 is chloro, m is 0, B is 4,7-diazaspiro[2,5]octanyl, Z is Boc, PG is Fmoc, R⁵ is H, and R³ is methyl

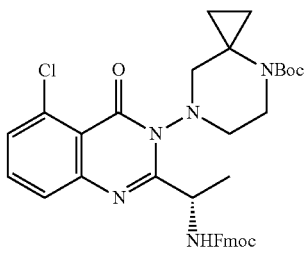

Diphenyl phosphite (2.8 mL, 15 mmol) was added to a solution of 2-amino-6-chlorobenzoic acid (449 mg, 2.6 mmol) and (S)-2-((((9H-fluoren-9-yl)methoxy)carbonyl) amino)propanoic acid (815 mg, 2.6 mmol) in pyridine (2.1 mL). The reaction mixture was stirred at 40° C. for 2 hours. tert-Butyl 7-amino-4,7-diazaspiro[2.5]octane-4-carboxylate (744 mg, 3.3 mmol) was added to the reaction mixture, which was stirred at 55° C. for 18 hours. The reaction mixture was cooled to room temperature and loaded onto a hexane primed SiO₂ column. The title compound was then purified by eluting with EtOAc in hexanes (0-50%) to afford (S)-tert-butyl 7-(2-(1-(((9H-fluoren-9-yl) methoxy)carbonylamino)ethyl)-5-chloro-4-oxoquinazolin-3(4H)-yl)-4,7-diazaspiro[2.5]octane-4-carboxylate. ES/MS m/z=656.3 (M+H⁺).

B. Preparation of the below compounds of Formula (1) using the methods described in Example 1A and the Reaction Scheme I:

tert-butyl 4-(2-((S)-1-((((9H-fluoren-9-yl)methoxy)carbonyl)amino)ethyl)-5-chloro-4-oxoquinazolin-3(4H)-yl)-2-(trifluoromethyl)piperazine-1-carboxylate;
(S)-tert-butyl 4-(2-(1-((((9H-fluoren-9-yl)methoxy)carbonyl)amino)ethyl)-5-chloro-4-oxoquinazolin-3(4H)-yl)-1,4-diazepane-1-carboxylate;
(S)-tert-butyl 4-(2-(1-((((9H-fluoren-9-yl)methoxy)carbonyl)amino)ethyl)-5-chloro-4-oxoquinazolin-3(4H)-yl) piperazine-1-carboxylate;
(S)-tert-butyl 4-(2-(1-((((9H-fluoren-9-yl)methoxy)carbonyl)amino)propyl)-5-chloro-4-oxoquinazolin-3(4H)-yl) piperazine-1-carboxylate;
(S)-tert-butyl 4-(2-(1-((((9H-fluoren-9-yl)methoxy)carbonyl)amino)-3-methylbutyl)-5-chloro-4-oxoquinazolin-3(4H)-yl)piperazine-1-carboxylate;
(S)-tert-butyl 4-(2-(1-((((9H-fluoren-9-yl)methoxy)carbonyl)amino)ethyl)-5,8-dichloro-4-oxoquinazolin-3(4H)-yl)piperazine-1-carboxylate;
(S)-tert-butyl 4-(2-(((((9H-fluoren-9-yl)methoxy)carbonyl)amino)(cyclopropyl)methyl)-5-chloro-4-oxoquinazolin-3(4H)-yl)piperazine-1-carboxylate;
tert-butyl 4-(2-((S)-1-((((9H-fluoren-9-yl)methoxy)carbonyl)amino)ethyl)-5-chloro-4-oxoquinazolin-3(4H)-yl) azepane-1-carboxylate;
(S)-tert-butyl (1-(5-chloro-3-(4-methylpiperazin-1-yl)-4-oxo-3,4-dihydroquinazolin-2-yl)ethyl)carbamate;
tert-butyl 3-(2-((S)-1-(((9H-fluoren-9-yl)methoxy)carbonylamino)ethyl)-5-chloro-4-oxoquinazolin-3(4H)-yl)piperidine-1-carboxylate;
tert-butyl 4-(2-((S)-1-(((9H-fluoren-9-yl)methoxy)carbonylamino)ethyl)-5-chloro-4-oxoquinazolin-3(4H)-yl) azepane-1-carboxylate;
tert-butyl 3-(2-((S)-1-(((9H-fluoren-9-yl)methoxy)carbonylamino)ethyl)-5-chloro-4-oxoquinazolin-3(4H)-yl)pyrrolidine-1-carboxylate;
tert-butyl 3-(2-((S)-1-(((9H-fluoren-9-yl)methoxy)carbonylamino)ethyl)-5-chloro-4-oxoquinazolin-3(4H)-yl)piperidine-1-carboxylate;
(S)-tert-butyl (1-(5-chloro-3-(1-methylpiperidin-4-yl)-4-oxo-3,4-dihydroquinazolin-2-yl)ethyl)carbamate;
(S)-tert-butyl 4-(2-(1-((((9H-fluoren-9-yl)methoxy)carbonyl)amino)ethyl)-5-methyl-4-oxoquinazolin-3(4H)-yl)piperidine-1-carboxylate;
tert-butyl ((1S)-1-(5-chloro-3-((1R,5S)-8-methyl-8-azabicyclo[3.2.1]octan-3-yl)-4-oxo-3,4-dihydroquinazolin-2-yl)ethyl)carbamate;
(S)-tert-butyl (1-(3-(4-benzylpiperazin-1-yl)-5-chloro-4-oxo-3,4-dihydroquinazolin-2-yl)ethyl)carbamate;
(S)-tert-butyl 4-(2-(1-((((9H-fluoren-9-yl)methoxy)carbonyl)amino)ethyl)-5-chloro-8-fluoro-4-oxoquinazolin-3(4H)-yl)piperazine-1-carboxylate;
(S)-tert-butyl 4-(2-(((((9H-fluoren-9-yl)methoxy)carbonyl)amino)(cyclopropyl)methyl)-5-chloro-8-fluoro-4-oxoquinazolin-3(4H)-yl)piperazine-1-carboxylate;
(S)-tert-butyl 4-(2-(1-((((9H-fluoren-9-yl)methoxy)carbonyl)amino)propyl)-5-chloro-8-fluoro-4-oxoquinazolin-3(4H)-yl)piperazine-1-carboxylate;
(S)-tert-butyl 4-(2-(((((9H-fluoren-9-yl)methoxy)carbonyl)amino)(cyclopropyl)methyl)-5,8-difluoro-4-oxoquinazolin-3(4H)-yl)piperazine-1-carboxylate;
(S)-tert-butyl 4-(2-(1-((((9H-fluoren-9-yl)methoxy)carbonyl)amino)ethyl)-5,8-difluoro-4-oxoquinazolin-3(4H)-yl)piperazine-1-carboxylate;
tert-butyl 4-(2-((S)-1-((((9H-fluoren-9-yl)methoxy)carbonyl)amino)ethyl)-5-chloro-4-oxoquinazolin-3(4H)-yl)-3,3-difluoropiperidine-1-carboxylate;
(S)-tert-butyl ((5-chloro-3-(4-methylpiperazin-1-yl)-4-oxo-3,4-dihydroquinazolin-2-yl)(cyclopropyl)methyl)carbamate;
(R)-tert-butyl 3-(2-((S)-1-((((9H-fluoren-9-yl)methoxy)carbonyl)amino)ethyl)-5-chloro-4-oxoquinazolin-3(4H)-yl) pyrrolidine-1-carboxylate;
(S)-tert-butyl 3-(2-((S)-1-((((9H-fluoren-9-yl)methoxy)carbonyl)amino)ethyl)-5-chloro-4-oxoquinazolin-3(4H)-yl) pyrrolidine-1-carboxylate;

tert-butyl 3-(2-((S)-1-((((9H-fluoren-9-yl)methoxy)carbonyl)amino)ethyl)-5-chloro-4-oxoquinazolin-3(4H)-yl)pyrrolidine-1-carboxylate;

(S)-tert-butyl 3-(2-(1-((((9H-fluoren-9-yl)methoxy)carbonyl)amino)ethyl)-5-chloro-4-oxoquinazolin-3(4H)-yl)azetidine-1-carboxylate;

(S)-tert-butyl 3-(2-((S)-1-((((9H-fluoren-9-yl)methoxy)carbonyl)amino)ethyl)-5-chloro-4-oxoquinazolin-3(4H)-yl)piperidine-1-carboxylate;

(R)-tert-butyl 3-(2-((S)-1-((((9H-fluoren-9-yl)methoxy)carbonyl)amino)ethyl)-5-chloro-4-oxoquinazolin-3(4H)-yl)piperidine-1-carboxylate;

(S)-tert-butyl 4-(2-(1-((((9H-fluoren-9-yl)methoxy)carbonyl)amino)ethyl)-5-chloro-4-oxoquinazolin-3(4H)-yl)piperidine-1-carboxylate;

(S)-tert-butyl 4-(2-(1-((((9H-fluoren-9-yl)methoxy)carbonyl)amino)propyl)-5-chloro-4-oxoquinazolin-3(4H)-yl)piperidine-1-carboxylate;

(1R,5S)-tert-butyl 6-(2-((S)-1-((((9H-fluoren-9-yl)methoxy)carbonyl)amino)ethyl)-5-chloro-4-oxoquinazolin-3(4H)-yl)-3-azabicyclo[3.1.0]hexane-3-carboxylate;

(1R,5S)-tert-butyl 6-(2-((S)-1-((((9H-fluoren-9-yl)methoxy)carbonyl)amino)ethyl)-5-chloro-8-fluoro-4-oxoquinazolin-3(4H)-yl)-3-azabicyclo[3.1.0]hexane-3-carboxylate;

(1R,5S)-tert-butyl 6-(2-((S)-((((9H-fluoren-9-yl)methoxy)carbonyl)amino)(cyclopropyl)methyl)-5-chloro-4-oxoquinazolin-3 (4H)-yl)-3-azabicyclo[3.01]hexane-3-carboxylate;

(S)-tert-butyl 4-(2-(1-(((9H-fluoren-9-yl)methoxy)carbonyl)pyrrolidin-2-yl)-5-chloro-4-oxoquinazolin-3(4H)-yl)piperazine-1-carboxylate;

(S)-tert-butyl 4-(2-(((((9H-fluoren-9-yl)methoxy)carbonyl)amino)(cyclopropyl)methyl)-5,8-difluoro-4-oxoquinazolin-3(4H)-yl)piperazine-1-carboxylate;

(S)-tert-butyl 4-(2-(1-((((9H-fluoren-9-yl)methoxy)carbonyl)amino)ethyl)-8-chloro-6-fluoro-4-oxoquinazolin-3(4H)-yl)piperazine-1-carboxylate;

(S)-tert-butyl ((5-chloro-3-morpholino-4-oxo-3,4-dihydroquinazolin-2-yl)(cyclopropyl)methyl)carbamate;

(R)-tert-butyl 2-(3-(4-benzylpiperazin-1-yl)-5-fluoro-4-oxo-3,4-dihydroquinazolin-2-yl)pyrrolidine-1-carboxylate;

(S)-tert-butyl ((5-chloro-3-(4-methylpiperazin-1-yl)-4-oxo-3,4-dihydroquinazolin-2-yl)(cyclopropyl)methyl)carbamate;

(S)-tert-butyl (1-(5-chloro-3-(4-methylpiperazin-1-yl)-4-oxo-3,4-dihydroquinazolin-2-yl)ethyl)carbamate;

(S)-tert-butyl (1-(2-(1-((((9H-fluoren-9-yl)methoxy)carbonyl)amino)ethyl)-5-chloro-4-oxoquinazolin-3(4H)-yl)piperidin-4-yl)carbamate; and (S)-tert-butyl (1-(2-(1-((((9H-fluoren-9-yl)methoxy)carbonyl)amino)ethyl)-5-chloro-4-oxoquinazolin-3(4H)-yl)pyrrolidin-3-yl)carbamate.

Example 2. Preparation of a Compound of Formula (2)

A. Preparation of a Compound of Formula (2) wherein n is 1, $R^1$ is chloro, m is 0, B is 4,7-diazaspiro[2.5]octanyl, Z is Boc, $R^5$ is H, and $R^3$ is methyl and PG is Fmoc in Formula (1)

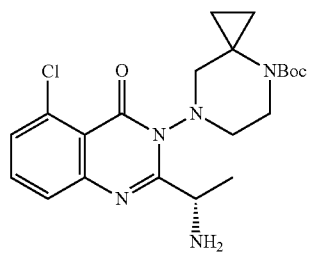 [SMILES: C[C@H](N)c1nc2cccc(Cl)c2c(=O)n1N1CCN(C(=O)OC(C)(C)C)C2(CC2)C1]

Piperidine (1.6 mL, 16 mmol) was added to a solution of (S)-tert-butyl 7-(2-(1-(((9H-fluoren-9-yl) methoxy)carbonylamino)ethyl)-5-chloro-4-oxoquinazolin-3(4H)-yl)-4,7-diazaspiro[2.5]octane-4-carboxylate (2.16 g, 3.3 mmol) in N,N-dimethylformamide (10 mL). The reaction mixture was stirred at 25° C. for 1 hour. EtOAc was added and the organic layer was washed with saturated sodium bicarbonate solution and brine. The organic layer was dried over sodium sulfate, filtered and concentrated. The resulting residue was loaded onto an EtOAc primed $SiO_2$ column. The title compound was then purified by eluting with MeOH in EtOAc (0-20%) to afford (S)-tert-butyl 7-(2-(1-aminoethyl)-5-chloro-4-oxoquinazolin-3(4H)-yl)-4,7-diazaspiro[2.5]octane-4-carboxylate. ES/MS m/z=434.2 ($M+H^+$).

B. Preparation of the below compounds of Formula (2), using the methods described in Example 2A and Reaction Scheme I:

tert-butyl 4-(2-((S)-1-aminoethyl)-5-chloro-4-oxoquinazolin-3(4H)-yl)-2-(trifluoromethyl)piperazine-1-carboxylate;

(S)-tert-butyl 4-(2-(1-((((9H-fluoren-9-yl)methoxy)carbonyl)amino)ethyl)-5-chloro-4-oxoquinazolin-3(4H)-yl)-1,4-diazepane-1-carboxylate;

(S)-tert-butyl 4-(2-(1-aminoethyl)-5-chloro-4-oxoquinazolin-3(4H)-yl)-1,4-diazepane-1-carboxylate;

(S)-tert-butyl 4-(2-(1-aminoethyl)-5-chloro-4-oxoquinazolin-3(4H)-yl)piperazine-1-carboxylate;

(S)-tert-butyl 4-(2-(1-aminopropyl)-5-chloro-4-oxoquinazolin-3(4H)-yl)piperazine-1-carboxylate;

(S)-tert-butyl 4-(2-(1-amino-3-methylbutyl)-5-chloro-4-oxoquinazolin-3(4H)-yl)piperazine-1-carboxylate;

(S)-tert-butyl 4-(2-(1-aminoethyl)-5,8-dichloro-4-oxoquinazolin-3(4H)-yl)piperazine-1-carboxylate;

(S)-tert-butyl 4-(2-(amino(cyclopropyl)methyl)-5-chloro-4-oxoquinazolin-3(4H)-yl)piperazine-1-carboxylate;

tert-butyl 4-(2-((S)-1-aminoethyl)-5-chloro-4-oxoquinazolin-3(4H)-yl)azepane-1-carboxylate;

tert-butyl 3-(2-((S)-1-aminoethyl)-5-chloro-4-oxoquinazolin-3(4H)-yl)piperidine-1-carboxylate;

tert-butyl 3-(2-((S)-1-aminoethyl)-5-chloro-4-oxoquinazolin-3(4H)-yl)pyrrolidine-1-carboxylate;

tert-butyl 4-(2-((S)-1-aminoethyl)-5-chloro-4-oxoquinazolin-3(4H)-yl)piperidine-1-carboxylate;

(S)-tert-butyl 4-(2-(1-aminoethyl)-5-methyl-4-oxoquinazolin-3(4H)-yl)piperidine-1-carboxylate;

(S)-tert-butyl 4-(2-(1-aminoethyl)-5-chloro-8-fluoro-4-oxoquinazolin-3(4H)-yl)piperazine-1-carboxylate;

(S)-tert-butyl 4-(2-(amino(cyclopropyl)methyl)-5-chloro-8-fluoro-4-oxoquinazolin-3(4H)-yl)piperazine-1-carboxylate;

(S)-tert-butyl 4-(2-(amino(cyclopropyl)methyl)-5,8-difluoro-4-oxoquinazolin-3(4H)-yl)piperazine-1-carboxylate;

(S)-tert-butyl 4-(2-(1-aminoethyl)-5,8-difluoro-4-oxoquinazolin-3(4H)-yl)piperazine-1-carboxylate;

tert-butyl 4-(2-((S)-1-aminoethyl)-5-chloro-4-oxoquinazo-lin-3(4H)-yl)-3,3-difluoropiperidine-1-carboxylate;
(R)-tert-butyl 3-(2-((S)-1-aminoethyl)-5-chloro-4-oxoqui-nazolin-3(4H)-yl)pyrrolidine-1-carboxylate;
(S)-tert-butyl 3-(2-((S)-1-aminoethyl)-5-chloro-4-oxoqui-nazolin-3(4H)-yl)pyrrolidine-1-carboxylate;
(S)-tert-butyl 3-(2-(1-aminoethyl)-5-chloro-4-oxoquinazo-lin-3(4H)-yl)azetidine-1-carboxylate;
(S)-tert-butyl 3-(2-((S)-1-aminoethyl)-5-chloro-4-oxoqui-nazolin-3(4H)-yl)piperidine-1-carboxylate;
(R)-tert-butyl 3-(2-((S)-1-aminoethyl)-5-chloro-4-oxoqui-nazolin-3(4H)-yl)piperidine-1-carboxylate;
(S)-tert-butyl 4-(2-(1-aminoethyl)-5-chloro-4-oxoquinazo-lin-3(4H)-yl)piperidine-1-carboxylate;
(S)-tert-butyl 4-(2-(1-aminopropyl)-5-chloro-4-oxoquinazo-lin-3(4H)-yl)piperidine-1-carboxylate;
(1R,5S)-tert-butyl 6-(2-((S)-1-aminoethyl)-5-chloro-4-oxo-quinazolin-3(4H)-yl)-3-azabicyclo[3.1.0]hexane-3-car-boxylate;
(1R,5S)-tert-butyl 6-(2-((S)-1-aminoethyl)-5-chloro-8-fluoro-4-oxoquinazolin-3(4H)-yl)-3-azabicyclo[3.1.0]hexane-3-carboxylate;
(1R,5S)-tert-butyl 6-(2-((S)-amino(cyclopropyl)methyl)-5-chloro-4-oxoquinazolin-3(4H)-yl)-3-azabicyclo[3.1.0]hexane-3-carboxylate
(S)-tert-butyl 4-(5-chloro-4-oxo-2-(pyrrolidin-2-yl)quinazo-lin-3(4H)-yl)piperazine-1-carboxylate;
(S)-tert-butyl 4-(2-(1-aminoethyl)-8-chloro-6-fluoro-4-oxo-quinazolin-3(4H)-yl)piperazine-1-carboxylate;
(S)-tert-butyl 4-(2-(amino(cyclopropyl)methyl)-5,8-dif-luoro-4-oxoquinazolin-3(4H)-yl)piperazine-1-carboxy-late; and
(S)-tert-butyl (1-(2-(1-aminoethyl)-5-chloro-4-oxoquinazo-lin-3 (4H)-yl)piperidin-4-yl)carbamate; and tert-butyl (1-(2-((S)-1-aminoethyl)-5-chloro-4-oxoquinazolin-3 (4H)-yl)pyrrolidin-3-yl)carbamate.

C. Preparation of a Compound of Formula (2) wherein n is 1, R¹ is chloro, B is -4-methylpiperazinyl, R⁵ is H, m is 0, and R³ is cyclopropyl and PG is Boc in formula (1)

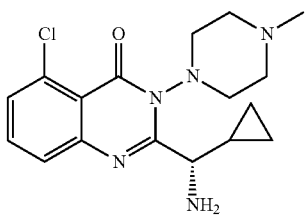 [SMILES: CN1CCN(n2c([C@@H](N)C3CC3)nc3cccc(Cl)c3c2=O)CC1]

To a solution of (S)-tert-butyl ((5-chloro-3-(4-methylpip-erazin-1-yl)-4-oxo-3,4-dihydroquinazolin-2-yl)(cyclopro-pyl)methyl)carbamate (3.0 g, 6.7 mmol) in dichloromethane (20 mL) was added trifluoroacetic acid (5.2 mL). The reaction stirred for 1 hr at 25° C. and was concentrated to give (S)-2-(amino(cyclopropyl)methyl)-5-chloro-3-(4-methylpiperazin-1-yl)quinazolin-4(3H)-one. The title compound was carried to the next reaction without further purification. ES/MS 348.2 (M+H⁺).

D. Preparation of the below compounds of Formula (2), using the methods described in Example 2C and Reaction Scheme I:
(S)-2-(1-aminoethyl)-5-chloro-3-(4-methylpiperazin-1-yl)quinazolin-4(3H)-one;
(S)-2-(1-aminoethyl)-5-chloro-3-(1-methylpiperidin-4-yl)quinazolin-4(3H)-one;
2-((S)-1-aminoethyl)-5-chloro-3-((1R,5S)-8-methyl-8-azabicyclo[3.2.1]octan-3-yl)quinazolin-4(3H)-one; (S)-2-(1-aminoethyl)-3-(4-benzylpiperazin-1-yl)-5-chloroqui-nazolin-4(3H)-one;
(S)-2-(amino(cyclopropyl)methyl)-5-chloro-3-morpholino-quinazolin-4(3H)-one;
(R)-3-(4-benzylpiperazin-1-yl)-5-fluoro-2-(pyrrolidin-2-yl)quinazolin-4(3H)-one;
(S)-2-(1-aminoethyl)-5-chloro-3-(4-methylpiperazin-1-yl)quinazolin-4(3H)-one; and
(S)-2-(amino(cyclopropyl)methyl)-5-chloro-3-(4-methyl-piperazin-1-yl)quinazolin-4(3H)-one.

Example 3. Preparation of a Compound of Formula (3)

A. Preparation of a compound of formula (3) wherein n is 1, R¹ is chloro, m is 0, B is 4,7-diazaspiro[2,5]octanyl, Z is Boc, R⁵ is H, A is a single bond, R³ is methyl, and R⁴ is 2,6-diamino-5-cyanopyrimidin-4-yl

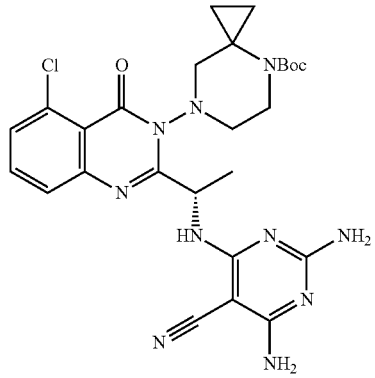 [SMILES: C[C@H](Nc1nc(N)nc(N)c1C#N)c1nc2cccc(Cl)c2c(=O)n1N1CCN(C(=O)OC(C)(C)C)C2(CC2)C1]

A mixture of (S)-tert-butyl 7-(2-(1-aminoethyl)-5-chloro-4-oxoquinazolin-3(4H)-yl)-4,7-diazaspiro[2.5]octane-4-car-boxylate (99 mg, 0.23 mmol), N,N-diisopropylethylamine (119 µL, 0.68 mmol), and 2,4-diamino-6-chloropyrimidine-5-carbonitrile (39 mg, 0.23 mmol) in isopropyl alcohol (1 mL) was stirred in a microwave at 130° C. for 14 hr. The mixture was concentrated to give (S)-tert-butyl 7-(5-chloro-2-(1-((2,6-diamino-5-cyanopyrimidin-4-yl)amino)ethyl)-4-oxoquinazolin-3(4H)-yl)-4,7-diazaspiro[2.5]octane-4-car-boxylate as a solid and was carried onto the next reaction without purification. ES/MS 567.3 (M+H⁺).

B. Preparation of the below compounds of formula (3) or (I), using the methods described in Example 3A and Reaction Scheme I:
tert-butyl 4-(5-chloro-2-((S)-1-((2,6-diamino-5-cyanopy-rimidin-4-yl)amino)ethyl)-4-oxoquinazolin-3(4H)-yl)-2-(trifluoromethyl)piperazine-1-carboxylate;
tert-butyl 4-(2-((S)-1-((6-amino-5-cyanopyrimidin-4-yl)amino)ethyl)-5-chloro-4-oxoquinazolin-3(4H)-yl)-2-(trif-luoromethyl)piperazine-1-carboxylate;
(S)-tert-butyl 4-(5-chloro-2-(1-(imidazo[2,1-f][1,2,4]tri-azin-4-ylamino)ethyl)-4-oxoquinazolin-3(4H)-yl)-1,4-di-azepane-1-carboxylate;
(S)-tert-butyl 4-(5-chloro-2-(1-((2,6-diamino-5-chloropy-rimidin-4-yl)amino)ethyl)-4-oxoquinazolin-3(4H)-yl)piperazine-1-carboxylate;
(S)-tert-butyl 4-(5-chloro-2-(1-((2,6-diamino-5-cyanopy-rimidin-4-yl)amino)propyl)-4-oxoquinazolin-3(4H)-yl)piperazine-1-carboxylate;

(S)-tert-butyl 4-(2-(1-((5-bromo-7H-pyrrolo[2,3-d]pyrimidin-4-yl)amino)ethyl)-5-chloro-4-oxoquinazolin-3(4H)-yl)piperazine-1-carboxylate;
(S)-tert-butyl 4-(5-chloro-4-oxo-2-(1-(thiazolo[5,4-d]pyrimidin-7-ylamino)ethyl)quinazolin-3(4H)-yl)piperazine-1-carboxylate;
(S)-tert-butyl 4-(5-chloro-2-(1-((6-chloropyrido[3,2-d]pyrimidin-4-yl)amino)ethyl)-4-oxoquinazolin-3(4H)-yl)piperazine-1-carboxylate;
(S)-tert-butyl 4-(5-chloro-4-oxo-2-(1-(pyrido[3,2-d]pyrimidin-4-ylamino)ethyl)quinazolin-3(4H)-yl)piperazine-1-carboxylate;
(S)-tert-butyl 4-(2-(1-((6-amino-5-cyanopyrimidin-4-yl)amino)-3-methylbutyl)-5-chloro-4-oxoquinazolin-3(4H)-yl)piperazine-1-carboxylate;
(S)-tert-butyl 4-(5-chloro-2-(1-((2,6-diamino-5-cyanopyrimidin-4-yl)amino)-3-methylbutyl)-4-oxoquinazolin-3(4H)-yl)piperazine-1-carboxylate;
(S)-tert-butyl 4-(2-(1-((6-amino-5-cyanopyrimidin-4-yl)amino)ethyl)-5,8-dichloro-4-oxoquinazolin-3(4H)-yl)piperazine-1-carboxylate;
(S)-tert-butyl 4-(2-(((6-amino-5-cyanopyrimidin-4-yl)amino)(cyclopropyl)methyl)-5-chloro-4-oxoquinazolin-3(4H)-yl)piperazine-1-carboxylate;
(S)-tert-butyl 4-(5-chloro-2-(cyclopropyl((2,6-diamino-5-cyanopyrimidin-4-yl)amino)methyl)-4-oxoquinazolin-3(4H)-yl)piperazine-1-carboxylate;
(S)-tert-butyl 4-(5-chloro-2-(cyclopropyl(thiazolo[5,4-d]pyrimidin-7-ylamino)methyl)-4-oxoquinazolin-3(4H)-yl)piperazine-1-carboxylate;
(S)-tert-butyl 4-(2-(1-((6-amino-5-cyanopyrimidin-4-yl)amino)propyl)-5-chloro-4-oxoquinazolin-3(4H)-yl)piperazine-1-carboxylate;
(S)-tert-butyl 4-(5-chloro-4-oxo-2-(1-(thiazolo[5,4-d]pyrimidin-7-ylamino)propyl)quinazolin-3(4H)-yl)piperazine-1-carboxylate;
tert-butyl 4-(5-chloro-4-oxo-2-((S)-1-(pyrido[3,2-d]pyrimidin-4-ylamino)ethyl)quinazolin-3(4H)-yl)azepane-1-carboxylate;
tert-butyl 4-(5-chloro-2-((S)-1-(imidazo[2,1-f][1,2,4]triazin-4-ylamino)ethyl)-4-oxoquinazolin-3(4H)-yl)azepane-1-carboxylate;
tert-butyl 3-(2-((S)-1-((6-amino-5-cyanopyrimidin-4-yl)amino)ethyl)-5-chloro-4-oxoquinazolin-3(4H)-yl)piperidine-1-carboxylate;
tert-butyl 4-(2-((S)-1-((6-amino-5-cyanopyrimidin-4-yl)amino)ethyl)-5-chloro-4-oxoquinazolin-3(4H)-yl)azepane-1-carboxylate;
tert-butyl 3-(2-((S)-1-((6-amino-5-cyanopyrimidin-4-yl)amino)ethyl)-5-chloro-4-oxoquinazolin-3(4H)-yl)pyrrolidine-1-carboxylate;
tert-butyl 4-(2-((S)-1-((6-amino-5-cyanopyrimidin-4-yl)amino)ethyl)-5-chloro-4-oxoquinazolin-3(4H)-yl)piperidine-1-carboxylate;
(S)-tert-butyl 4-(2-(1-((6-amino-5-cyanopyrimidin-4-yl)amino)ethyl)-5-methyl-4-oxoquinazolin-3(4H)-yl)piperidine-1-carboxylate;
(S)-tert-butyl 4-(2-(1-((6-amino-5-((5-fluoropyridin-2-yl)ethynyl)pyrimidin-4-yl)amino)ethyl)-5-chloro-4-oxoquinazolin-3(4H)-yl)piperazine-1-carboxylate;
(S)-tert-butyl 4-(5-chloro-2-(1-((2,6-diamino-5-cyanopyrimidin-4-yl)amino)ethyl)-4-oxoquinazolin-3(4H)-yl)piperazine-1-carboxylate;
(S)-tert-butyl 4-(2-(1-((6-amino-5-cyanopyrimidin-4-yl)amino)ethyl)-5-chloro-4-oxoquinazolin-3(4H)-yl)piperazine-1-carboxylate;
(S)-tert-butyl 4-(5-chloro-2-(1-((2,6-diamino-5-cyanopyrimidin-4-yl)amino)ethyl)-8-fluoro-4-oxoquinazolin-3(4H)-yl)piperazine-1-carboxylate;
(S)-tert-butyl 4-(5,8-dichloro-2-(1-((2,6-diamino-5-cyanopyrimidin-4-yl)amino)ethyl)-4-oxoquinazolin-3(4H)-yl)piperazine-1-carboxylate;
(S)-tert-butyl 4-(5,8-dichloro-2-(1-((6-chloropyrido[3,2-d]pyrimidin-4-yl)amino)ethyl)-4-oxoquinazolin-3(4H)-yl)piperazine-1-carboxylate;
(S)-tert-butyl 4-(5-chloro-2-(1-((6-chloropyrido[3,2-d]pyrimidin-4-yl)amino)ethyl)-8-fluoro-4-oxoquinazolin-3(4H)-yl)piperazine-1-carboxylate;
(S)-tert-butyl 4-(5-chloro-8-fluoro-4-oxo-2-(1-(thiazolo[5,4-d]pyrimidin-7-ylamino)ethyl)quinazolin-3(4H)-yl)piperazine-1-carboxylate;
(S)-tert-butyl 4-(5,8-dichloro-4-oxo-2-(1-(thiazolo[5,4-d]pyrimidin-7-ylamino)ethyl)quinazolin-3(4H)-yl)piperazine-1-carboxylate;
(S)-tert-butyl 4-(5-chloro-2-(cyclopropyl((2,6-diamino-5-cyanopyrimidin-4-yl)amino)methyl)-8-fluoro-4-oxoquinazolin-3(4H)-yl)piperazine-1-carboxylate;
(S)-tert-butyl 4-(5-chloro-2-(cyclopropyl(imidazo[2,1-f][1,2,4]triazin-4-ylamino)methyl)-8-fluoro-4-oxoquinazolin-3(4H)-yl)piperazine-1-carboxylate;
(S)-tert-butyl 4-(2-(((2-amino-5-cyano-6-methylpyrimidin-4-yl)amino)(cyclopropyl)methyl)-5-chloro-4-oxoquinazolin-3 (4H)-yl)piperazine-1-carboxylate;
(S)-tert-butyl 4-(2-(1-((2-amino-5-cyano-6-methylpyrimidin-4-yl)amino)propyl)-5-chloro-4-oxoquinazolin-3(4H)-yl)piperazine-1-carboxylate;
(S)-tert-butyl 4-(5-chloro-2-(cyclopropyl(imidazo[2,1-f][1,2,4]triazin-4-ylamino)methyl)-4-oxoquinazolin-3(4H)-yl)piperazine-1-carboxylate;
(S)-tert-butyl 4-(5-chloro-2-(1-(imidazo[2,1-f][1,2,4]triazin-4-ylamino)propyl)-4-oxoquinazolin-3(4H)-yl)piperazine-1-carboxylate;
(S)-tert-butyl 4-(2-(cyclopropyl(imidazo[2,1-f][1,2,4]triazin-4-ylamino)methyl)-5,8-difluoro-4-oxoquinazolin-3 (4H)-yl)piperazine-1-carboxylate;
(S)-tert-butyl 4-(5,8-difluoro-2-(1-(imidazo[2,1-f][1,2,4]triazin-4-ylamino)ethyl)-4-oxoquinazolin-3(4H)-yl)piperazine-1-carboxylate;
(S)-tert-butyl 4-(2-(1-((2,6-diamino-5-cyanopyrimidin-4-yl)amino)ethyl)-5,8-difluoro-4-oxoquinazolin-3(4H)-yl)piperazine-1-carboxylate;
tert-butyl 4-(5-chloro-2-((S)-1-((2,6-diamino-5-cyanopyrimidin-4-yl)amino)ethyl)-4-oxoquinazolin-3(4H)-yl)-3,3-difluoropiperidine-1-carboxylate;
(S)-tert-butyl 4-(2-(1((6-amino-5-chloropyrimidin-4-yl)amino)ethyl)-5-chloro-4-oxoquinazolin-3(4H)-yl)piperazine-1-carboxylate;
(S)-tert-butyl 4-(5-chloro-2-(1-((5-chlorothieno[2,3-d]pyrimidin-4-yl)amino)ethyl)-4-oxoquinazolin-3(4H)-yl)piperazine-1-carboxylate;
(S)-tert-butyl 4-(5-chloro-2-(1-(furo[3,2-d]pyrimidin-4-ylamino)ethyl)-4-oxoquinazolin-3(4H)-yl)piperazine-1-carboxylate;
(R)-tert-butyl 3-(5-chloro-2-((S)-1-((2,6-diamino-5-cyanopyrimidin-4-yl)amino)ethyl)-4-oxoquinazolin-3(4H)-yl)pyrrolidine-1-carboxylate;
(S)-tert-butyl 3-(5-chloro-2-((S)-1-((2,6-diamino-5-cyanopyrimidin-4-yl)amino)ethyl)-4-oxoquinazolin-3(4H)-yl)pyrrolidine-1-carboxylate;
(S)-tert-butyl 3-(5-chloro-2-(1-((2,6-diamino-5-cyanopyrimidin-4-yl)amino)ethyl)-4-oxoquinazolin-3(4H)-yl)azetidine-1-carboxylate;

(S)-tert-butyl 3-(5-chloro-2-((S)-1-((2,6-diamino-5-cyano-pyrimidin-4-yl)amino)ethyl)-4-oxoquinazolin-3(4H)-yl)piperidine-1-carboxylate;
(R)-tert-butyl 3-(5-chloro-2-((S)-1-((2,6-diamino-5-cyano-pyrimidin-4-yl)amino)ethyl)-4-oxoquinazolin-3(4H)-yl)piperidine-1-carboxylate;
(S)-tert-butyl 4-(5-chloro-2-(1-((2,6-diamino-5-cyanopyrimidin-4-yl)amino)ethyl)-4-oxoquinazolin-3(4H)-yl)piperidine-1-carboxylate;
(S)-tert-butyl 4-(5-chloro-2-(1-((2,6-diamino-5-chloropyrimidin-4-yl)amino)ethyl)-4-oxoquinazolin-3(4H)-yl)piperidine-1-carboxylate;
(S)-tert-butyl 4-(2-(1-((2-amino-5-cyano-6-methylpyrimidin-4-yl)amino)ethyl)-5-chloro-4-oxoquinazolin-3(4H)-yl)piperidine-1-carboxylate;
(S)-tert-butyl 4-(5-chloro-2-(1-((2,6-diamino-5-cyanopyrimidin-4-yl)amino)propyl)-4-oxoquinazolin-3(4H)-yl)piperidine-1-carboxylate;
(S)-tert-butyl 4-(2-(1-((2-amino-5-cyano-6-methylpyrimidin-4-yl)amino)propyl)-5-chloro-4-oxoquinazolin-3(4H)-yl)piperidine-1-carboxylate;
(S)-tert-butyl 4-(2-(1-((2-amino-5-cyano-6-methylpyrimidin-4-yl)amino)ethyl)-5-chloro-8-fluoro-4-oxoquinazolin-3(4H)-yl)piperazine-1-carboxylate;
(S)-tert-butyl 4-(5-chloro-2-(1-((2,6-diamino-5-chloropyrimidin-4-yl)amino)ethyl)-8-fluoro-4-oxoquinazolin-3(4H)-yl)piperazine-1-carboxylate;
(1R,5S)-tert-butyl 6-(5-chloro-2-((S)-1-((2,6-diamino-5-cyanopyrimidin-4-yl)amino)ethyl)-4-oxoquinazolin-3(4H)-yl)-3-azabicyclo[3.1.0]hexane-3-carboxylate;
(S)-tert-butyl 4-(5-chloro-4-oxo-2-(1-(thiazolo[5,4-d]pyrimidin-7-ylamino)ethyl)quinazolin-3 (4H)-yl)piperidine-1-carboxylate;
(1R,5S)-tert-butyl 6-(5-chloro-2-((S)-1-((2,6-diamino-5-cyanopyrimidin-4-yl)amino)ethyl)-8-fluoro-4-oxoquinazolin-3 (4H)-yl)-3-azabicyclo[3.1.0]hexane-3-carboxylate;
(1R,5S)-tert-butyl 6-(2-((S)-1-((2-amino-5-cyano-6-methylpyrimidin-4-yl)amino)ethyl)-5-chloro-8-fluoro-4-oxoquinazolin-3(4H)-yl)-3-azabicyclo[3.1.0]hexane-3-carboxylate;
(1R,5S)-tert-butyl 6-(5-chloro-2-((S)-cyclopropyl((2,6-diamino-5-cyanopyrimidin-4-yl)amino)methyl)-4-oxoquinazolin-3(4H)-yl)-3-azabicyclo[3.1.0]hexane-3-carboxylate;
(1R,5S)-tert-butyl 6-(2-((S)-((2-amino-5-cyano-6-methylpyrimidin-4-yl)amino)(cyclopropyl)methyl)-5-chloro-4-oxoquinazolin-3(4H)-yl)-3-azabicyclo[3.1.0]hexane-3-carboxylate;
tert-butyl 4-(5-chloro-2-((S)-1-((2,6-diamino-5-chloropyrimidin-4-yl)amino)ethyl)-4-oxoquinazolin-3(4H)-yl)azepane-1-carboxylate;
tert-butyl 4-(2-((S)-1-((2-amino-5-cyano-6-methylpyrimidin-4-yl)amino)ethyl)-5-chloro-4-oxoquinazolin-3(4H)-yl)azepane-1-carboxylate;
tert-butyl 4-(5-chloro-2-((S)-1-((2,6-diamino-5-cyanopyrimidin-4-yl)amino)ethyl)-4-oxoquinazolin-3(4H)-yl)azepane-1-carboxylate;
(S)-tert-butyl 4-(2-(1-((2-amino-6-chloro-5-cyanopyrimidin-4-yl)amino)ethyl)-5-chloro-4-oxoquinazolin-3(4H)-yl)piperidine-1-carboxylate;
(S)-tert-butyl 4-(5-chloro-2-(1-(imidazo[2,1-f][1,2,4]triazin-4-yl)pyrrolidin-2-yl)-4-oxoquinazolin-3(4H)-yl)piperazine-1-carboxylate;
(S)-2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile (Compound 1). 1H NMR (400 MHz, DMSO-d$_6$) δ 7.84-7.71 (m, 1H), 7.68-7.53 (m, 4H), 7.46 (s, 2H), 7.24-7.02 (m, 2H), 5.40 (d, J=8.6 Hz, 1H), 4.66-4.56 (m, 1H), 4.51 (d, J=13.1 Hz, 1H), 4.00-3.83 (m, 2H), 3.29 (t, J=12.6 Hz, 1H), 3.16 (d, J=10.7 Hz, 1H), 3.02 (d, J=10.4 Hz, 1H), 2.86 (s, 1H), 1.56 (ddt, J=13.2, 8.3, 4.2 Hz, 3H), 0.60 (dddd, J=30.3, 16.6, 8.8, 3.9 Hz, 3H), 0.39 (dq, J=8.5, 4.4 Hz, 1H). ES/MS 481.2 (M+H$^+$).

(S)-5-chloro-2-(cyclopropyl((2,6-diamino-5-chloropyrimidin-4-yl)amino)methyl)-3-(4-methylpiperazin-1-yl)quinazolin-4(3H)-one (Compound 2). 1H NMR (400 MHz, DMSO-d$_6$) δ 9.93 (s, 1H), 7.78 (t, J=8.0 Hz, 1H), 7.62 (ddd, J=18.0, 8.0, 1.2 Hz, 2H), 7.56-7.06 (m, 4H), 5.38-5.21 (m, 1H), 4.33-4.03 (m, 2H), 3.61 (d, J=11.8 Hz, 1H), 3.52 (d, J=11.8 Hz, 1H), 3.29 (t, J=14.5 Hz, 2H), 3.12 (d, J=12.1 Hz, 1H), 2.81 (s, 4H), 1.55 (dtd, J=13.3, 8.1, 5.0 Hz, 1H), 0.57 (pd, J=8.8, 4.7 Hz, 3H), 0.41 (dq, J=7.8, 4.3, 3.7 Hz, 1H). ES/MS 490.2 (M+H$^+$).

(S)-2,4-diamino-6-((1-(3-(4-benzylpiperazin-1-yl)-5-chloro-4-oxo-3,4-dihydroquinazolin-2-yl)ethyl)amino)pyrimidine-5-carbonitrile (Compound 3). 1H NMR (400 MHz, DMSO-d$_6$) δ 7.70 (td, J=8.0, 1.0 Hz, 1H), 7.55-7.47 (m, 2H), 7.39-7.21 (m, 5H), 6.68-6.57 (m, 3H), 6.27 (s, 3H), 5.49 (td, J=8.4, 4.1 Hz, 1H), 4.11-3.98 (m, 1H), 3.87 (t, J=10.3 Hz, 1H), 3.56 (d, J=13.1 Hz, 1H), 3.48 (d, J=13.1 Hz, 1H), 3.14 (d, J=10.3 Hz, 1H), 2.92 (d, J=10.2 Hz, 1H), 2.83 (t, J=12.9 Hz, 2H), 2.28 (t, J=10.9 Hz, 1H), 2.20-2.09 (m, 1H), 1.95-1.75 (m, 2H), 1.44 (d, J=6.6 Hz, 3H). ES/MS 531.2 (M+H$^+$).

2,4-diamino-6-(((1S)-1-(5-chloro-3-((1R,5S)-8-methyl-8-azabicyclo[3.2.1]octan-3-yl)-4-oxo-3,4-dihydroquinazolin-2-yl)ethyl)amino)pyrimidine-5-carbonitrile (Compound 4). $^1$H NMR (400 MHz, DMSO-d$_6$)) δ 9.60 (s, 1H), 9.08 (d, J=11.5 Hz, 1H), 8.39 (d, J=38.4 Hz, 4H), 7.74 (dd, J=8.4, 7.6 Hz, 1H), 7.66-7.44 (m, 2H), 5.34 (p, J=6.4 Hz, 1H), 4.78 (p, J=9.7 Hz, 1H), 4.03-3.83 (m, 2H), 2.71 (d, J=4.8 Hz, 3H), 2.67-2.52 (m, 2H), 2.34 (dq, J=17.2, 10.6, 9.5 Hz, 2H), 2.22 (q, J=8.8, 7.1 Hz, 1H), 2.13 (dd, J=14.1, 8.2 Hz, 1H), 1.52 (d, J=6.4 Hz, 3H). ES/MS 480.2 (M+H$^+$).

(S)-4-amino-6-((1-(5-chloro-3-(4-methylpiperazin-1-yl)-4-oxo-3,4-dihydroquinazolin-2-yl)ethyl)amino)pyrimidine-5-carbonitrile (Compound 5). 1H NMR (400 MHz, DMSO-d6) δ 7.99 (s, 1H), 7.74-7.67 (m, 2H), 7.52 (d, J=8.0 Hz, 2H), 7.42-7.28 (m, 2H), 5.72 (p, J=6.7 Hz, 1H), 4.16 (t, J=12.8 Hz, 1H), 4.08 (t, J=11.6 Hz, 1H), 3.52 (t, J=11.6 Hz, 2H), 3.42 (d, J=11.8 Hz, 2H), 3.33 (d, J=12.5 Hz, 1H), 3.23 (q, J=11.4 Hz, 1H), 3.07 (q, J=11.4 Hz, 1H), 2.80 (d, J=4.1 Hz, 3H), 1.47 (d, J=6.8 Hz, 3H). ES/MS 440.1 (M+H$^+$).

(S)-4-amino-6-((1-(5-chloro-3-(1-methylpiperidin-4-yl)-4-oxo-3,4-dihydroquinazolin-2-yl)ethyl)amino)pyrimidine-5-carbonitrile (Compound 6). 1H NMR (400 MHz, DMSO-d6) δ 8.08 (s, 1H), 7.85 (d, J=6.9 Hz, 1H), 7.73-7.66 (m, 1H), 7.52 (d, J=8.1 Hz, 2H), 7.40 (s, 2H), 5.60 (m, 1H), 4.35 (m, 1H), 3.50 (m, 2H), 3.05 (m, 4H), 2.72 (d, J=4.5 Hz, 3H), 1.94 (m, 2H), 1.50 (d, J=6.5 Hz, 3H). ES/MS 439.0 (M+H+).

(S)-tert-butyl 4-(2-(cyclopropyl((2,6-diamino-5-cyanopyrimidin-4-yl)amino)methyl)-5,8-difluoro-4-oxoquinazolin-3(4H)-yl)piperazine-1-carboxylate;
(S)-tert-butyl 4-(8-chloro-2-(1-((2,6-diamino-5-cyanopyrimidin-4-yl)amino)ethyl)-6-fluoro-4-oxoquinazolin-3(4H)-yl)piperazine-1-carboxylate;
(S)-2,4-diamino-6-(((5-chloro-3-morpholino-4-oxo-3,4-dihydroquinazolin-2-yl)(cyclopropyl)methyl)amino)pyrimidine-5-carbonitrile (Compound 121). $^1$H NMR (400

MHz, DMSO-$d_6$) δ 7.77 (dd, J=7.8 Hz, 1H), 7.66-7.52 (m, 2H), 5.38 (t, J=8.1 Hz, 1H), 4.06-3.90 (m, 2H), 3.84 (d, J=10.8 Hz, 1H), 3.75 (d, J=10.4 Hz, 1H), 3.67-3.55 (m, 1H), 3.22 (t, J=11.4 Hz, 1H), 2.93 (d, J=10.6 Hz, 1H), 2.84 (d, J=10.6 Hz, 1H), 1.61-1.46 (m, 1H), 0.69-0.59 (m, 1H), 0.59-0.45 (m, 2H), 0.43-0.31 (m, 1H). ES/MS 468.2 (M+H$^+$).

(S)-5-chloro-2-(cyclopropyl((2,6-diamino-5-chloropyrimidin-4-yl)amino)methyl)-3-morpholinoquinazolin-4(3H)-one (Compound 122) $^1$H NMR (400 MHz, DMSO-$d_6$) δ 9.95 (s, 1H), 7.78 (t, J=8.0 Hz, 1H), 7.62 (ddd, J=18.0, 8.0, 1.2 Hz, 2H), 7.53-7.06 (m, 6H), 5.30 (d, J=9.1 Hz, 1H), 4.06-3.90 (m, 2H), 3.84 (d, J=10.8 Hz, 1H), 3.75 (d, J=10.4 Hz, 1H), 3.67-3.55 (m, 1H), 3.22 (t, J=11.4 Hz, 1H), 2.93 (d, J=10.6 Hz, 1H), 2.84 (d, J=10.6 Hz, 1H), 1.61-1.46 (m, 1H), 0.69-0.59 (m, 1H), 0.59-0.45 (m, 2H), 0.43-0.31 (m, 1H). ES/MS 468.2 (M+H$^+$).

(R)-2,4-diamino-6-(2-(3-(4-benzylpiperazin-1-yl)-5-fluoro-4-oxo-3,4-dihydroquinazolin-2-yl)pyrrolidin-1-yl)pyrimidine-5-carbonitrile (Compound 124). $^1$H NMR (400 MHz, DMSO-$d_6$) δ 7.69 (td, J=8.2, 5.5 Hz, 1H), 7.36-7.34 (m, 3H), 7.32-7.29 (m, 1H), 7.29-7.25 (m, 1H), 7.24-7.17 (m, 1H), 6.46 (s, 2H), 6.00 (s, 2H), 5.70 (s, 1H), 4.10-3.83 (m, 4H), 3.60-3.46 (m, 2H), 2.96 (dd, J=10.5, 2.3 Hz, 1H), 2.87-2.78 (m, 2H), 2.29-2.19 (m, 1H), 2.04-1.93 (m, 1H). ES/MS 541.3 (M+H$^+$).

(S)-2,4-diamino-6-((1-(5-chloro-3-(4-methylpiperazin-1-yl)-4-oxo-3,4-dihydroquinazolin-2-yl)ethyl)amino)pyrimidine-5-carbonitrile (Compound 125). $^1$H NMR (400 MHz, DMSO-$d_6$) δ 7.72 (dd, J=8.2, 7.8 Hz, 1H), 7.60-7.45 (m, 2H), 6.91 (d, J=7.5 Hz, 1H), 6.57 (s, 2H), 6.35 (s, 3H), 5.63 (dd, J=7.5, 6.6 Hz, 1H), 4.06-3.94 (m, 1H), 3.90 (s, 0H), 3.09-3.00 (m, 1H), 2.91 (d, J=10.3 Hz, 1H), 2.73 (dd, J=22.1, 10.9 Hz, 2H), 2.19 (qp, J=1.4, 0.5 Hz, 3H), 1.99 (s, 1H), 1.46 (d, J=6.7 Hz, 3H). ES/MS 545.2 (M+H$^+$).

(S)-tert-butyl (1-(2-(1-((6-amino-5-cyanopyrimidin-4-yl)amino)ethyl)-5-chloro-4-oxoquinazolin-3(4H)-yl)piperidin-4-yl)carbamate;

(S)-tert-butyl (1-(5-chloro-2-(1-((2,6-diamino-5-cyanopyrimidin-4-yl)amino)ethyl)-4-oxoquinazolin-3(4H)-yl)piperidin-4-yl)carbamate; and tert-butyl (1-(2-((S)-1-((6-amino-5-cyanopyrimidin-4-yl)amino)ethyl)-5-chloro-4-oxoquinazolin-3(4H)-yl)pyrrolidin-3-yl)carbamate.

C. Preparation of a compound of formula (3), where A is CO, $R^1$ is chloro, m is 0, B is piperazinyl, Z is Boc, $R^5$ is hydrogen, $R^3$ is methyl, and $R^4$ is 3-aminopiperazin-2-yl

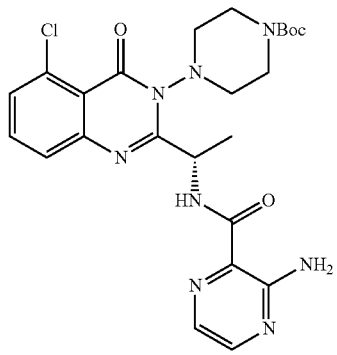 [SMILES: C[C@H](NC(=O)c1nccnc1N)c1nc2cccc(Cl)c2c(=O)n1N1CCN(C(=O)OC(C)(C)C)CC1]

To (S)-tert-butyl 4-(2-(1-aminoethyl)-5-chloro-4-oxoquinazolin-3(4H)-yl)piperazine-1-carboxylate (200 mg, 0.49 mmol), 1-[Bis(dimethylamino)methylene]-1H-1,2,3-triazolo[4,5-b]pyridinium 3-oxid hexafluorophosphate (279 mg, 0.735 mmol) and 3-amino-2-pyrazinecarboxylic acid (196 mg, 1.1 mmol) in DMF (3 mL) was added N,N-diisopropylethylamine (0.4 mL). After stirring at room temp for 1 hour, water was added and the mixture was washed with EtOAc (3×30 mL). The combined organic layers were dried over magnesium sulfate, filtered, and concentrated. The residue was purified on a reverse phase HPLC system run from 0 to 95% ACN in water (0.1% TFA) to give (S)-tert-butyl 4-(2-(1-(3-aminopyrazine-2-carboxamido)ethyl)-5-chloro-4-oxoquinazolin-3(4H)-yl)piperazine-1-carboxylate. ES/MS m/z=529.2 (M+H)$^+$ D. Preparation of the below compounds of Formula (3), using the procedures described in Example 3C and Reaction Scheme I:

(S)-tert-butyl 4-(2-(1-(3-amino-5,6-dimethylpyrazine-2-carboxamido)ethyl)-5-chloro-4-oxoquinazolin-3(4H)-yl)piperazine-1-carboxylate;

(S)-tert-butyl 4-(2-(1-(2-aminopyrazolo[1,5-a]pyrimidine-3-carboxamido)ethyl)-5-chloro-4-oxoquinazolin-3(4H)-yl)piperazine-1-carboxylate;

(S)-tert-butyl 4-(5-chloro-2-(1-(3,5-diamino-6-chloropyrazine-2-carboxamido)ethyl)-4-oxoquinazolin-3(4H)-yl)piperazine-1-carboxylate; and (S)-tert-butyl 4-(2-(1-(3-amino-6-chloropyrazine-2-carboxamido)ethyl)-5-chloro-4-oxoquinazolin-3(4H)-yl)piperazine-1-carboxylate.

Example 4. Preparation of a Compound of Formula (I)

A. Preparation of a compound of formula (I), where n is 1, $R^1$ is chloro, B is 4,7-diazaspiro[2.5]octanyl, m is 0, $R^5$ is hydrogen, A is a single bond, $R^3$ is methyl, and $R^4$ is 2,6-diamino-5-cyanopyrimidin-4-yl

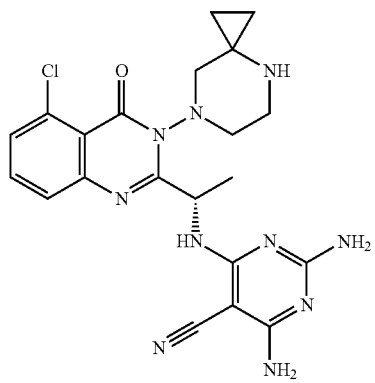 [SMILES: C[C@H](Nc1nc(N)nc(N)c1C#N)c1nc2cccc(Cl)c2c(=O)n1N1CCNC2(CC2)C1]

To a solution of (S)-tert-butyl 7-(5-chloro-2-(1-((2,6-diamino-5-cyanopyrimidin-4-yl)amino)ethyl)-4-oxoquinazolin-3(4H)-yl)-4,7-diazaspiro[2.5]octane-4-carboxylate (130 mg, 0.23 mmol) in dichloromethane (1 mL) was added trifluoroacetic acid (1 mL). The reaction solution stirred for 2 hours and was concentrated. The residue was purified on a reverse phase HPLC system run from 0 to 95% ACN in water (0.1% TFA) to give (S)-2,4-diamino-6-((1-(5-chloro-4-oxo-3-(4,7-diazaspiro[2.5]octan-7-yl)-3,4-dihydroquinazolin-2-yl)ethyl)amino)pyrimidine-5-carbonitrile. (Compound 7).

Exists as a ~1:1 mixture of rotamers. 1H NMR (400 MHz, DMSO-d6) δ 9.54-9.34 (m, 1H), 8.87 (s, 0.5H), 8.66 (s, 0.5H), 7.76-7.68 (m, 1H), 7.60-7.50 (m, 2H), 5.71-5.55 (m, 1H), 4.50 (dd, J=17.1, 12.1 Hz, 1H), 4.25-4.07 (m, 1H), 3.54 (d, J=11.7 Hz, 0.5H), 3.42 (t, J=11.8, 11.3 Hz, 1H), 3.32 (d, J=11.9 Hz, 0.5H), 3.27-3.15 (m, 0.5H), 76 (dd, J=18.0, 12.0 Hz, 1H), 1.47 (d, J=6.8 Hz, 1.5H), 1.44 (d, J=6.7 Hz, 1.5H), 1.13-0.88 (m, 3H). ES/MS 467.1 (M+H$^+$).

B. Preparation of the below compounds of formula (I), using the procedures described in Example 4A and Reaction Scheme I:

2,4-diamino-6-(((S)-1-(3-((S)-azepan-4-yl)-5-chloro-4-oxo-3,4-dihydroquinazolin-2-yl)ethyl)amino)pyrimidine-5-carbonitrile (Compound 8). $^1$H NMR (400 MHz, DMSO-d$_6$) δ 8.64 (bs, 2H), 7.84 (bs, 1H), 7.74 (dd, J=8.2, 7.8 Hz, 1H), 7.59 (dd, J=8.2, 1.2 Hz, 1H), 7.55 (dd, J=7.8, 1.2 Hz, 1H), 7.38 (bs, 2H), 7.19 (bs, 1H), 5.62 (m, 1H), 4.28 (m, 1H), 3.45 (m, 1H), 3.12 (m, 2H), 2.84 (m, 1H), 2.69-2.52 (m, 2H), 2.17-1.86 (m, 3H), 1.65 (m, 1H), 1.52 (d, J=6.4 Hz, 3H). ES/MS 454.2 (M+H$^+$).

2,4-diamino-6-(((S)-1-(3-((R)-azepan-4-yl)-5-chloro-4-oxo-3,4-dihydroquinazolin-2-yl)ethyl)amino)pyrimidine-5-carbonitrile (Compound 9). $^1$H NMR (400 MHz, DMSO-d$_6$) δ 8.69 (bs, 1H), 8.61 (bs, 1H), 7.84 (bs, 1H), 7.75 (dd, J=8.0 Hz, 1H), 7.59 (dd, J=8.2, 1.2 Hz, 1H), 7.55 (dd, J=7.8, 1.2 Hz, 1H), 7.28 (bs, 2H), 7.11 (bs, 2H), 5.63 (m, 1H), 4.26 (m, 1H), 3.48 (m, 1H), 3.07 (m, 3H), 2.77 (m, 1H), 2.50 (m, 1H), 2.14 (m, 1H), 1.93 (m, 2H), 1.52 (d, J=6.4 Hz, 3H), 1.44 (m, 1H). ES/MS 454.2 (M+H$^+$).

2-amino-4-(((S)-1-(3-((S)-azepan-4-yl)-5-chloro-4-oxo-3,4-dihydroquinazolin-2-yl)ethyl)amino)-6-methylpyrimidine-5-carbonitrile (Compound 10). $^1$H NMR (400 MHz, DMSO-d$_6$) δ 8.61 (bs, 2H), 8.09 (d, J=7.8 Hz, 1H), 7.74 (dd, J=8.0 Hz, 1H), 7.59 (dd, J=8.2, 1.2 Hz, 1H), 7.55 (dd, J=7.8, 1.2 Hz, 1H), 7.36 (bs, 1H), 5.60 (m, 1H), 4.24 (m, 1H), 3.44 (m, 1H), 3.12 (m, 2H), 2.85 (m, 1H), 2.71-2.52 (m, 2H), 2.32 (s, 3H), 2.03 (m, 3H), 1.63 (m, 1H), 1.53 (d, J=6.4 Hz, 3H). ES/MS 453.2 (M+H$^+$).

2-amino-4-(((S)-1-(3-((R)-azepan-4-yl)-5-chloro-4-oxo-3,4-dihydroquinazolin-2-yl)ethyl)amino)-6-methylpyrimidine-5-carbonitrile (Compound 11). $^1$H NMR (400 MHz, DMSO-d$_6$) δ 8.63 (br, 2H), 8.09 (d, J=7.8 Hz, 1H), 7.74 (dd, J=8.2, 7.8 Hz, 1H), 7.59 (dd, J=8.2, 1.2 Hz, 1H), 7.55 (dd, J=7.8, 1.2 Hz, 1H), 7.54-7.12 (br, 2H), 5.63 (m, 1H), 4.21 (m, 1H), 3.48 (m, 1H), 3.06 (m, 3H), 2.76 (m, 1H), 2.50 (m, 1H), 2.31 (s, 3H), 2.14 (m, 1H), 1.93 (m, 2H), 1.54 (d, J=6.3 Hz, 3H), 1.36 (m, 1H). ES/MS 453.2 (M+H$^+$).

3-((S)-azepan-4-yl)-5-chloro-2-((S)-1-((2,6-diamino-5-chloropyrimidin-4-yl)amino)ethyl)quinazolin-4(3H)-one (Compound 12). $^1$H NMR (400 MHz, DMSO-d$_6$) δ 8.68 (br, 2H), 7.88 (bs, 1H), 7.75 (dd, J=8.0 Hz, 1H), 7.60 (dd, J=8.2, 1.2 Hz, 1H), 7.56 (dd, J=7.8, 1.2 Hz, 1H), 7.52 (bs, 4H), 5.54 (m, 1H), 4.24 (m, 1H), 3.43 (m, 1H), 3.15 (m, 2H), 2.94 (m, 1H), 2.62-2.52 (m, 2H), 2.17-1.87 (m, 3H), 1.64 (m, 1H), 1.54 (d, J=6.4 Hz, 3H). ES/MS 463.1 (M+H$^+$).

3-((R)-azepan-4-yl)-5-chloro-2-((S)-1-((2,6-diamino-5-chloropyrimidin-4-yl)amino)ethyl)quinazolin-4(3H)-one (Compound 13). $^1$H NMR (400 MHz, DMSO-d$_6$) δ 8.69 (br, 2H), 7.85 (bs, 1H), 7.74 (dd, J=8.2, 7.8 Hz, 1H), 7.60 (dd, J=8.2, 1.2 Hz, 1H), 7.56 (dd, J=7.8, 1.2 Hz, 1H), 7.43 (bs, 2H), 5.56 (m, 1H), 4.24 (m, 1H), 3.48 (m, 1H), 3.06 (m, 3H), 2.74 (m, 1H), 2.46 (m, 1H), 2.15 (m, 1H), 1.92 (m, 2H), 1.54 (d, J=6.4 Hz, 3H), 1.44 (m, 1H). ES/MS 463.1 (M+H$^+$).

4-(((1S)-3-((1R,5S)-3-azabicyclo[3.1.0]hexan-6-yl)-5-chloro-4-oxo-3,4-dihydroquinazolin-2-yl)(cyclopropyl)methyl)amino)-2-amino-6-methylpyrimidine-5-carbonitrile (Compound 14). $^1$H NMR (400 MHz, DMSO-d$_6$) δ 9.24 (bs, 1H), 8.76 (bs, 1H), 7.78 (dd, J=8.0, 8.4 Hz, 1H), 7.61 (m, 2H), 7.49 (bs, 2H), 5.38 (dd, J=7.9 Hz, 1H), 3.66 (dd, J=11.8, 5.7 Hz, 1H), 3.63-3.46 (m, 3H), 2.88 (m, 1H), 2.43 (m, 1H), 2.38 (m, 1H), 2.35 (s, 3H), 1.55 (m, 1H), 0.74 (m, 1H), 0.58 (m, 2H), 0.53 (m, 1H). ES/MS 463.2 (M+H$^+$).

4-(((1S)-3-((1R,5S)-3-azabicyclo[3.1.0]hexan-6-yl)-5-chloro-4-oxo-3,4-dihydroquinazolin-2-yl)(cyclopropyl)methyl)amino)-2,6-diaminopyrimidine-5-carbonitrile (Compound 15). $^1$H NMR (400 MHz, DMSO-d$_6$) δ 9.35 (bs, 1H), 8.78 (bs, 1H), 7.78 (t, J=8.0 Hz, 1H), 7.61 (m, 2H), 7.46 (bs, 2H), 7.22 (bs, 3H), 5.38 (t, J=8.1 Hz, 1H), 3.69 (dd, J=12.1, 5.8 Hz, 1H), 3.62 (dd, J=11.8, 5.9 Hz, 1H), 3.52 (m, 2H), 2.88 (t, J=2.7 Hz, 1H), 2.39 (m, 2H), 1.53 (m, 1H), 0.71 (m, 1H), 0.59 (m, 2H), 0.52 (m, 1H). ES/MS 464.1 (M+H$^+$).

4-(((1S)-1-(3-((1R,5S)-3-azabicyclo[3.1.0]hexan-6-yl)-5-chloro-8-fluoro-4-oxo-3,4-dihydroquinazolin-2-yl)ethyl)amino)-2-amino-6-methylpyrimidine-5-carbonitrile (Compound 16). $^1$H NMR (400 MHz, DMSO-d$_6$) δ 9.21 (bs, 1H), 8.76 (bs, 1H), 7.77 (bs, 1H), 7.73 (dd, J=9.6, 8.8 Hz, 1H), 7.59 (dd, J=8.8, 4.4 Hz, 1H), 7.40 (bs, 2H), 5.86 (m, 1H), 3.64 (m, 1H), 3.60-3.42 (m, 4H), 2.92 (t, J=2.8 Hz, 1H), 2.34 (s, 3H), 2.32 (m, 1H), 1.55 (d, J=6.5 Hz, 3H). ES/MS 455.1 (M+H$^+$).

4-(((1S)-1-(3-((1R,5S)-3-azabicyclo[3.1.0]hexan-6-yl)-5-chloro-8-fluoro-4-oxo-3,4-dihydroquinazolin-2-yl)ethyl)amino)-2,6-diaminopyrimidine-5-carbonitrile (Compound 17). $^1$H NMR (400 MHz, DMSO-d$_6$) δ 9.22 (bs, 1H), 8.73 (bs, 1H), 7.67 (dd, J=8.8, 9.6 Hz, 1H), 7.53 (dd, J=8.7, 4.4 Hz, 1H), 7.52 (bs, 1H), 7.35 (bs, 2H), 7.19 (bs, 2H), 5.78 (m, 1H), 3.59 (dd, J=11.9, 5.8 Hz, 1H), 3.50 (m, 4H), 2.86 (m, 1H), 2.33 (m, 1H), 1.48 (d, J=6.5 Hz, 3H). ES/MS 456.3 (M+H$^+$).

(S)-5-chloro-3-(piperidin-4-yl)-2-(1-(thiazolo[5,4-d]pyrimidin-7-ylamino)ethyl)quinazolin-4(3H)-one (Compound 18). $^1$H NMR (400 MHz, DMSO-d$_6$) δ 9.37 (s, 1H), 8.88 (d, J=7.2 Hz, 1H), 8.60 (br, 1H), 8.53 (s, 1H), 8.44 (br, 1H), 7.75 (t, J=8.0 Hz, 1H), 7.58 (m, 2H), 5.84 (m, 1H), 4.53 (m, 1H), 3.46 (m, 1H), 3.28 (m, 1H), 3.10 (m, 4H), 1.99 (m, 2H), 1.69 (d, J=6.5 Hz, 3H). ES/MS 442.2 (M+H$^+$).

4-(((1S)-1-(3-((1R,5S)-3-azabicyclo[3.1.0]hexan-6-yl)-5-chloro-4-oxo-3,4-dihydroquinazolin-2-yl)ethyl)amino)-2,6-diaminopyrimidine-5-carbonitrile (Compound 19). $^1$H NMR (400 MHz, DMSO-d$_6$) δ 9.27 (bs, 1H), 8.75 (bs, 1H), 7.73 (dd, J=8.2, 7.8 Hz, 1H), 7.56 (m, 2H), 5.78 (m, 1H), 3.62 (m, 1H), 3.51 (m, 4H), 2.86 (m, 1H), 2.30 (m, 1H), 1.50 (d, J=6.5 Hz, 3H). ES/MS 438.1 (M+H$^+$).

(S)-5-chloro-2-(1-((2,6-diamino-5-chloropyrimidin-4-yl)amino)ethyl)-8-fluoro-3-(piperazin-1-yl)quinazolin-4(3H)-one (Compound 20). $^1$H NMR (400 MHz, DMSO-d$_6$) δ 9.07 (d, J=10.4 Hz, 1H), 8.73 (br, 1H), 7.73 (dd, J=9.6, 8.7 Hz, 1H), 7.59 (m, 1H), 7.55 (bs, 2H), 7.43 (bs, 2H), 5.58 (m, 1H), 4.10 (m, 2H), 3.35 (m, 4H), 3.03 (m, 1H), 2.78 (m, 1H), 1.51 (d, J=6.7 Hz, 3H). ES/MS 468.1 (M+H$^+$).

(S)-2-amino-4-((1-(5-chloro-8-fluoro-4-oxo-3-(piperazin-1-yl)-3,4-dihydroquinazolin-2-yl)ethyl)amino)-6-methylpyrimidine-5-carbonitrile (Compound 21). $^1$H NMR (400 MHz, DMSO-d$_6$) δ 9.03 (d, J=10.9 Hz, 1H), 8.67 (m, 1H), 7.95 (bs, 1H), 7.73 (dd, J=9.6, 8.7 Hz, 1H), 7.58 (m, 1H), 7.56-7.29 (br, 1H), 5.67 (m, 1H), 4.10 (dt, J=12.5, 9.6 Hz, 2H), 3.35 (m, 4H), 3.05 (m, 1H), 2.68 (m, 1H), 2.32 (s, 3H), 1.51 (d, J=6.7 Hz, 3H). ES/MS 458.1 (M+H$^+$).

(S)-2,4-diamino-6-((1-(5-chloro-4-oxo-3-(piperidin-4-yl)-3,4-dihydroquinazolin-2-yl)propyl)amino)pyrimidine-5- carbonitrile (Compound 22). ¹H NMR (400 MHz, DMSO-d₆) δ 8.80 (d, J=11.1 Hz, 1H), 8.46 (m, 1H), 7.75 (dd, J=8.2, 7.8 Hz, 1H), 7.70 (br, 1H), 7.62-7.54 (m, 2H), 7.38 (br, 1H), 5.54 (td, J=8.4, 5.2 Hz, 1H), 4.38 (m, 1H), 3.43 (m, 2H), 3.16-2.81 (m, 3H), 2.35 (m, 1H), 2.12 (m, 1H), 1.95 (m, 2H), 1.72 (d, J=13.2 Hz, 1H), 0.96 (t, J=7.3 Hz, 3H). ES/MS 454.2 (M+H⁺).

(S)-2-amino-4-((1-(5-chloro-4-oxo-3-(piperidin-4-yl)-3,4-dihydroquinazolin-2-yl)propyl)amino)-6-methylpyrimidine-5-carbonitrile (Compound 23). ¹H NMR (400 MHz, DMSO-d₆) δ 8.75 (d, J=10.9 Hz, 1H), 8.44 (m, 1H), 7.90 (d, J=8.3 Hz, 1H), 7.75 (dd, J=8.2, 7.8 Hz, 1H), 7.62-7.55 (m, 2H), 7.48-7.30 (br, 1H), 5.55 (td, J=8.4, 5.0 Hz, 1H), 4.31 (m, 1H), 3.56-3.25 (m, 2H), 3.21-2.76 (m, 3H), 2.31 (s, 3H), 2.29-2.20 (m, 1H), 2.19-2.05 (m, 1H), 2.05-1.88 (m, 2H), 1.71 (d, J=13.2 Hz, 1H), 0.97 (t, J=7.3 Hz, 3H). ES/MS 453.2 (M+H⁺).

(S)-2-amino-4-((1-(5-chloro-4-oxo-3-(piperidin-4-yl)-3,4-dihydroquinazolin-2-yl)ethyl)amino)-6-methylpyrimidine-5-carbonitrile (Compound 24). ¹H NMR (400 MHz, DMSO-d₆) δ 9.40 (m, 1H), 8.89 (s, 1H), 8.63 (br, 1H), 8.39 (bs, 1H), 7.76 (dd, J=8.4, 7.7 Hz, 1H), 7.59 (m, 1H), 7.57 (m, 1H), 5.65 (m, 1H), 4.23 (br, 1H), 3.39 (m, 2H), 3.18-2.84 (m, 3H), 2.65 (m, 1H), 2.44 (s, 3H), 1.91 (m, 1.5H), 1.58 (d, J=6.4 Hz, 3H), 1.37-1.22 (m, 0.5H). ES/MS 439.2 (M+H⁺).

(S)-5-chloro-2-(1-((2,6-diamino-5-chloropyrimidin-4-yl)amino)ethyl)-3-(piperidin-4-yl)quinazolin-4(3H)-one (Compound 25). ¹H NMR (400 MHz, DMSO-d₆) δ 9.34 (s, 1H), 8.65 (d, J=11.5 Hz, 1H), 7.86 (bs, 2H), 7.76 (t, J=8.0 Hz, 1H), 7.60 (d, J=8.0 Hz, 1H), 7.57 (dd, J=7.8, 1.2 Hz, 1H), 5.63 (bs, 1H), 4.42 (br, 2H), 3.40 (m, 2H), 3.03 (m, 4H), 1.95 (m, 1H), 1.86 (bs, 1H), 1.55 (d, J=6.4 Hz, 3H), 1.40-1.23 (m, 1H). ES/MS 449.1 (M+H⁺).

(S)-2,4-diamino-6-((1-(5-chloro-4-oxo-3-(piperidin-4-yl)-3,4-dihydroquinazolin-2-yl)ethyl)amino)pyrimidine-5-carbonitrile (Compound 26). ¹H NMR (400 MHz, DMSO-d₆) δ 9.41 (d, J=10.7 Hz, 1H), 8.68 (d, J=11.4 Hz, 1H), 8.49 (bs, 3H), 8.30 (bs, 2H), 7.77 (dd, J=8.4, 7.6 Hz, 1H), 7.67-7.47 (m, 2H), 5.68 (m, 1H), 4.26 (m, 1H), 3.41 (m, 2H), 3.09-2.86 (m, 2H), 1.92 (m, 2H), 1.55 (d, J=6.4 Hz, 3H), 1.41-1.18 (m, 4H). ES/MS 440.2 (M+H⁺).

2,4-diamino-6-(((S)-1-(5-chloro-4-oxo-3-((R)-piperidin-3-yl)-3,4-dihydroquinazolin-2-yl)ethyl)amino)pyrimidine-5-carbonitrile (Compound 27). 1H NMR (400 MHz, DMSO-d₆) δ 9.01 (d, J=10.1 Hz, 1H), 8.70-8.51 (m, 1H), 7.72 (t, 1H), 7.54 (t, J=1.2 Hz, 1H), 7.52 (d, J=1.4 Hz, 1H), 7.28 (s, 2H), 6.96 (s, 2H), 5.48 (p, J=6.7 Hz, 1H), 4.34 (d, J=12.1 Hz, 1H), 4.10-3.90 (m, 1H), 3.73 (t, J=5.4 Hz, 1H), 3.27 (d, J=12.6 Hz, 1H), 2.96-2.76 (m, 1H), 2.71-2.54 (m, 1H), 1.89 (d, J=12.1 Hz, 2H), 1.69-1.40 (m, 4H). ES/MS 440.2 (M+H⁺).

2,4-diamino-6-(((S)-1-(5-chloro-4-oxo-3-((S)-piperidin-3-yl)-3,4-dihydroquinazolin-2-yl)ethyl)amino)pyrimidine-5-carbonitrile (Compound 28). 1H NMR (400 MHz, DMSO-d₆) δ 8.97 (d, J=11.1 Hz, 1H), 8.58 (d, J=11.5 Hz, 1H), 7.78-7.67 (m, 1H), 7.59-7.50 (m, 2H), 7.25-7.18 (m, 2H), 6.89 (s, 2H), 5.47 (p, J=6.7 Hz, 1H), 4.36 (t, J=11.4 Hz, 1H), 4.00 (q, J=11.2 Hz, 1H), 3.32-3.20 (m, 1H), 2.87 (q, J=12.4 Hz, 1H), 2.62 (q, J=14.5, 11.7 Hz, 1H), 1.89 (d, J=12.6 Hz, 2H), 1.64-1.41 (m, 4H). ES/MS 440.2 (M+H⁺).

(S)-2,4-diamino-6-((1-(3-(azetidin-3-yl)-5-chloro-4-oxo-3,4-dihydroquinazolin-2-yl)ethyl)amino)pyrimidine-5-carbonitrile (Compound 29). 1H NMR (400 MHz, DMSO-d₆) δ 8.01 (t, J=6.6 Hz, 1H), 7.98-7.88 (m, 1H), 7.85-7.69 (m, 1H), 7.57-7.46 (m, 2H), 7.38 (d, J=13.0 Hz, 1H), 7.29-7.10 (m, 1H), 7.10-6.94 (m, 1H), 5.51-5.34 (m, 1H), 1.61-1.51 (m, 4H), 1.49 (d, J=6.4 Hz, 2H), 1.44 (d, J=6.3 Hz, 2H). ES/MS 412.1 (M+H⁺).

2,4-diamino-6-(((S)-1-chloro-4-oxo-3-((S)-pyrrolidin-3-yl)-3,4-dihydroquinazolin-2-yl)ethyl)amino)pyrimidine-5-carbonitrile (Compound 30). 1H NMR (400 MHz, DMSO-d₆) δ 9.01 (s, 1H), 8.61 (dt, J=11.8, 7.0 Hz, 1H), 7.76 (t, J=8.0 Hz, 1H), 7.66 (s, 1H), 7.58 (t, J=7.8 Hz, 2H), 7.31 (s, 2H), 7.10 (s, 2H), 5.54 (p, J=6.3 Hz, 1H), 4.99 (tq, J=8.0, 4.0 Hz, 1H), 3.27-3.05 (m, 3H), 2.39-2.22 (m, 2H), 1.50 (d, J=6.3 Hz, 3H). ES/MS 426.2 (M+H⁺).

2,4-diamino-6-(((S)-1-(5-chloro-4-oxo-3-((R)-pyrrolidin-3-yl)-3,4-dihydroquinazolin-2-yl)ethyl)amino)pyrimidine-5-carbonitrile (Compound 31). 1H NMR (400 MHz, DMSO-d₆) δ 9.13-8.93 (m, 1H), 8.60 (dd, J=11.8, 6.2 Hz, 1H), 7.74 (q, J=6.9, 5.9 Hz, 2H), 7.58 (t, J=8.5 Hz, 2H), 7.31 (s, 2H), 7.09 (s, 2H), 5.57 (p, J=6.6 Hz, 1H), 5.00 (tt, J=9.6, 4.9 Hz, 1H), 3.40-3.31 (m, 2H), 3.19-3.03 (m, 1H), 2.29 (ddd, J=14.0, 9.3, 5.4 Hz, 1H), 2.15 (dtd, J=13.4, 8.8, 4.4 Hz, 1H), 1.50 (d, J=6.3 Hz, 3H). ES/MS 426.2 (M+H⁺).

(S)-3-amino-6-chloro-N-(1-(5-chloro-4-oxo-3-(piperazin-1-yl)-3,4-dihydroquinazolin-2-yl)ethyl)pyrazine-2-carboxamide (Compound 32). 1H NMR (400 MHz, DMSO-d₆) δ 9.26 (d, J=10.9 Hz, 1H), 9.03 (d, J=7.4 Hz, 1H), 8.80 (q, J=10.8, 10.3 Hz, 1H), 8.36 (dd, J=1.1, 0.6 Hz, 1H), 7.76 (q, J=13.7, 10.8 Hz, 3H), 7.59 (ddd, J=10.0, 8.0, 1.2 Hz, 2H), 5.51 (p, J=6.8 Hz, 1H), 4.23-4.00 (m, 2H), 3.39-3.27 (m, 1H), 3.27-3.13 (m, 2H), 3.04 (td, J=17.5, 15.3, 8.3 Hz, 1H), 1.53 (d, J=6.6 Hz, 3H), 1.26-1.18 (m, 1H). ES/MS 463.1 (M+H⁺).

(S)-3,5-diamino-6-chloro-N-(1-(5-chloro-4-oxo-3-(piperazin-1-yl)-3,4-dihydroquinazolin-2-yl)ethyl)pyrazine-2-carboxamide (Compound 33). 1H NMR (400 MHz, DMSO-d₆) δ 8.94 (d, J=11.0 Hz, 1H), 8.63 (d, J=11.7 Hz, 1H), 8.31 (d, J=7.8 Hz, 1H), 7.76 (t, J=8.0 Hz, 1H), 7.58 (ddd, J=12.3, 8.0, 1.2 Hz, 2H), 7.11 (s, 3H), 5.56-5.41 (m, 1H), 4.21-4.02 (m, 2H), 3.40 (dd, J=21.6, 12.2 Hz, 2H), 3.27 (dd, J=17.0, 12.0 Hz, 3H), 3.17-3.00 (m, 1H), 1.49 (d, J=6.7 Hz, 3H), 1.04 (d, J=6.1 Hz, 1H). ES/MS 478.1 (M+H⁺).

(S)-5-chloro-2-(1-(furo[3,2-d]pyrimidin-4-ylamino)ethyl)-3-(piperazin-1-yl)quinazolin-4(3H)-one (Compound 34). 1H NMR (400 MHz, DMSO-d₆) δ 9.08 (s, 1H), 8.88 (d, J=11.0 Hz, 1H), 8.60 (d, J=11.6 Hz, 1H), 8.41 (s, 1H), 8.36 (d, J=2.2 Hz, 1H), 7.67 (t, J=8.0 Hz, 1H), 7.49 (ddd, J=11.3, 8.0, 1.2 Hz, 2H), 7.04 (d, J=2.2 Hz, 1H), 5.90 (p, J=6.8 Hz, 1H), 4.13 (dtd, J=18.7, 12.4, 2.8 Hz, 2H), 3.42 (t, J=12.0 Hz, 2H), 3.32 (d, J=12.3 Hz, 2H), 3.12 (d, J=12.2 Hz, 1H), 2.98-2.75 (m, 1H), 1.56 (d, J=6.8 Hz, 3H). ES/MS 426.2 (M+H⁺).

(S)-5-chloro-2-(1-((5-chlorothieno[2,3-d]pyrimidin-4-yl)amino)ethyl)-3-(piperazin-1-yl)quinazolin-4(3H)-one (Compound 35) 1H NMR (400 MHz, DMSO-d₆) δ 8.80 (d, J=11.0 Hz, 1H), 8.50 (d, J=7.1 Hz, 1H), 8.31 (s, 1H), 7.80 (d, J=0.7 Hz, 1H), 7.68 (td, J=8.0, 0.7 Hz, 1H), 7.51 (ddt, J=8.1, 4.4, 1.0 Hz, 2H), 5.88 (p, J=6.9 Hz, 1H), 4.20-4.00 (m, 2H), 3.44-3.36 (m, 2H), 3.36-3.25 (m, 2H), 3.18-2.98 (m, 1H), 2.85-2.66 (m, 1H), 1.53 (d, J=6.8 Hz, 3H). ES/MS 476.1 (M+H⁺).

(S)-2-amino-N-(1-(5-chloro-4-oxo-3-(piperazin-1-yl)-3,4-dihydroquinazolin-2-yl)ethyl)pyrazolo[1,5-a]pyrimidine-3-carboxamide (Compound 36) 1H NMR (400 MHz, DMSO-d₆) δ 9.00-8.85 (m, 2H), 8.77-8.51 (m, 3H), 7.76 (t, J=8.0 Hz, 1H), 7.64 (dd, J=8.1, 1.1 Hz, 1H), 7.57 (dd, J=7.9, 1.1 Hz, 1H), 7.03 (dd, J=6.8, 4.5 Hz, 1H), 6.52 (s, 2H), 5.71 (p, J=6.8 Hz, 1H), 4.21 (td, J=12.0, 11.6, 2.8 Hz, 1H), 4.08

(td, J=12.1, 11.5, 2.7 Hz, 1H), 3.43 (dd, J=16.1, 12.6 Hz, 2H), 3.38-3.28 (m, 2H), 3.21 (dd, J=22.9, 11.6 Hz, 2H), 1.53 (d, J=6.7 Hz, 3H). ES/MS 468.2 (M+H$^+$).

(S)-2-(1-((6-amino-5-chloropyrimidin-4-yl)amino)ethyl)-5-chloro-3-(piperazin-1-yl)quinazolin-4(3H)-one (Compound 37). 1H NMR (400 MHz, DMSO-d$_6$) δ 8.86 (d, J=10.9 Hz, 1H), 8.72-8.50 (m, 1H), 7.97 (s, 1H), 7.81-7.66 (m, 1H), 7.63-7.45 (m, 2H), 7.23 (d, J=7.6 Hz, 1H), 6.94 (s, 2H), 5.71 (p, J=6.8 Hz, 1H), 4.21-4.01 (m, 2H), 3.48-3.25 (m, 3H), 3.09 (q, J=11.4 Hz, 1H), 2.82 (t, J=11.7 Hz, 1H), 1.51 (d, J=6.7 Hz, 3H). ES/MS 435.1 (M+H$^+$).

2,4-diamino-6-(((1S)-1-(5-chloro-3-(3,3-difluoropiperidin-4-yl)-4-oxo-3,4-dihydroquinazolin-2-yl)ethyl)amino)pyrimidine-5-carbonitrile (Compound 38). 1H NMR (400 MHz, DMSO-d$_6$) δ 10.37 (s, 1H), 9.82-9.52 (m, 1H), 8.23 (d, J=94.7 Hz, 3H), 7.81 (tt, J=8.0, 2.7 Hz, 1H), 7.63 (dtd, J=8.4, 6.4, 5.1 Hz, 2H), 5.71-5.52 (m, 1H), 4.69 (s, 1H), 4.12-3.88 (m, 1H), 3.58 (d, 4H), 2.89-2.61 (m, 1H), 2.29-2.08 (m, 1H), 1.65-1.39 (m, 3H). ES/MS 476.2 (M+H$^+$).

(S)-2,4-diamino-6-((1-(5,8-difluoro-4-oxo-3-(piperazin-1-yl)-3,4-dihydroquinazolin-2-yl)ethyl)amino)pyrimidine-5-carbonitrile (Compound 39). 1H NMR (400 MHz, DMSO-d$_6$) δ 9.45 (s, 1H), 8.89 (d, J=12.2 Hz, 1H), 8.20 (s, 3H), 7.78 (td, J=9.4, 4.1 Hz, 1H), 7.48-7.22 (m, 1H), 5.65 (s, 1H), 4.22-3.99 (m, 3H), 3.81-3.67 (m, 1H), 3.48-3.14 (m, 4H), 2.90 (dd, J=113.3, 21.6 Hz, 1H), 1.51 (d, J=6.6 Hz, 3H). ES/MS 443.2 (M+H$^+$).

(S)-5,8-difluoro-2-(1-(imidazo[2,1-f][1,2,4]triazin-4-ylamino)ethyl)-3-(piperazin-1-yl)quinazolin-4(3H)-one (Compound 40). 1H NMR (400 MHz, DMSO-d$_6$) δ 9.41 (d, J=11.5 Hz, 1H), 9.34 (d, J=6.6 Hz, 1H), 8.90 (dq, J=21.8, 11.3, 9.6 Hz, 1H), 8.11 (d, 2H), 7.78-7.59 (m, 2H), 7.33-7.19 (m, 1H), 5.94-5.73 (m, J=6.7 Hz, 1H), 4.18-3.97 (m, 2H), 3.46-3.20 (m, 4H), 3.12 (q, J=11.4 Hz, 1H), 2.90 (q, J=12.3 Hz, 1H), 1.59 (d, J=6.8, 1.3 Hz, 3H). ES/MS 428.2 (M+H$^+$).

(S)-2-(cyclopropyl(imidazo[2,1-f][1,2,4]triazin-4-ylamino)methyl)-5,8-difluoro-3-(piperazin-1-yl)quinazolin-4(3H)-one (Compound 41). 1H NMR (400 MHz, DMSO-d$_6$) δ 9.25 (dd, J=22.3, 9.2 Hz, 2H), 8.76 (d, J=13.2 Hz, 1H), 8.23-7.97 (m, 2H), 7.83-7.57 (m, 2H), 7.41-7.13 (m, 1H), 5.23 (s, 1H), 4.11 (ddd, J=33.4, 13.3, 10.3 Hz, 2H), 3.53 (d, J=1.2 Hz, 2H), 3.44-3.12 (m, 4H), 1.76-1.44 (m, 1H), 0.81-0.27 (m, 3H). ES/MS 454.2 (M+H$^+$).

(S)-5-chloro-2-(1-(imidazo[2,1-f][1,2,4]triazin-4-ylamino)propyl)-3-(piperazin-1-yl)quinazolin-4(3H)-one (Compound 42). 1H NMR (400 MHz, DMSO-d$_6$) δ 9.33 (d, J=11.7 Hz, 1H), 9.26 (s, 0H), 8.88 (dt, J=22.5, 11.1 Hz, 1H), 8.21-8.01 (m, 2H), 7.76-7.61 (m, 2H), 7.58-7.40 (m, 2H), 5.70 (q, J=7.0 Hz, 1H), 4.37-3.97 (m, 2H), 3.58-3.47 (m, 3H), 3.41-3.30 (m, 1H), 3.24 (d, J=12.3 Hz, 1H), 3.10 (dq, J=23.0, 11.3 Hz, 2H), 2.13-1.90 (m, 2H), 1.06 (t, 3H). ES/MS 440.2 (M+H$^+$).

(S)-5-chloro-2-(cyclopropyl(imidazo[2,1-f][1,2,4]triazin-4-ylamino)methyl)-3-(piperazin-1-yl)quinazolin-4(3H)-one (Compound 43). 1H NMR (400 MHz, DMSO-d$_6$) δ 9.41 (d, J=11.4 Hz, 1H), 9.34-9.14 (m, 1H), 8.82 (d, J=12.0 Hz, 1H), 8.21-8.00 (m, 2H), 7.77-7.62 (m, 2H), 7.55 (ddt, J=16.7, 7.8, 1.1 Hz, 2H), 5.22 (s, 2H), 4.14 (ddd, J=35.2, 13.7, 10.7 Hz, 2H), 3.45-3.20 (m, 3H), 3.15 (d, J=12.1 Hz, 0H), 3.02 (s, 1H), 1.68-1.47 (m, 1H), 0.72-0.51 (m, 3H), 0.51 (s, 1H). ES/MS 452.2 (M+H$^+$).

(S)-2-amino-4-((1-(5-chloro-4-oxo-3-(piperazin-1-yl)-3,4-dihydroquinazolin-2-yl)propyl)amino)-6-methylpyrimidine-5-carbonitrile (Compound 44). 1H NMR (400 MHz, DMSO-d$_6$) δ 9.29 (d, J=11.1 Hz, 1H), 8.86 (d, J=12.3 Hz, 1H), 8.24 (d, J=78.3 Hz, 1H), 7.80-7.63 (m, 1H), 7.63-7.42 (m, 2H), 5.52-5.30 (m, 1H), 4.27-3.96 (m, 2H), 3.26 (d, J=13.2 Hz, 3H), 3.08-2.75 (m, 1H), 2.36 (s, 3H), 2.07-1.79 (m, J=6.7, 6.3 Hz, 2H), 1.09-0.86 (m, 3H). ES/MS 454.2 (M+H$^+$).

(S)-2-amino-4-(((5-chloro-4-oxo-3-(piperazin-1-yl)-3,4-dihydroquinazolin-2-yl)(cyclopropyl)methyl)amino)-6-methylpyrimidine-5-carbonitrile (Compound 46). 1H NMR (400 MHz, DMSO-d$_6$) δ 9.40 (d, J=10.4 Hz, 1H), 8.82 (d, J=11.6 Hz, 1H), 8.49 (s, 2H), 7.87-7.69 (m, 1H), 7.59 (ddt, J=16.8, 7.8, 1.5 Hz, 2H), 5.19 (t, J=8.1 Hz, 1H), 4.20-4.04 (m, 2H), 3.53 (d, J=1.7 Hz, 0H), 3.36 (d, J=12.5 Hz, 1H), 3.25 (t, J=14.5 Hz, 2H), 3.05 (d, J=12.2 Hz, 2H), 2.52 (h, J=1.9 Hz, 1H), 2.42 (q, J=1.9 Hz, 1H), 2.40-2.38 (m, 2H), 1.68-1.46 (m, 1H), 0.71-0.43 (m, 3H), 0.36 (dq, J=8.3, 4.1 Hz, 1H). ES/MS 466.2 (M+H$^+$).

(S)-5-chloro-2-(cyclopropyl(imidazo[2,1-f][1,2,4]triazin-4-ylamino)methyl)-8-fluoro-3-(piperazin-1-yl)quinazolin-4(3H)-one (Compound 47). 1H NMR (400 MHz, DMSO-d$_6$) δ 9.35 (d, J=10.5 Hz, 1H), 9.24 (d, J=6.8 Hz, 1H), 8.89-8.69 (m, 1H), 8.11 (d, J=1.0 Hz, 1H), 7.74-7.59 (m, 2H), 7.53 (dd, J=8.8, 4.4 Hz, 1H), 5.21 (s, 1H), 4.24-4.00 (m, 2H), 3.45-3.29 (m, 1H), 3.26 (d, J=12.1 Hz, 2H), 3.16 (d, J=12.2 Hz, 1H), 2.97 (d, J=16.1 Hz, 1H), 1.61 (ddt, J=12.9, 8.9, 4.6 Hz, 1H), 0.59 (dq, J=7.3, 5.3, 4.7 Hz, 4H), 0.53-0.34 (m, 1H). ES/MS 470.2 (M+H$^+$).

(S)-2,4-diamino-6-(((5-chloro-8-fluoro-4-oxo-3-(piperazin-1-yl)-3,4-dihydroquinazolin-2-yl)(cyclopropyl)methyl)amino)pyrimidine-5-carbonitrile (Compound 48). 1H NMR (400 MHz, DMSO-d$_6$) δ 9.49 (d, J=13.7 Hz, 1H), 8.87 (d, J=11.7 Hz, 1H), 8.34 (s, 3H), 8.01 (s, 1H), 7.81-7.64 (m, 1H), 7.58 (dt, J=8.4, 3.6 Hz, 1H), 5.23 (s, 1H), 4.09 (q, J=12.1, 11.7 Hz, 2H), 3.34 (dd, J=16.4, 11.6 Hz, 2H), 3.24 (d, J=12.0 Hz, 1H), 3.07 (d, J=12.0 Hz, 2H), 1.54 (s, 1H), 1.35-1.11 (m, 1H), 0.69-0.43 (m, 3H), 0.34 (s, 1H). ES/MS 485.2 (M+H$^+$).

(S)-5,8-dichloro-3-(piperazin-1-yl)-2-(1-(thiazolo[5,4-d]pyrimidin-7-ylamino)ethyl)quinazolin-4(3H)-one (Compound 49) H NMR (400 MHz, DMSO-d$_6$) δ 9.28 (s, 1H), 8.83-8.67 (m, 1H), 8.59 (dd, J=18.4, 8.6 Hz, 2H), 8.44 (s, 1H), 7.90 (d, J=8.5 Hz, 1H), 7.52 (d, J=8.5 Hz, 1H), 5.84 (p, J=6.7 Hz, 1H), 4.06 (dtd, J=19.4, 12.5, 2.7 Hz, 2H), 3.35-3.30 (m, 1H), 3.22 (d, J=12.2 Hz, 1H), 3.07 (q, J=12.0 Hz, 1H), 2.58 (t, J=11.9 Hz, 1H), 1.60 (d, J=6.7 Hz, 3H). ES/MS 477.1 (M+H$^+$).

(S)-5-chloro-8-fluoro-3-(piperazin-1-yl)-2-(1-(thiazolo[5,4-d]pyrimidin-7-ylamino)ethyl)quinazolin-4(3H)-one (Compound 50). 1H NMR (400 MHz, DMSO-d$_6$) δ 9.29 (d, J=1.0 Hz, 1H), 8.77 (d, J=11.6 Hz, 1H), 8.72 (d, J=6.9 Hz, 1H), 8.56 (d, J=11.1 Hz, 1H), 8.40 (s, 1H), 7.65 (t, J=9.2 Hz, 1H), 7.52 (dd, J=8.7, 4.3 Hz, 1H), 5.86 (p, J=6.7 Hz, 1H), 4.17-3.97 (m, 2H), 3.11 (d, J=12.5 Hz, 1H), 2.76 (q, J=11.8 Hz, 1H), 2.51 (d, J=0.9 Hz, 0H), 1.58 (d, J=6.8 Hz, 3H). ES/MS 461.1 (M+H$^+$).

(S)-5-chloro-2-(1-((6-chloropyrido[3,2-d]pyrimidin-4-yl)amino)ethyl)-8-fluoro-3-(piperazin-1-yl)quinazolin-4(3H)-one (Compound 51). (H NMR (400 MHz, DMSO-d$_6$) δ 9.18 (d, J=7.0 Hz, 1H), 8.91 (d, J=10.9 Hz, 1H), 8.65 (s, 2H), 8.23 (dd, J=8.8, 1.1 Hz, 1H), 7.98 (dd, J=8.7, 1.1 Hz, 1H), 7.72 (dd, J=9.7, 8.7 Hz, 1H), 7.58 (ddd, J=8.7, 4.4, 1.1 Hz, 1H), 5.89 (p, J=6.8 Hz, 1H), 4.26-3.99 (m, 2H), 3.53-3.27 (m, 4H), 3.20 (q, J=12.2, 11.0 Hz, 1H), 2.84 (t, J=12.3 Hz, 1H), 1.74-1.59 (m, 3H). ES/MS 489.1 (M+H$^+$).

(S)-5,8-dichloro-2-(1-((6-chloropyrido[3,2-d]pyrimidin-4-yl)amino)ethyl)-3-(piperazin-1-yl)quinazolin-4(3H)-one (Compound 52). 1H NMR (400 MHz, DMSO-d$_6$) δ 9.60

(d, J=7.3 Hz, 1H), 9.03 (d, J=11.0 Hz, 1H), 8.80 (d, J=1.9 Hz, 1H), 8.72 (q, J=11.4, 10.7 Hz, 1H), 8.29 (dd, J=8.8, 2.0 Hz, 1H), 8.04 (dd, J=8.8, 2.0 Hz, 1H), 7.99 (dd, J=8.7, 1.9 Hz, 1H), 7.59 (dd, J=8.5, 2.0 Hz, 1H), 5.82 (pd, J=6.7, 2.0 Hz, 1H), 4.24-4.11 (m, 1H), 4.11-3.97 (m, 1H), 3.51-3.27 (m, 2H), 3.27-3.09 (m, 1H), 2.88-2.68 (m, 1H), 2.08 (d, J=2.0 Hz, 1H), 1.69 (dd, J=6.7, 2.0 Hz, 3H). ES/MS 505.1 (M+H$^+$).

(S)-2,4-diamino-6-((1-(5,8-dichloro-4-oxo-3-(piperazin-1-yl)-3,4-dihydroquinazolin-2-yl)ethyl)amino)pyrimidine-5-carbonitrile (Compound 53). 1H NMR (400 MHz, DMSO-d$_6$) δ 9.05 (d, J=11.6 Hz, 1H), 8.81-8.58 (m, 1H), 7.98 (dt, J=8.6, 0.9 Hz, 1H), 7.92-7.63 (m, 5H), 7.58 (dt, J=8.5, 0.9 Hz, 1H), 5.66 (h, J=6.4 Hz, 1H), 4.09 (qd, J=11.3, 2.1 Hz, 2H), 3.43 (dd, J=18.0, 12.4 Hz, 2H), 3.37-3.28 (m, 1H), 3.28-3.16 (m, 1H), 3.03 (q, J=11.3 Hz, 1H), 2.85-2.61 (m, 1H), 1.51 (d, J=6.6 Hz, 3H). ES/MS 475.2 (M+H$^+$).

(S)-2,4-diamino-6-((1-(5-chloro-8-fluoro-4-oxo-3-(piperazin-1-yl)-3,4-dihydroquinazolin-2-yl)ethyl)amino)pyrimidine-5-carbonitrile (Compound 54). 1H NMR (400 MHz, DMSO-d$_6$) δ 9.11-8.92 (m, 1H), 8.67 (d, J=11.1 Hz, 1H), 7.72 (q, J=8.5, 7.8 Hz, 2H), 7.58 (dd, J=8.8, 4.4 Hz, 1H), 7.54-7.34 (m, 5H), 7.34-7.01 (m, 3H), 5.66 (p, J=6.8 Hz, 1H), 4.10 (tdd, J=12.3, 9.5, 2.7 Hz, 2H), 3.42 (dd, J=19.4, 12.2 Hz, 2H), 3.35-3.19 (m, 2H), 3.14-2.95 (m, 1H), 2.84-2.69 (m, 1H), 1.48 (d, J=6.7 Hz, 3H). ES/MS 459.2 (M+H$^+$).

(S)-4-amino-6-((1-(5-chloro-4-oxo-3-(piperazin-1-yl)-3,4-dihydroquinazolin-2-yl)ethyl)amino)pyrimidine-5-carbonitrile (Compound 55). 1H NMR (400 MHz, DMSO-d$_6$) δ 8.82 (d, J=10.9 Hz, 1H), 8.59 (d, J=11.5 Hz, 1H), 8.05 (s, 1H), 7.81 (d, J=6.9 Hz, 1H), 7.77-7.69 (m, 1H), 7.62-7.51 (m, 2H), 7.39 (s, 2H), 5.74 (p, J=6.7 Hz, 1H), 4.11 (dt, J=14.5, 11.3 Hz, 2H), 3.36 (dt, J=21.4, 11.4 Hz, 4H), 3.10 (t, J=12.1 Hz, 1H), 2.87-2.67 (m, 1H), 1.49 (d, J=6.7 Hz, 3H). ES/MS 426.2 (M+H$^+$).

(S)-3-amino-N-(1-(5-chloro-4-oxo-3-(piperazin-1-yl)-3,4-dihydroquinazolin-2-yl)ethyl)pyrazine-2-carboxamide (Compound 56). 1H NMR (400 MHz, DMSO-d$_6$) δ 9.08 (d, J=7.4 Hz, 1H), 8.23 (d, J=2.3 Hz, 1H), 7.86 (d, J=2.3 Hz, 1H), 7.75-7.63 (m, 5H), 7.58-7.49 (m, 4H), 5.59 (s, 1H), 4.26-4.00 (m, 2H), 3.43-3.31 (m, 2H), 3.31-3.14 (m, 2H), 3.14-2.93 (m, 1H), 2.93-2.61 (m, 1H), 1.49 (d, J=6.6 Hz, 3H), ES/MS 429.2 (M+H$^+$).

(S)-2,4-diamino-6-((1-(5-chloro-4-oxo-3-(piperazin-1-yl)-3,4-dihydroquinazolin-2-yl)ethyl)amino)pyrimidine-5-carbonitrile (Compound 57). 1H NMR (400 MHz, DMSO-d$_6$) δ 9.60 (s, 1H), 9.08 (d, J=11.5 Hz, 1H), 8.39 (d, J=38.4 Hz, 4H), 7.74 (dd, J=8.4, 7.6 Hz, 1H), 7.66-7.44 (m, 2H), 5.59 (s, 1H), 4.26-4.00 (m, 2H), 3.43-3.31 (m, 2H), 3.31-3.14 (m, 2H), 3.14-2.93 (m, 1H), 2.93-2.61 (m, 1H), 1.47 (d, J=6.7 Hz, 3H). ES/MS 441.2 (M+H$^+$).

(S)-2-(1-((6-amino-5-((5-fluoropyridin-2-yl)ethynyl)pyrimidin-4-yl)amino)ethyl)-5-chloro-3-(piperazin-1-yl)quinazolin-4(3H)-one (Compound 58). 1H NMR (400 MHz, DMSO-d$_6$) δ 8.84 (d, J=11.4 Hz, 1H), 8.61 (d, J=14.8 Hz, 1H), 8.14-8.06 (m, 0H), 7.93 (ddt, J=8.9, 4.5, 2.0 Hz, 1H), 7.88-7.72 (m, 1H), 7.61 (d, J=5.9 Hz, 1H), 7.55 (ddd, J=7.5, 3.8, 1.9 Hz, 1H), 7.28 (s, 1H), 5.68-5.46 (m, 1H), 4.17 (t, J=12.6 Hz, 1H), 4.04 (t, J=12.7 Hz, 1H), 3.46-3.34 (m, 1H), 3.30 (d, J=12.8 Hz, 1H), 3.14 (t, J=13.8 Hz, 1H), 2.97 (d, J=12.2 Hz, 1H), 1.58-1.33 (m, 2H). ES/MS 520.2 (M+H$^+$).

(S)-3-amino-N-(1-(5-chloro-4-oxo-3-(piperazin-1-yl)-3,4-dihydroquinazolin-2-yl)ethyl)-5,6-dimethylpyrazine-2-carboxamide (Compound 59). $^1$H NMR (400 MHz, DMSO-d$_6$) δ 9.43 (d, J=10.8 Hz, 1H), 8.98 (d, J=7.8 Hz, 1H), 8.91 (d, J=11.2 Hz, 1H), 7.77 (td, J=8.0, 0.9 Hz, 1H), 7.68-7.61 (m, 1H), 7.57 (dt, J=7.8, 1.0 Hz, 1H), 5.51 (h, J=6.6, 6.1 Hz, 1H), 4.29-4.04 (m, 3H), 3.62-3.52 (m, 1H), 3.31 (tt, J=33.8, 16.1 Hz, 4H), 3.07 (d, J=12.0 Hz, 1H), 2.75-2.63 (m, 2H), 2.46-2.29 (m, 4H), 1.62-1.44 (m, 2H). ES/MS 457.2 (M+H$^+$).

(S)-4-amino-6-((1-(5-methyl-4-oxo-3-(piperidin-4-yl)-3,4-dihydroquinazolin-2-yl)ethyl)amino)pyrimidine-5-carbonitrile (Compound 60). $^1$H NMR (400 MHz, DMSO-d$_6$) δ 8.11 (dd, J=27.0, 4.8 Hz, 2H), 7.71-7.55 (m, 1H), 7.44 (d, J=8.2 Hz, 3H), 7.30-7.14 (m, 1H), 6.45 (dd, J=7.5, 3.5 Hz, 1H), 5.74 (q, J=6.9 Hz, 1H), 4.02 (dd, J=52.3, 13.7 Hz, 3H), 3.12-2.93 (m, 2H), 2.74 (s, 3H), 2.67-2.53 (m, 2H), 2.07 (t, J=12.8 Hz, 1H), 1.52 (d, J=6.2 Hz, 4H). ES/MS 405.2 (M+H$^+$).

2,4-diamino-6-(((1S)-1-(5-chloro-4-oxo-3-(3-(trifluoromethyl)piperazin-1-yl)-3,4-dihydroquinazolin-2-yl)ethyl)amino)pyrimidine-5-carbonitrile (Compound 61). 1H NMR (400 MHz, DMSO-d6) δ 7.69 (t, J=8.0 Hz, 1H), 7.51 (dd, J=7.9, 1.2 Hz, 1H), 7.47 (dd, J=8.1, 1.1 Hz, 1H), 5.36 (p, J=6.8 Hz, 1H), 4.18-3.99 (m, 2H), 3.89 (br s, 1H), 3.68 (d, J=12.5 Hz, 1H), 3.19-2.98 (m, 3H), 1.44 (d, J=6.9 Hz, 3H). ES/MS 509.1 (M+H$^+$).

4-amino-6-(((1S)-1-(5-chloro-4-oxo-3-(3-(trifluoromethyl)piperazin-1-yl)-3,4-dihydroquinazolin-2-yl)ethyl)amino)pyrimidine-5-carbonitrile (Compound 62). 1H NMR (400 MHz, DMSO-d6) δ 1H NMR (400 MHz, DMSO-d6) δ 7.89 (s, 1H), 7.72-7.65 (m, 2H), 7.50 (dd, J=7.9, 1.1 Hz, 1H), 7.47 (dd, J=8.1, 1.2 Hz, 1H), 7.34 (br s, 2H), 5.58 (p, J=6.8 Hz, 1H), 4.20 (d, J=12.6 Hz, 1H), 4.09 (t, J=11.5 Hz, 2H), 3.70 (d, J=12.2 Hz, 1H), 3.24-3.05 (m, 3H), 1.44 (d, J=6.8 Hz, 3H). ES/MS 494.1 (M+H$^+$).

(S)-4-amino-6-((1-(5-chloro-4-oxo-3-(4,7-diazaspiro[2.5]octan-7-yl)-3,4-dihydroquinazolin-2-yl)ethyl)amino)pyrimidine-5-carbonitrile (Compound 63). 1H NMR (400 MHz, DMSO-d6) δ 9.42 (d, J=11.6 Hz, 2H), 8.76 (s, 1H), 7.93 (s, 1H), 7.70 (t, J=8.0 Hz, 1H), 7.64 (d, J=7.1 Hz, 1H), 7.53-7.49 (m, 2H), 7.34 (s, 2H), 5.84 (p, J=7.1 Hz, 1H), 4.47 (d, J=11.8 Hz, 1H), 4.23 (t, J=12.2 Hz, 1H), 3.32-3.21 (m, 1H), 2.86 (d, J=11.9 Hz, 1H), 1.49 (d, J=6.9 Hz, 3H), 0.99 (dt, J=25.1, 6.4 Hz, 4H). ES/MS 452.1 (M+H$^+$).

(S)-5-chloro-3-(1,4-diazepan-1-yl)-2-(1-(imidazo[2,1-f][1,2,4]triazin-4-ylamino)ethyl)quinazolin-4(3H)-one (Compound 64). Exists as a ~1:1 mixture of rotamers. 1H NMR (400 MHz, DMSO-d6) δ 9.34 (d, J=6.3 Hz, 0.5H), 9.28 (d, J=6.7 Hz, 0.5H), 8.73 (s, 2H), 8.12-8.08 (m, 2H), 7.69 (td, J=8.0, 3.3 Hz, 1H), 7.65 (t, J=1.2 Hz, 1H), 7.55-7.48 (m, 2H), 6.01 (p, J=6.9 Hz, 0.5H), 5.92 (p, J=6.8 Hz, 0.5H), 4.11-3.98 (m, 1H), 3.86 (dt, J=12.1, 6.0 Hz, 0.5H), 3.81-3.71 (m, 0.5H), 3.63-3.15 (m, 5H), 2.10-1.89 (m, 2H), 1.62 (dd, J=6.8, 3.4 Hz, 3H). ES/MS 440.1 (M+H$^+$).

(S)-5-chloro-2-(1-(imidazo[2,1-f][1,2,4]triazin-4-ylamino)ethyl)-3-(piperazin-1-yl)quinazolin-4(3H)-one (Compound 65). 1H NMR (400 MHz, DMSO-d6) δ 9.26 (d, J=6.7 Hz, 1H), 8.94-8.84 (m, 1H), 8.71-8.56 (m, 1H), 8.14-8.09 (m, 2H), 7.72 (dd, J=8.3, 7.8 Hz, 1H), 7.64 (d, J=1.1 Hz, 1H), 7.57-7.51 (m, 2H), 5.84 (p, J=6.8 Hz, 1H), 4.14 (dtd, J=21.1, 12.1, 2.8 Hz, 2H), 3.49-3.38 (m, 2H), 3.33 (d, J=12.2 Hz, 2H), 3.17 (q, J=12.1 Hz, 1H), 2.90 (q, J=11.9 Hz, 1H), 1.62 (d, J=6.8 Hz, 3H). ES/MS 426.1 (M+H$^+$).

(S)-5-chloro-2-(1-((2,6-diamino-5-chloropyrimidin-4-yl)amino)ethyl)-3-(piperazin-1-yl)quinazolin-4(3H)-one (Compound 72). 1H NMR (400 MHz, DMSO-d6) δ 8.97-8.86 (m, 1H), 8.69-8.54 (m, 1H), 7.76 (dd, J=8.3, 7.8

Hz, 1H), 7.62-7.54 (m, 2H), 5.57 (p, J=6.8 Hz, 1H), 4.21-4.04 (m, 2H), 3.51-3.34 (m, 2H), 3.35-3.21 (m, 2H), 3.03 (q, J=12.1 Hz, 1H), 2.79 (q, J=12.2 Hz, 1H), 1.50 (d, J=6.7 Hz, 3H). ES/MS 450.1 (M+H$^+$).

(S)-4-amino-6-((1-(5-chloro-3-(1,4-diazepan-1-yl)-4-oxo-3,4-dihydroquinazolin-2-yl)ethyl)amino)pyrimidine-5-carbonitrile (Compound 66). 1H NMR (400 MHz, DMSO-d6) δ 8.69-8.58 (m, 2H), 8.00 (s, 1H), 7.78 (d, J=6.6 Hz, 1H), 7.72 (dd, J=8.3, 7.8 Hz, 1H), 7.57-7.50 (m, 2H), 7.35 (s, 2H), 5.86 (p, J=6.8 Hz, 1H), 4.04-3.93 (m, 1H), 3.87-3.78 (m, 1H), 3.62-3.15 (m, 6H), 2.03 (s, 2H), 1.50 (d, J=6.8 Hz, 3H). ES/MS 440.1 (M+H$^+$).

(S)-4-amino-6-((1-(5-chloro-3-(1,4-diazepan-1-yl)-4-oxo-3,4-dihydroquinazolin-2-yl)ethyl)amino)pyrimidine-5-carbonitrile (Compound 67). 1H NMR (400 MHz, DMSO-d6) δ 8.69-8.59 (m, 2H), 8.16-8.09 (m, 1H), 8.00 (s, 1H), 7.77 (d, J=6.9 Hz, 1H), 7.73 (dd, J=8.2, 7.8 Hz, 1H), 7.55 (td, J=8.1, 1.2 Hz, 2H), 7.35 (s, 2H), 5.81 (p, J=6.7 Hz, 1H), 4.04 (dd, J=14.8, 10.2 Hz, 1H), 3.78-3.67 (m, 1H), 3.53-3.09 (m, 6H), 1.94 (d, J=25.3 Hz, 2H), 1.51 (d, J=6.8 Hz, 3H). ES/MS 440.1 (M+H$^+$).

(S)-2,4-diamino-6-((1-(5-chloro-4-oxo-3-(piperazin-1-yl)-3,4-dihydroquinazolin-2-yl)propyl)amino)pyrimidine-5-carbonitrile (Compound 68). $^1$H NMR (400 MHz, DMSO-d$_6$) δ 9.00-8.88 (m, 1H), 8.76-8.60 (m, 1H), 7.97 (br s, 2H), 7.76 (dd, J=8.3, 7.7 Hz, 1H), 7.61-7.54 (m, 2H), 5.51-5.42 (m, 1H), 4.24-4.04 (m, 2H), 3.53-3.37 (m, 2H), 3.35-3.21 (m, 2H), 3.12-2.84 (m, 2H), 1.99-1.84 (m, 2H), 1.01 (t, J=7.3 Hz, 3H). ES/MS 455.2 (M+H$^+$).

(S)-2-(1-((5-bromo-7H-pyrrolo[2,3-d]pyrimidin-4-yl)amino)ethyl)-5-chloro-3-(piperazin-1-yl)quinazolin-4(3H)-one (Compound 69). $^1$H NMR (400 MHz, DMSO-d$_6$) δ 8.21 (s, 1H), 7.76 (t, J=8.0 Hz, 1H), 7.68 (dd, J=8.2, 1.3 Hz, 1H), 7.57 (dd, J=7.7, 1.2 Hz, 1H), 7.44 (d, J=2.6 Hz, 1H), 5.85-5.78 (m, 1H), 4.31-4.19 (m, 1H), 4.14-4.02 (m, 1H), 3.53-3.05 (m, 4H), 1.59 (d, J=6.5 Hz, 3H). ES/MS 505.1 (M+H$^+$).

(S)-5-chloro-3-(piperazin-1-yl)-2-(1-(thiazolo[5,4-d]pyrimidin-7-ylamino)ethyl)quinazolin-4(3H)-one (Compound 70). $^1$H NMR (400 MHz, DMSO-d$_6$) δ 9.32 (s, 1H), 8.72 (d, J=7.0 Hz, 2H), 8.64-8.51 (m, 1H), 8.43 (s, 1H), 7.72 (t, J=8.2 Hz, 1H), 7.59-7.49 (m, 2H), 5.88 (t, J=6.8 Hz, 1H), 4.24-4.06 (m, 2H), 3.51-3.05 (m, 5H), 2.81 (s, 1H), 1.61 (d, J=6.8 Hz, 3H). ES/MS 443.1 (M+H$^+$).

(S)-5-chloro-2-(1-((6-chloropyrido[3,2-d]pyrimidin-4-yl)amino)ethyl)-3-(piperazin-1-yl)quinazolin-4(3H)-one (Compound 71). $^1$H NMR (400 MHz, DMSO-d$_6$) δ 9.00 (d, J=7.4 Hz, 1H), 8.87-8.78 (m, 1H), 8.60 (s, 1H), 8.67-8.63 (m, 0H), 8.59-8.53 (m, 1H), 8.21 (d, J=8.8 Hz, 1H), 7.96 (d, J=8.8 Hz, 1H), 7.74 (dd, J=8.3, 7.8 Hz, 1H), 7.58 (dd, J=8.3, 1.2 Hz, 1H), 7.56 (dd, J=7.7, 1.2 Hz, 1H), 5.89 (p, J=6.7 Hz, 1H), 4.22-4.06 (m, 2H), 3.50-3.12 (m, 5H), 2.89-2.75 (m, 1H), 1.65 (d, J=6.8 Hz, 3H). ES/MS 471.1 (M+H$^+$).

(S)-5-chloro-3-(piperazin-1-yl)-2-(1-(pyrido[3,2-d]pyrimidin-4-ylamino)ethyl)quinazolin-4(3H)-one (Compound 73). $^1$H NMR (400 MHz, DMSO-d$_6$) δ 8.96-8.88 (m, 1H), 8.85-8.75 (m, 1H), 8.68-8.52 (m, 2H), 8.18 (d, J=8.4 Hz, 1H), 7.98-7.90 (m, 1H), 7.74 (dd, J=8.3, 7.7 Hz, 1H), 7.57 (dd, J=8.3, 1.2 Hz, 1H), 7.56 (dd, J=7.7, 1.2 Hz, 1H), 5.92 (p, J=7.1 Hz, 1H), 4.24-4.06 (m, 2H), 3.50-3.12 (m, 5H), 2.96-2.81 (m, 1H), 1.66 (d, J=6.8 Hz, 3H). ES/MS 437.1 (M+H$^+$).

(S)-4-amino-6-((1-(5-chloro-4-oxo-3-(piperazin-1-yl)-3,4-dihydroquinazolin-2-yl)-3-methylbutyl)amino)pyrimidine-5-carbonitrile (Compound 74). $^1$H NMR (400 MHz, DMSO-d$_6$) δ 8.89-8.64 (m, 2H), 7.99 (s, 1H), 7.72 (t, J=7.9 Hz, 1H), 7.71-7.67 (m, 1H), 7.54 (dd, J=8.0, 1.1 Hz, 1H), 7.53 (dd, J=8.0, 1.1 Hz, 1H), 7.39 (br s, 2H), 5.86 (ddd, J=11.1, 7.7, 3.5 Hz, 1H), 4.32-4.18 (m, 1H), 4.18-4.03 (m, 1H), 3.59-3.39 (m, 3H), 3.38-3.24 (m, 1H), 3.15-2.88 (m, 2H), 1.94 (ddd, J=14.0, 10.7, 4.1 Hz, 1H), 1.89-1.77 (m, 1H), 1.52 (ddd, J=13.2, 9.4, 3.6 Hz, 1H), 0.99 (d, J=6.4 Hz, 3H), 0.95 (d, J=6.5 Hz, 3H). ES/MS 483.2 (M+H$^+$).

(S)-2,4-diamino-6-((1-(5-chloro-4-oxo-3-(piperazin-1-yl)-3,4-dihydroquinazolin-2-yl)-3-methylbutyl)amino)pyrimidine-5-carbonitrile (Compound 75). $^1$H NMR (400 MHz, DMSO-d$_6$) δ 8.88-8.76 (m, 1H), 8.77-8.61 (m, 1H), 7.74 (t, J=8.0 Hz, 1H), 7.56 (dd, J=8.0, 1.1 Hz, 1H), 7.55 (dd, J=8.1, 1.1 Hz, 1H), 7.34 (s, 2H), 6.99 (s, 2H), 5.75-5.62 (m, 1H), 4.25 (td, J=12.5, 2.8 Hz, 1H), 4.11 (td, J=12.2, 2.0 Hz, 1H), 3.56-3.40 (m, 2H), 3.40-3.21 (m, 2H), 3.15-2.86 (m, 2H), 1.90-1.72 (m, 2H), 1.63-1.51 (m, 1H), 1.01 (d, J=6.4 Hz, 3H), 0.95 (d, J=6.5 Hz, 3H). ES/MS 468.2 (M+H$^+$).

(S)-4-amino-6-((1-(5,8-dichloro-4-oxo-3-(piperazin-1-yl)-3,4-dihydroquinazolin-2-yl)ethyl)amino)pyrimidine-5-carbonitrile (Compound 76). $^1$H NMR (400 MHz, DMSO-d$_6$) δ 8.82-8.73 (m, 1H), 8.65-8.51 (m, 1H), 8.10 (s, 1H), 7.97 (d, J=8.5 Hz, 1H), 7.69 (d, J=7.1 Hz, 1H), 7.57 (d, J=8.5 Hz, 1H), 7.41 (br s, 2H), 5.72 (p, J=6.9 Hz, 1H), 4.17-3.98 (m, 2H), 3.49-3.21 (m, 4H), 3.16-2.98 (m, 1H), 2.76-2.63 (m, 1H), 1.52 (d, J=6.7 Hz, 3H). ES/MS 460.1 (M+H$^+$).

(S)-4-amino-6-(((5-chloro-4-oxo-3-(piperazin-1-yl)-3,4-dihydroquinazolin-2-yl)(cyclopropyl)methyl)amino)pyrimidine-5-carbonitrile (Compound 102). $^1$H NMR (400 MHz, DMSO-d$_6$) δ 8.87-8.74 (m, 1H), 8.66-8.49 (m, 1H), 8.04 (s, 1H), 7.76 (t, J=8.1 Hz, 1H), 7.61 (dd, J=8.2, 1.2 Hz, 2H), 7.57 (dd, J=7.8, 1.2 Hz, 1H), 7.43 (br s, 2H), 5.32-5.21 (m, 1H), 4.24-4.04 (m, 2H), 3.46-3.06 (m, 5H), 2.83-2.65 (m, 1H), 1.60-1.49 (m, 1H), 0.63-0.50 (m, 3H), 0.46-0.35 (m, 1H). ES/MS 452.1 (M+H$^+$).

(S)-2,4-diamino-6-(((5-chloro-4-oxo-3-(piperazin-1-yl)-3,4-dihydroquinazolin-2-yl)(cyclopropyl)methyl)amino)pyrimidine-5-carbonitrile (Compound 77). $^1$H NMR (400 MHz, DMSO-d$_6$) δ 9.05-8.90 (m, 1H), 8.71-8.52 (m, 1H), 7.78 (t, J=8.0 Hz, 1H), 7.64 (dd, J=8.2, 1.2 Hz, 1H), 7.61 (br s, 2H), 7.59 (dd, J=7.8, 1.2 Hz, 1H), 5.36-5.20 (m, 1H), 4.25-4.06 (m, 2H), 3.51-3.03 (m, 5H), 2.78-2.60 (m, 1H), 1.63-1.46 (m, 1H), 0.71-0.48 (m, 3H), 0.42-0.30 (m, 1H). ES/MS 467.2 (M+H$^+$).

(S)-5-chloro-2-(cyclopropyl(thiazolo[5,4-d]pyrimidin-7-ylamino)methyl)-3-(piperazin-1-yl)quinazolin-4(3H)-one (Compound 78). $^1$H NMR (400 MHz, DMSO-d$_6$) δ 9.32 (s, 1H), 8.85-8.75 (m, 1H), 8.66-8.49 (m, 2H), 8.42 (s, 1H), 7.75 (dd, J=8.2, 7.8 Hz, 1H), 7.61 (dd, J=8.2, 1.2 Hz, 1H), 7.56 (dd, J=7.8, 1.2 Hz, 1H), 5.36 (s, 1H), 4.27-4.05 (m, 2H), 3.46-3.34 (m, 2H), 3.33-3.18 (m, 3H), 2.81 (s, 1H), 1.68-1.58 (m, 1H), 0.67-0.57 (m, 3H), 0.51-0.45 (m, 1H). ES/MS 469.1 (M+H$^+$).

(S)-4-amino-6-((1-(5-chloro-4-oxo-3-(piperazin-1-yl)-3,4-dihydroquinazolin-2-yl)propyl)amino)pyrimidine-5-carbonitrile (Compound 79). $^1$H NMR (400 MHz, DMSO-d$_6$) δ 8.85-8.74 (m, 1H), 8.68-8.54 (m, 1H), 8.00 (s, 1H), 7.71 (dd, J=8.3, 7.7 Hz, 1H), 7.66 (d, J=7.5 Hz, 1H), 7.53 (dd, J=8.3, 1.2 Hz, 1H), 7.52 (dd, J=7.7, 1.2 Hz, 1H), 7.40 (br s, 2H), 5.61 (td, J=7.5, 5.7 Hz, 1H), 4.14 (td, J=12.4, 2.7 Hz, 1H), 4.06 (td, J=12.5, 3.1 Hz, 1H), 3.45-3.31 (m, 3H), 3.29-3.20 (m, 1H), 3.14-2.81 (m, 2H), 1.94-1.84 (m, 2H), 0.97 (t, J=7.3 Hz, 3H). ES/MS 440.1 (M+H$^+$).

(S)-5-chloro-3-(piperazin-1-yl)-2-(1-(thiazolo[5,4-d]pyrimidin-7-ylamino)propyl)quinazolin-4(3H)-one (Compound 80). ¹H NMR (400 MHz, DMSO-d₆) δ 9.33 (s, 1H), 8.88-8.77 (m, 1H), 8.72-8.54 (m, 2H), 8.41 (s, 1H), 7.70 (t, J=8.0 Hz, 1H), 7.54 (dd, J=7.9, 1.2 Hz, 1H), 7.52 (dd, J=8.1, 1.1 Hz, 1H), 5.78 (td, J=7.6, 5.5 Hz, 1H), 4.22 (td, J=12.5, 2.3 Hz, 1H), 4.13 (td, J=12.6, 2.4 Hz, 1H), 3.56-3.35 (m, 3H), 3.35-3.25 (m, 1H), 3.25-2.94 (m, 2H), 2.11-1.96 (m, 2H), 1.08 (t, J=7.3 Hz, 3H). ES/MS 457.1 (M+H⁺).

3-(azepan-4-yl)-5-chloro-2-((S)-1-(pyrido[3,2-d]pyrimidin-4-ylamino)ethyl)quinazolin-4(3H)-one (Compound 81). ¹H NMR (400 MHz, DMSO-d₆) δ 8.94-8.89 (m, 1H), 8.66 (s, 1H), 8.46 (br s, 2H), 8.22-8.16 (m, 1H), 7.95-7.89 (m, 1H), 7.76-7.70 (m, 1H), 7.60-7.56 (m, 1H), 7.56-7.52 (m, 1H), 5.89-5.74 (m, 1H), 4.59-4.43 (m, 1H), 3.31-2.88 (m, 6H), 2.28-1.54 (m, 7H). ES/MS 450.2 (M+H⁺).

3-(azepan-4-yl)-5-chloro-2-((S)-1-(imidazo[2,1-f][1,2,4]triazin-4-ylamino)ethyl)quinazolin-4(3H)-one (Compound 82). ¹H NMR (400 MHz, DMSO-d₆) δ 9.41-9.32 (m, 1H), 8.58-8.36 (m, 2H), 8.21-8.17 (m, 1H), 8.15-8.11 (m, 1H), 7.75-7.68 (m, 1H), 7.67-7.64 (m, 1H), 7.58-7.52 (m, 2H), 5.80-5.68 (m, 1H), 4.55-4.38 (m, 1H), 3.10 (d, J=35.4 Hz, 6H), 2.24-1.88 (m, 3H), 1.78-1.55 (m, 4H). ES/MS 439.2 (M+H⁺).

4-amino-6-(((1S)-1-(5-chloro-4-oxo-3-(piperidin-3-yl)-3,4-dihydroquinazolin-2-yl)ethyl)amino)pyrimidine-5-carbonitrile (Compound 83). 1H NMR (400 MHz, DMSO-d₆) δ 8.82 (s, 1H), 8.44 (s, 1H), 8.06 (s, 1H), 7.82 (d, J=7.1 Hz, 1H), 7.74-7.69 (m, 1H), 7.53 (d, J=7.9 Hz, 2H), 7.37 (s, 2H), 5.52 (m, 1H), 4.35 (m, 1H), 3.98 (m, 1H), 3.41 (m, 1H), 3.25 (m, 1H), 2.84 (m, 1H), 2.63 (m, 1H), 1.89 (m, 2H), 1.52 (d, J=6.5 Hz, 3H), 1.38 (m, 1H). ES/MS 425.0 (M+H⁺).

4-amino-6-(((1S)-1-(3-(azepan-4-yl)-5-chloro-4-oxo-3,4-dihydroquinazolin-2-yl)ethyl)amino)pyrimidine-5-carbonitrile (Compound 84). 1H NMR (400 MHz, DMSO-d₆) δ 8.49 (s, 1H), 8.09 (s, 1H), 7.99-7.88 (m, 1H), 7.72 (td, J=8.0, 8.0, 1.0 Hz, 1H), 7.58-7.50 (m, 2H), 7.42 (m, 1H), 5.65 (m, 1H), 4.32 (m, 1H), 3.40 (m, 1H), 3.05 (m, 3H), 2.68-2.58 (m, 1H), 2.17-1.83 (m, 1H), 1.65 (m, 1H), 1.50 (d, J=6.4 Hz, 3H), 1.38 (m, 1H). ES/MS 438.9 (M+H⁺).

4-amino-6-(((1S)-1-(5-chloro-4-oxo-3-(pyrrolidin-3-yl)-3,4-dihydroquinazolin-2-yl)ethyl)amino)pyrimidine-5-carbonitrile (Compound 85). 1H NMR (400 MHz, DMSO-d₆) δ 8.90 (s, 1H), 8.57 (s, 1H), 8.08 (s, 1H), 7.81 (d, J=7.4 Hz, 1H), 7.75 (t, J=8.0, 8.0 Hz, 1H), 7.57 (m, 2H), 7.38 (s, 2H), 5.67 (m, 1H), 5.04 (m, 1H), 3.62 (m, 2H), 3.38 (m, 1H), 3.12 (m, 1H), 2.28 (m, 2H), 2.11 (m, 1H), 1.50 (d, J=6.5 Hz, 3H). ES/MS 411.1 (M+H⁺).

(S)-4-amino-6-((1-(5-chloro-4-oxo-3-(piperidin-4-yl)-3,4-dihydroquinazolin-2-yl)ethyl)amino)pyrimidine-5-carbonitrile (Compound 86). 1H NMR (400 MHz, DMSO-d₆) δ 8.46 (s, 1H), 8.38 (s, 1H), 8.08 (s, 1H), 7.92 (d, J=7.1 Hz, 1H), 7.71 (t, J=8.0, 8.0 Hz, 1H), 7.53 (td, J=7.8, 7.7, 1.2 Hz, 2H), 7.40 (s, 2H), 5.66 (m, 1H), 4.28 (m, 1H), 3.44-3.30 (m, 2H), 2.92 (m, 4H), 1.87 (m, 2H), 1.50 (d, J=6.5 Hz, 3H). ES/MS 425.0 (M+H⁺).

(S)-2,4-diamino-6-((1-(8-chloro-6-fluoro-4-oxo-3-(piperazin-1-yl)-3,4-dihydroquinazolin-2-yl)ethyl)amino)pyrimidine-5-carbonitrile (Compound 126). ¹H NMR (400 MHz, DMSO-d₆) δ 9.64 (s, 1H), 9.02 (d, J=11.2 Hz, 1H), 8.34 (s, 3H), 8.23 (s, 2H), 8.14 (dd, J=8.4, 2.9 Hz, 1H), 7.86 (dd, J=8.2, 2.9 Hz, 1H), 5.68 (s, 1H), 4.22-3.99 (m, 2H), 3.47-3.29 (m, 2H), 3.29-3.14 (m, 1H), 3.15-2.86 (m, 1H), 2.79-2.67 (m, 1H), 1.54 (d, J=6.6 Hz, 3H). ES/MS 459.2 (M+H⁺).

(S)-2,4-diamino-6-((cyclopropyl(5,8-difluoro-4-oxo-3-(piperazin-1-yl)-3,4-dihydroquinazolin-2-yl)methyl)amino)pyrimidine-5-carbonitrile (Compound 127). ¹H NMR (400 MHz, DMSO-d₆) δ 9.44 (s, 1H), 8.84 (d, J=11.7 Hz, 1H), 8.16 (s, 2H), 7.88 (s, 2H), 7.76 (td, J=9.2, 4.0 Hz, 1H), 7.33 (ddt, J=10.4, 9.1, 2.0 Hz, 1H), 5.26 (s, 1H), 4.07 (p, J=10.4, 8.7 Hz, 2H), 3.65-3.17 (m, 4H), 3.09 (s, 1H), 1.53 (s, 1H), 0.75-0.41 (m, 3H), 0.41-0.16 (m, 1H). ES/MS 469.2 (M+H⁺).

(S)-2-Amino-4-chloro-6-((1-(5-chloro-4-oxo-3-(piperidin-4-yl)-3,4-dihydroquinazolin-2-yl)ethyl)amino)pyrimidine-5-carbonitrile (Compound 128). ¹H NMR (400 MHz, DMSO-d₆) δ 9.32 (d, J=10.9 Hz, 1H), 8.65 (d, J=11.8 Hz, 1H), 8.23 (d, J=7.7 Hz, 1H), 7.84 (s, 1H), 7.75 (dd, J=8.2, 7.8 Hz, 1H), 7.58 (m, 3H), 5.65 (m, 1H), 4.24 (m, 1H), 3.40 (m, 2H), 3.19-2.97 (m, 2H), 2.88 (m, 1H), 2.49 (m, 1H), 1.88 (m, 2H), 1.55 (d, J=6.4 Hz, 3H). ES/MS 459.1 (M+H⁺).

(S)-2,4-diamino-6-((1-(3-(4-aminopiperidin-1-yl)-5-chloro-4-oxo-3,4-dihydroquinazolin-2-yl)ethyl)amino)pyrimidine-5-carbonitrile (Compound 129). ¹H NMR (400 MHz, DMSO-d6) δ 7.90 (s, 4H), 7.72 (t, J=8.0 Hz, 1H), 7.57-7.49 (m, 2H), 5.55 (p, J=7.2 Hz, 1H), 3.92 (t, J=11.7 Hz, 1H), 3.79 (t, J=11.5 Hz, 1H), 3.33 (d, J=10.9 Hz, 1H), 3.23-3.07 (m, 3H), 2.02 (d, J=11.8 Hz, 2H), 1.77-1.60 (m, 2H), 1.50 (d, J=6.9 Hz, 3H). ES/MS 455.1 (M+H⁺).

4-amino-6-(((1S)-1-(3-(3-aminopyrrolidin-1-yl)-5-chloro-4-oxo-3,4-dihydroquinazolin-2-yl)ethyl)amino)pyrimidine-5-carbonitrile (Compound 130). ¹H NMR (400 MHz, DMSO-d6) δ 8.08 (s, 1H), 8.05-7.97 (m, 3H), 7.80-7.51 (m, 3H), 7.37 (s, 2H), 5.82-5.68 (m, 1H), 4.16-4.03 (m, 1H), 3.86 (dd, J=10.5, 7.4 Hz, 0.5H), 3.81-3.64 (m, 1H), 3.64-3.53 (m, 0.5H), 3.53-3.42 (m, 1H), 3.42-3.13 (m, 1H), 2.48-2.39 (m, 1H), 2.23-1.81 (m, 1H), 1.55-1.47 (m, 3H). ES/MS 426.1 (M+H⁺).

(S)-4-amino-6-((1-(3-(4-aminopiperidin-1-yl)-5-chloro-4-oxo-3,4-dihydroquinazolin-2-yl)ethyl)amino)pyrimidine-5-carbonitrile (Compound 131). ¹H NMR (400 MHz, DMSO-d6) δ 7.99 (s, 1H), 7.83 (s, 3H), 7.70 (t, J=8.0 Hz, 1H), 7.61 (d, J=6.9 Hz, 1H), 7.50 (dq, J=8.0, 1.2 Hz, 2H), 7.38-7.29 (m, 2H), 5.63 (p, J=6.7 Hz, 1H), 3.88 (t, J=11.8 Hz, 1H), 3.76 (t, J=11.4 Hz, 1H), 3.28 (d, J=10.9 Hz, 1H), 3.11 (d, J=11.4 Hz, 2H), 2.04-1.89 (m, 2H), 1.76-1.50 (m, 2H), 1.47 (d, J=6.7 Hz, 3H). ES/MS 440.2 (M+H⁺).

Example 5. Preparation of a Compound of Formula (4)

A. Preparation of a compound of formula (4) wherein n is 1, R¹ is chloro, m is 0, B is piperazinyl, PG is Fmoc, R⁵ is hydrogen, and R³ is ethyl

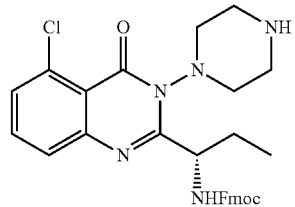

To a solution of (S)-tert-butyl 4-(2-(1-((((9H-fluoren-9-yl)methoxy)carbonyl)amino)propyl)-5-chloro-4-oxoquinazolin-3(4H)-yl)piperazine-1-carboxylate (3.10 g, 4.81 mmol) in dichloromethane (4 mL) was added trifluoroacetic acid (12 mL). The reaction solution stirred for 2 hours and was concentrated to give (S)-(9H-fluoren-9-yl)methyl (1-(5- chloro-4-oxo-3-(piperazin-1-yl)-3,4-dihydroquinazolin-2-yl)propyl)carbamate as a solid. The title compound was carried on to the next reaction without further purification. ES/MS m/z=544.3 (M+H⁺).

B. Preparation of the below compounds of Formula (4), using the procedures described in Example 5A and Reaction Scheme I:

(S)-(9H-fluoren-9-yl)methyl (1-(5-chloro-4-oxo-3-(piperazin-1-yl)-3,4-dihydroquinazolin-2-yl)ethyl)carbamate;

(S)-(9H-fluoren-9-yl)methyl ((5-chloro-4-oxo-3-(piperazin-1-yl)-3,4-dihydroquinazolin-2-yl)(cyclopropyl)methyl)carbamate;

(S)-(9H-fluoren-9-yl)methyl (1-(5-chloro-8-fluoro-4-oxo-3-(piperazin-1-yl)-3,4-dihydroquinazolin-2-yl)propyl)carbamate;

(S)-(9H-fluoren-9-yl)methyl (1-(5-chloro-4-oxo-3-(piperidin-4-yl)-3,4-dihydroquinazolin-2-yl)ethyl)carbamate;

(S)-(9H-fluoren-9-yl)methyl (1-(5-chloro-8-fluoro-4-oxo-3-(piperazin-1-yl)-3,4-dihydroquinazolin-2-yl)ethyl)carbamate; and (9H-fluoren-9-yl)methyl ((1S)-1-(5-chloro-4-oxo-3-(pyrrolidin-3-yl)-3,4-dihydroquinazolin-2-yl)ethyl)carbamate.

Example 6. Preparation of a Compound of Formula (5)

A. Preparation of a compound of formula (5) wherein n is 1, $R^1$ is chloro, m is 0, B is 4-(4-trifluoromethylphenylmethyl)piperazinyl, $R^3$ is ethyl, PG is Fmoc, $R^5$ is hydrogen

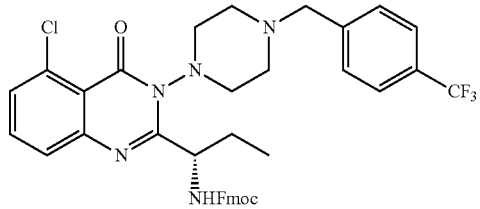

To a mixture of (S)-(9H-fluoren-9-yl)methyl (1-(5-chloro-4-oxo-3-(piperazin-1-yl)-3,4-dihydroquinazolin-2-yl)propyl)carbamate (253 mg, 0.465 mmol) and potassium carbonate (383 mg, 2.77 mmol) in acetonitrile (8 mL) was added 1-(bromomethyl)-4-(trifluoromethyl)benzene (127 mg, 0.530 mmol). The mixture stirred at 55° C. overnight. The mixture was concentrated and the residue was partitioned between EtOAc and water. The aqueous layer was extracted 2× with EtOAc; the combined organic layers were washed with brine, dried over sodium sulfate, filtered, and concentrated to give (S)-(9H-fluoren-9-yl)methyl (1-(5-chloro-4-oxo-3-(4-(4-(trifluoromethyl)benzyl)piperazin-1-yl)-3,4-dihydroquinazolin-2-yl)propyl)carbamate which was carried on to the next reaction without further purification. ES/MS 702.3 (M+H⁺).

To a solution of (S)-tert-butyl 4-(2-(1-((((9H-fluoren-9-yl)methoxy)carbonyl)amino)propyl)-5-chloro-4-oxoquinazolin-3(4H)-yl)piperazine-1-carboxylate (3.10 g, 4.81 mmol) in dichloromethane (4 mL) was added trifluoroacetic acid (12 mL). The reaction solution stirred for 2 hours and was concentrated to give (S)-(9H-fluoren-9-yl)methyl (1-(5-chloro-4-oxo-3-(piperazin-1-yl)-3,4-dihydroquinazolin-2-yl)propyl)carbamate as a solid. The title compound was carried on to the next reaction without further purification. ES/MS m/z=544.3 (M+H⁺).

B. Preparation of the below compounds of Formula (5), using the procedures described in Example 6A and Reaction Scheme I (S)-(9H-fluoren-9-yl)methyl (1-(5-chloro-3-(4-(4-fluorobenzyl)piperazin-1-yl)-4-oxo-3,4-dihydroquinazolin-2-yl)propyl)carbamate;

(S)-(9H-fluoren-9-yl)methyl (1-(5-chloro-3-(4-(4-methoxybenzyl)piperazin-1-yl)-4-oxo-3,4-dihydroquinazolin-2-yl)propyl)carbamate;

(S)-(9H-fluoren-9-yl)methyl (1-(5-chloro-3-(1-(2,2-difluoroethyl)piperidin-4-yl)-4-oxo-3,4-dihydroquinazolin-2-yl)ethyl)carbamate;

(S)-(9H-fluoren-9-yl)methyl (1-(5-chloro-4-oxo-3-(1-(2,2,2-trifluoroethyl)piperidin-4-yl)-3,4-dihydroquinazolin-2-yl)ethyl)carbamate;

(S)-(9H-fluoren-9-yl)methyl (1-(3-(1-benzylpiperidin-4-yl)-5-chloro-4-oxo-3,4-dihydroquinazolin-2-yl)ethyl)carbamate;

(S)-(9H-fluoren-9-yl)methyl (1-(5-chloro-4-oxo-3-(4-(2,2,2-trifluoroethyl)piperazin-1-yl)-3,4-dihydroquinazolin-2-yl)ethyl)carbamate;

(S)-(9H-fluoren-9-yl)methyl (1-(5-chloro-3-(4-(2,2-difluoroethyl)piperazin-1-yl)-4-oxo-3,4-dihydroquinazolin-2-yl)ethyl)carbamate;

(S)-(9H-fluoren-9-yl)methyl (1-(3-(4-benzylpiperazin-1-yl)-5-chloro-8-fluoro-4-oxo-3,4-dihydroquinazolin-2-yl)ethyl)carbamate;

(9H-fluoren-9-yl)methyl ((1S)-1-(5-chloro-4-oxo-3-(1-(2,2,2-trifluoroethyl)pyrrolidin-3-yl)-3,4-dihydroquinazolin-2-yl)ethyl)carbamate; and (S)-(9H-fluoren-9-yl)methyl (1-(5-chloro-3-(1-methylpiperidin-4-yl)-4-oxo-3,4-dihydroquinazolin-2-yl)ethyl)carbamate.

C. Preparation of a compound of formula (5) wherein B is 4-neopentylpiperazinyl, n is 1, $R^1$ is chloro, m is 0, $R^4$ is 2,6-diamino-5-cyanopyrimidin-4-yl, $R^3$ is methyl, and $R^5$ is hydrogen

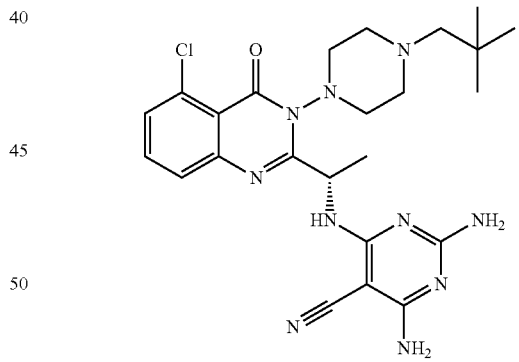

To a solution of (S)-2,4-diamino-6-(((3-(3-aminopropyl)-5-chloro-4-oxo-3,4-dihydroquinazolin-2-yl)(cyclopropyl)methyl)amino)pyrimidine-5-carbonitrile (200 mg, 0.45 mmol) in MeOH (5 mL), was added pivaldehyde (198 mg, 2.3 mmol). After stirring at room temp for 12 hour, sodium triacetoxyborohydride (1900 mg, 9.0 mmol) was added. After stirring for 3 hour at room temperature, saturated sodium bicarbonate solution (40 mL) was added and the mixture was extracted with EtOAc (3×40 mL). The combined organic layers were dried over sodium sulfate, filtered, and concentrated. The residue was purified on a reverse phase system run from 0 to 95% ACN in water (0.1% TFA) to give (S)-2,4-diamino-6-((1-(5-chloro-3-(4-neopentylpiperazin-1-yl)-4-oxo-3,4-dihydroquinazolin-2-yl)ethyl)amino)pyrimidine-5-carbonitrile as a solid. ES/MS 511.2 (M+H⁺).

D. Preparation of below compounds of formula (I), using the procedures described in Example 6C and Reaction Theme I:

(S)-(9H-fluoren-9-yl)methyl (1-(5-chloro-3-(4-isopropylpiperazin-1-yl)-4-oxo-3,4-dihydroquinazolin-2-yl)ethyl)carbamate;

(S)-(9H-fluoren-9-yl)methyl ((3-(4-benzylpiperazin-1-yl)-5-chloro-4-oxo-3,4-dihydroquinazolin-2-yl)(cyclopropyl)methyl)carbamate;

(S)-(9H-fluoren-9-yl)methyl (1-(3-(4-benzylpiperazin-1-yl)-5-chloro-4-oxo-3,4-dihydroquinazolin-2-yl)propyl)carbamate;

(S)-(9H-fluoren-9-yl)methyl (1-(3-(4-benzylpiperazin-1-yl)-5-chloro-8-fluoro-4-oxo-3,4-dihydroquinazolin-2-yl)propyl)carbamate;

(S)-(9H-fluoren-9-yl)methyl (1-(3-(4-(2-(tert-butoxy)ethyl)piperazin-1-yl)-5-chloro-4-oxo-3,4-dihydroquinazolin-2-yl)ethyl)carbamate;

(S)-(9H-fluoren-9-yl)methyl (1-(5-chloro-3-(4-(oxetan-3-yl)piperazin-1-yl)-4-oxo-3,4-dihydroquinazolin-2-yl)ethyl)carbamate; and (S)-(9H-fluoren-9-yl)methyl (1-(5-chloro-3-(4-neopentylpiperazin-1-yl)-4-oxo-3,4-dihydroquinazolin-2-yl)ethyl)carbamate.

Example 7. Preparation of a Compound of Formula (6)

A. Preparation of a compound of formula (6) wherein n is 1, $R^1$ is chloro, m is 0, B is 4-(4-trifluorphenylmethyl)piperazinyl, $R^3$ is ethyl, and $R^5$ is hydrogen

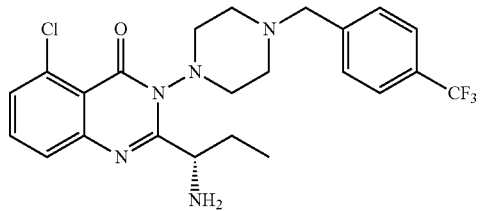 [SMILES: CC[C@H](N)c1nc2cccc(Cl)c2c(=O)n1N1CCN(Cc2ccc(C(F)(F)F)cc2)CC1]

Piperidine (0.092 mL, 0.93 mmol) was added to a solution of (S)-(9H-fluoren-9-yl)methyl (1-(5-chloro-4-oxo-3-(4-(4-(trifluoromethyl)benzyl)piperazin-1-yl)-3,4-dihydroquinazolin-2-yl)propyl)carbamate (187 mg, 0.266 mmol) in N,N-dimethylformamide (1.3 mL). The reaction mixture was stirred at 25° C. for 2 hour. EtOAc was added and the organic layer was washed with saturated sodium bicarbonate solution and brine. The organic layer was dried over sodium sulfate, filtered and concentrated. The resulting residue was loaded onto an EtOAc primed SiO₂ column Purification with chromatography by eluting with MeOH in EtOAc (0-20%) afforded (S)-2-(1-aminopropyl)-5-chloro-3-(4-(4-(trifluoromethyl)benzyl)piperazin-1-yl)quinazolin-4(3H)-one as a solid. ES/MS m/z=480.2 (M+H⁺).

B. Preparation of the below compounds of Formula (6), using the procedures described in Example 7A and Reaction Scheme I (S)-2-(1-aminopropyl)-5-chloro-3-(4-(4-fluorobenzyl)piperazin-1-yl)quinazolin-4(3H)-one;

(S)-2-(1-aminopropyl)-5-chloro-3-(4-(4-methoxybenzyl)piperazin-1-yl)quinazolin-4(3H)-one;

(S)-2-(1-aminoethyl)-5-chloro-3-(4-isopropylpiperazin-1-yl)quinazolin-4(3H)-one;

(S)-2-(amino(cyclopropyl)methyl)-3-(4-benzylpiperazin-1-yl)-5-chloroquinazolin-4(3H)-one;

(S)-2-(1-aminopropyl)-3-(4-benzylpiperazin-1-yl)-5-chloroquinazolin-4(3H)-one;

(S)-2-(1-aminopropyl)-3-(4-benzylpiperazin-1-yl)-5-chloro-8-fluoroquinazolin-4(3H)-one;

(S)-2-(1-aminoethyl)-3-(4-(2-(tert-butoxy)ethyl)piperazin-1-yl)-5-chloroquinazolin-4(3H)-one;

(S)-2-(1-aminoethyl)-5-chloro-3-(4-(oxetan-3-yl)piperazin-1-yl)quinazolin-4(3H)-one;

(S)-2-(1-aminoethyl)-5-chloro-3-(4-neopentylpiperazin-1-yl)quinazolin-4(3H)-one;

(S)-2-(1-aminoethyl)-5-chloro-3-(1-(2,2-difluoroethyl)piperidin-4-yl)quinazolin-4(3H)-one;

(S)-2-(1-aminoethyl)-5-chloro-3-(1-(2,2,2-trifluoroethyl)piperidin-4-yl)quinazolin-4(3H)-one;

(S)-2-(1-aminoethyl)-3-(1-benzylpiperidin-4-yl)-5-chloroquinazolin-4(3H)-one;

(S)-2-(1-aminoethyl)-5-chloro-3-(4-(2,2,2-trifluoroethyl)piperazin-1-yl)quinazolin-4(3H)-one;

(S)-2-(1-aminoethyl)-5-chloro-3-(4-(2,2-difluoroethyl)piperazin-1-yl)quinazolin-4(3H)-one;

(S)-2-(1-aminoethyl)-3-(4-benzylpiperazin-1-yl)-5-chloro-8-fluoroquinazolin-4(3H)-one; and 2-((S)-1-aminoethyl)-5-chloro-3-(1-(2,2,2-trifluoroethyl)pyrrolidin-3-yl)quinazolin-4(3H)-one.

Example 8. Preparation of a Compound of Formula (I)

A. Preparation of a compound of formula (I) wherein n is 1, $R^1$ is chloro, m is 0, B is 4-(4-trifluorophenylmethyl)piperazinyl, $R^3$ is ethyl, $R^5$ is hydrogen and $R^4$ is 2,6-diamino-5-cyanopyrimidin-4-yl

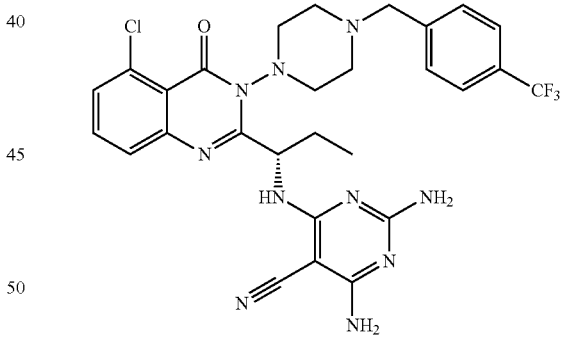

A mixture of (S)-2-(1-aminopropyl)-5-chloro-3-(4-(4-(trifluoromethyl)benzyl)piperazin-1-yl)quinazolin-4(3H)-one (38 mg, 0.079 mmol), N,N-diisopropylethylamine (20 □L, 0.115 mmol), and 2,4-diamino-6-chloropyrimidine-5-carbonitrile (14 mg, 0.80 mmol) in isopropyl alcohol (1 mL) was stirred in a microwave at 130° C. for 8 hours. The reaction mixture was adsorbed onto silica gel and loaded onto an EtOAc primed SiO₂ column. The title compound was then purified by eluting with MeOH in EtOAc (0-20%) to afford (S)-2,4-diamino-6-((1-(5-chloro-4-oxo-3-(4-(4-(trifluoromethyl)benzyl)piperazin-1-yl)-3,4-dihydroquinazolin-2-yl)propyl)amino)pyrimidine-5-carbonitrile. (Compound 87). ¹H NMR (400 MHz, DMSO-d₆) δ 7.75-7.67 (m, 3H), 7.60 (d, J=7.8 Hz, 2H), 7.54-7.48 (m, 2H), 6.65 (d, J=7.2 Hz, 1H), 6.59 (br s, 2H), 5.54-5.44 (m, 1H), 4.15-4.00 (m, 1H), 3.96-3.83 (m, 1H), 3.71-3.53 (m, 2H), 3.19-3.10 (m, 1H), 2.99-2.90 (m, 1H), 2.89-2.75 (m, 2H), 2.39-2.13 (m, 2H), 1.91 (s, 2H), 1.00 (t, J=7.3 Hz, 3H). ES/MS 613.2 (M+H$^+$).

B. Preparation of the below compounds of formula (I), using the procedures described in Example 8A and Reaction Scheme I:

(S)-2,4-diamino-6-((1-(5-chloro-3-(4-isopropylpiperazin-1-yl)-4-oxo-3,4-dihydroquinazolin-2-yl)ethyl)amino)pyrimidine-5-carbonitrile (Compound 88). 1H NMR (400 MHz, Deuterium Oxide) δ 9.75 (s, 1H), 7.74 (s, 2H), 7.55 (s, 3H), 7.00 (d, J=42.9 Hz, 1H), 6.72-6.43 (m, 4H), 6.34 (s, 1H), 5.70 (s, 1H), 4.24 (s, 1H), 3.87 (d, J=50.5 Hz, 2H), 2.81-2.58 (m, 2H), 1.45 (d, J=6.6 Hz, 2H), 1.24 (m, 1H), 0.96 (s, 6H). ES/MS 483.2 (M+H$^+$).

(S)-2-amino-4-((1-(5-chloro-4-oxo-3-(4-(4-(trifluoromethyl)benzyl)piperazin-1-yl)-3,4-dihydroquinazolin-2-yl)propyl)amino)-6-methylpyrimidine-5-carbonitrile (Compound 89). $^1$H NMR (400 MHz, DMSO-d$_6$) δ 7.75-7.68 (m, 3H), 7.59 (d, J=8.0 Hz, 2H), 7.52 (dd, J=7.9, 1.2 Hz, 1H), 7.51 (dd, J=8.1, 1.2 Hz, 1H), 7.27 (d, J=7.9 Hz, 1H), 5.55-5.42 (m, 1H), 4.15-4.02 (m, 1H), 3.97-3.83 (m, 1H), 3.70-3.62 (m, 1H), 3.60-3.53 (m, 1H), 3.17-3.09 (m, 1H), 3.00-2.91 (m, 1H), 2.89-2.73 (m, 2H), 2.38-2.22 (m, 4H), 2.16-2.04 (m, 1H), 1.96-1.83 (m, 2H), 1.01 (t, J=7.2 Hz, 3H). ES/MS 612.2 (M+H$^+$).

(S)-2-amino-4-((1-(5-chloro-3-(4-(4-fluorobenzyl)piperazin-1-yl)-4-oxo-3,4-dihydroquinazolin-2-yl)propyl)amino)-6-methylpyrimidine-5-carbonitrile (Compound 90). $^1$H NMR (400 MHz, DMSO-d$_6$) δ 7.71 (t, J=8.0 Hz, 1H), 7.57-7.47 (m, 2H), 7.42-7.33 (m, 2H), 7.26 (d, J=7.9 Hz, 1H), 7.22-7.11 (m, 2H), 5.52-5.43 (m, 1H), 4.09-4.00 (m, 1H), 3.92-3.82 (m, 1H), 3.57-3.40 (m, 2H), 3.16-3.08 (m, 1H), 2.97-2.89 (m, 1H), 2.87-2.71 (m, 2H), 2.35-2.20 (m, 4H), 2.11-1.99 (m, 1H), 1.95-1.83 (m, 2H), 1.00 (t, J=7.2 Hz, 3H). ES/MS 562.2 (M+H$^+$).

(S)-2,4-diamino-6-((1-(5-chloro-3-(4-(4-fluorobenzyl)piperazin-1-yl)-4-oxo-3,4-dihydroquinazolin-2-yl)propyl)amino)pyrimidine-5-carbonitrile (Compound 91). $^1$H NMR (400 MHz, DMSO-d$_6$) δ 7.70 (t, J=8.0 Hz, 1H), 7.55-7.49 (m, 2H), 7.43-7.34 (m, 2H), 7.23-7.13 (m, 2H), 6.64 (d, J=8.5 Hz, 1H), 6.59 (br s, 2H), 5.54-5.44 (m, 1H), 4.12-3.99 (m, 1H), 3.93-3.80 (m, 1H), 3.60-3.43 (m, 2H), 3.19-3.09 (m, 1H), 2.98-2.89 (m, 1H), 2.88-2.74 (m, 2H), 2.32-2.08 (m, 2H), 1.95-1.74 (m, 2H), 1.00 (t, J=7.2 Hz, 3H). ES/MS 563.2 (M+H$^+$).

(S)-2,4-diamino-6-((1-(5-chloro-3-(4-(4-methoxybenzyl)piperazin-1-yl)-4-oxo-3,4-dihydroquinazolin-2-yl)propyl)amino)pyrimidine-5-carbonitrile (Compound 92). $^1$H NMR (400 MHz, DMSO-d$_6$) δ 7.70 (t, J=8.0 Hz, 1H), 7.55-7.48 (m, 2H), 7.26 (d, J=8.2 Hz, 1H), 6.90 (d, J=8.6 Hz, 1H), 6.64 (d, J=8.3 Hz, 0H), 6.59 (br s, 2H), 5.55-5.42 (m, 1H), 4.10-3.97 (m, 1H), 3.91-3.80 (m, 1H), 3.79-3.71 (m, 3H), 3.18-3.05 (m, 1H), 2.95-2.71 (m, 3H), 2.29-2.02 (m, 2H), 1.98-1.71 (m, 2H), 1.00 (t, J=7.3 Hz, 3H). ES/MS 575.2 (M+H$^+$).

(S)-2,4-diamino-6-(((3-(4-benzylpiperazin-1-yl)-5-chloro-4-oxo-3,4-dihydroquinazolin-2-yl)(cyclopropyl)methyl)amino)pyrimidine-5-carbonitrile (Compound 93). 1H NMR (400 MHz, DMSO-d$_6$) δ 7.78-7.63 (m, 1H), 7.52 (ddt, J=11.9, 7.8, 1.0 Hz, 2H), 7.36-7.26 (m, 4H), 7.26-7.16 (m, 1H), 6.59 (s, 2H), 6.50 (d, J=8.0 Hz, 1H), 6.39 (s, 3H), 5.38 (d, J=9.7 Hz, 1H), 4.01 (td, J=11.1, 2.8 Hz, 1H), 3.90 (td, J=11.9, 11.3, 3.0 Hz, 1H), 2.91 (dd, J=23.4, 10.2 Hz, 2H), 2.69 (ddd, J=32.4, 11.3, 2.6 Hz, 2H), 2.41-2.26 (m, 1H), 2.01 (td, J=10.9, 9.7, 2.8 Hz, 1H), 1.43 (dtd, J=13.2, 8.1, 5.2 Hz, 1H), 0.61-0.38 (m, 3H), 0.39-0.24 (m, 1H). ES/MS 557.2 (M+H$^+$).

(S)-2,4-diamino-6-((1-(3-(4-benzylpiperazin-1-yl)-5-chloro-4-oxo-3,4-dihydroquinazolin-2-yl)propyl)amino)pyrimidine-5-carbonitrile (Compound 94). 1H NMR (400 MHz, DMSO-d$_6$) δ 7.70 (td, J=8.0, 1.0 Hz, 1H), 7.55-7.46 (m, 2H), 7.40-7.30 (m, 4H), 7.30-7.20 (m, 1H), 6.73-6.52 (m, 3H), 6.27 (s, 2H), 5.49 (td, J=8.4, 4.1 Hz, 1H), 4.14-3.96 (m, 1H), 3.87 (t, J=10.4 Hz, 1H), 3.63-3.40 (m, 2H), 3.14 (d, J=10.2 Hz, 1H), 2.99-2.88 (m, 1H), 2.83 (t, J=12.9 Hz, 2H), 2.36-2.22 (m, 1H), 2.22-2.07 (m, 1H), 1.96-1.73 (m, 2H), 1.04 (dd, J=6.1, 1.0 Hz, 1H), 1.00 (t, J=7.3 Hz, 3H). ES/MS 545.2 (M+H$^+$).

(S)-2,4-diamino-6-((1-(3-(4-benzylpiperazin-1-yl)-5-chloro-8-fluoro-4-oxo-3,4-dihydroquinazolin-2-yl)propyl)amino)pyrimidine-5-carbonitrile (Compound 95). 1H NMR (400 MHz, DMSO-d$_6$) δ 7.62 (dd, J=9.6, 8.7 Hz, 1H), 7.48 (dd, J=8.7, 4.4 Hz, 1H), 7.31 (d, J=4.4 Hz, 4H), 7.23 (h, J=4.1 Hz, 1H), 6.61 (d, J=8.1 Hz, 1H), 6.59-6.46 (m, 2H), 6.40-6.05 (m, 2H), 5.48 (td, J=8.2, 4.2 Hz, 1H), 4.05-3.92 (m, 1H), 3.87-3.78 (m, 1H), 3.57-3.35 (m, 2H), 3.10 (d, J=10.1 Hz, 1H), 2.91 (d, J=10.5 Hz, 1H), 2.78 (dd, J=17.9, 11.1 Hz, 2H), 2.34-2.17 (m, 1H), 2.09 (td, J=11.5, 3.1 Hz, 1H), 1.92-1.72 (m, 2H), 0.97 (t, J=7.3 Hz, 3H). ES/MS 563.2 (M+H$^+$).

(S)-2,4-diamino-6-((1-(3-(4-(2-(tert-butoxy)ethyl)piperazin-1-yl)-5-chloro-4-oxo-3,4-dihydroquinazolin-2-yl)ethyl)amino)pyrimidine-5-carbonitrile (Compound 96). 1H NMR (400 MHz, DMSO-d$_6$) δ 9.66 (d, J=11.3 Hz, 1H), 7.86-7.66 (m, 1H), 7.57 (ddt, J=7.6, 5.2, 1.2 Hz, 2H), 7.40 (s, 1H), 7.21 (s, 2H), 6.94 (s, 2H), 5.69 (p, J=6.8 Hz, 1H), 4.23 (dt, J=24.4, 12.3 Hz, 2H), 3.71-3.55 (m, 4H), 3.42-3.17 (m, 4H), 3.00 (d, J=11.2 Hz, 1H), 1.48 (d, J=6.8 Hz, 3H), 1.19 (d, J=1.0 Hz, 9H). ES/MS 541.2 (M+H$^+$).

(S)-2,4-diamino-6-((1-(5-chloro-3-(4-(oxetan-3-yl)piperazin-1-yl)-4-oxo-3,4-dihydroquinazolin-2-yl)ethyl)amino)pyrimidine-5-carbonitrile (Compound 97). 1H NMR (400 MHz, DMSO-d$_6$) δ 7.76 (td, J=8.0, 1.7 Hz, 2H), 7.64-7.45 (m, 2H), 7.27 (d, J=23.3 Hz, 2H), 5.73-5.57 (m, 1H), 4.73 (q, J=9.5, 7.0 Hz, 4H), 4.28-4.08 (m, 2H), 3.78 (t, J=5.1 Hz, 1H), 3.61-3.20 (m, J=25.4, 24.7 Hz, 4H), 2.98 (d, J=17.9 Hz, 1H), 2.80 (d, J=14.6 Hz, 1H), 1.70-1.52 (m, 2H), 1.52-1.37 (m, 3H). ES/MS 497.2 (M+H$^+$).

(S)-2,4-diamino-6-((1-(5-chloro-3-(4-neopentylpiperazin-1-yl)-4-oxo-3,4-dihydroquinazolin-2-yl)ethyl)amino)pyrimidine-5-carbonitrile (Compound 98). 1H NMR (400 MHz, DMSO-d$_6$) δ 7.72 (t, J=8.0 Hz, 1H), 7.53 (ddd, J=8.0, 4.0, 1.2 Hz, 2H), 6.87 (d, J=7.5 Hz, 1H), 6.57 (s, 2H), 6.33 (s, 2H), 5.62 (p, J=6.6 Hz, 1H), 4.09-3.98 (m, 1H), 3.97-3.87 (m, 1H), 3.03 (d, J=10.1 Hz, 1H), 2.86 (d, J=10.3 Hz, 1H), 2.77-2.66 (m, 2H), 2.61-2.51 (m, 1H), 2.42-2.31 (m, 1H), 2.07 (d, J=2.8 Hz, 2H), 1.46 (d, J=6.6 Hz, 3H), 0.87 (s, 9H). ES/MS 511.2 (M+H$^+$).

(S)-2,4-diamino-6-((1-(5-chloro-3-(1-(2,2-difluoroethyl)piperidin-4-yl)-4-oxo-3,4-dihydroquinazolin-2-yl)ethyl)amino)pyrimidine-5-carbonitrile (Compound 99). $^1$H NMR (400 MHz, DMSO-d$_6$) δ 7.76 (bs, 1H), 7.75 (dd, J=8.8, 8.4 Hz, 1H), 7.57 (m, 2H), 7.34 (bs, 2H), 7.12 (bs, 2H), 6.44 (m, 1H), 5.65 (m, 1H), 4.04 (br, 2H), 3.49 (br, 4H), 3.08 (m, 3H), 1.85 (m, 2H), 1.53 (d, J=6.4 Hz, 3H). ES/MS 504.2 (M+H$^+$).

(S)-2,4-diamino-6-((1-(5-chloro-4-oxo-3-(1-(2,2,2-trifluoroethyl)piperidin-4-yl)-3,4-dihydroquinazolin-2-yl)ethyl)amino)pyrimidine-5-carbonitrile (Compound 100). $^1$H NMR (400 MHz, DMSO-d$_6$) δ 8.31 (s, 1H), 7.89-7.67 (m, 3H), 7.67-7.49 (m, 2H), 5.67 (m, 1H), 3.90 (m, 1H), 3.20

(m, 2H), 2.99 (m, 2H), 2.83 (m, 2H), 2.42 (m, 1H), 1.98 (t, J=11.2 Hz, 1H), 1.61 (d, J=12.5 Hz, 1H), 1.52 (d, J=6.3 Hz, 3H), 1.50 (m, 1H). ES/MS 522.2 (M+H$^+$).

(S)-2,4-diamino-6-((1-(3-(1-benzylpiperidin-4-yl)-5-chloro-4-oxo-3,4-dihydroquinazolin-2-yl)ethyl)amino) pyrimidine-5-carbonitrile (Compound 101). $^1$H NMR (400 MHz, DMSO-d$_6$) δ 9.94 (s, 1H), 7.81-7.70 (m, 1H), 7.64 (bs, 1H), 7.60-7.53 (m, 2H), 7.53-7.45 (m, 5H), 7.25 (bs, 2H), 7.06 (bs, 2H), 5.66 (m, 1H), 4.37 (m, 1H), 4.22 (m, 2H), 3.48 (m, 2H), 3.19-2.98 (m, 3H), 1.90 (m, 2H), 1.52 (d, J=6.4 Hz, 3H), 1.50 (m, 1H). ES/MS 530.2 (M+H$^+$).

(S)-4-amino-6-((1-(5-chloro-4-oxo-3-(1-(2,2,2-trifluoroethyl)piperidin-4-yl)-3,4-dihydroquinazolin-2-yl)ethyl)amino)pyrimidine-5-carbonitrile (Compound 103). $^1$H NMR (400 MHz, DMSO-d$_6$) δ 8.64 (d, J=6.8 Hz, 1H), 8.32 (s, 1H), 8.06 (s, 2H), 7.75 (dd, J=8.3, 7.7 Hz, 1H), 7.65-7.52 (m, 2H), 5.75 (m, 1H), 4.26 (s, 1H), 3.96 (s, 2H), 3.55-3.21 (m, 2H), 3.09 (m, 3H), 2.95-2.61 (m, 1H), 1.86 (m, 2H), 1.56 (d, J=6.4 Hz, 3H). ES/MS 507.1 (M+H$^+$).

(S)-5-chloro-2-(1-((2,6-diamino-5-chloropyrimidin-4-yl) amino)ethyl)-3-(1-(2,2,2-trifluoroethyl)piperidin-4-yl) quinazolin-4(3H)-one (Compound 104). $^1$H NMR (400 MHz, DMSO-d$_6$) δ 8.18 (d, J=8.2 Hz, 1H), 7.74 (dd, J=8.0 Hz, 1H), 7.72 (br, 1H), 7.61 (dd, J=8.0, 1.2 Hz, 1H), 7.60 (bs, 2H), 7.56 (dd, J=7.8, 1.2 Hz, 1H), 5.62 (m, 1H), 3.84 (m, 1H), 3.18 (q, J=10.2 Hz, 2H), 3.02 (d, J=11.2 Hz, 1H), 2.90 (d, J=12.0 Hz, 1H), 2.81 (m, 2H), 2.41 (m, 1H), 1.93 (t, J=11.6 Hz, 1H), 1.61 (d, J=11.9 Hz, 1H), 1.54 (d, J=6.4 Hz, 3H), 1.46 (d, J=11.2 Hz, 1H). ES/MS 531.1 (M+H$^+$).

(S)-4-amino-6-((1-(5-chloro-3-(1-(2,2-difluoroethyl)piperidin-4-yl)-4-oxo-3,4-dihydroquinazolin-2-yl)ethyl)amino) pyrimidine-5-carbonitrile (Compound 105). $^1$H NMR (400 MHz, DMSO-d$_6$) δ 8.12 (s, 1H), 7.93 (d, J=7.2 Hz, 1H), 7.75 (dd, J=8.3, 7.7 Hz, 1H), 7.57 (m, 1H), 7.55 (m, 1H), 7.45 (bs, 2H), 6.49 (m, 1H), 5.67 (m, 1H), 4.35 (br, 3H), 3.55 (d, J=18.2 Hz, 4H), 3.17 (m, 2H), 1.93 (m, 2H), 1.53 (d, J=6.5 Hz, 3H). ES/MS 489.2 (M+H$^+$).

(S)-2-amino-4-((1-(5-chloro-4-oxo-3-(1-(2,2,2-trifluoroethyl)piperidin-4-yl)-3,4-dihydroquinazolin-2-yl)ethyl) amino)-6-methylpyrimidine-5-carbonitrile (Compound 106). $^1$H NMR (400 MHz, DMSO-d$_6$) δ 8.34 (s, 1H), 7.74 (dd, J=7.8 Hz, 1H), 7.59 (dd, J=8.2, 1.2 Hz, 1H), 7.55 (dd, J=7.8, 1.2 Hz, 1H), 5.68 (m, 1H), 3.90 (m, 1H), 3.18 (m, 2H), 3.03 (d, J=11.6 Hz, 1H), 2.91 (m, 1H), 2.84 (m, 2H), 2.42 (m, 1H), 2.33 (s, 3H), 1.89 (t, J=11.8 Hz, 1H), 1.62 (d, J=12.2 Hz, 1H), 1.54 (d, J=6.4 Hz, 3H), 1.50 (m, 1H). ES/MS 521.2 (M+H$^+$).

(S)-2,4-diamino-6-((1-(5-chloro-4-oxo-3-(4-(2,2,2-trifluoroethyl)piperazin-1-yl)-3,4-dihydroquinazolin-2-yl) ethyl)amino)pyrimidine-5-carbonitrile (Compound 107). $^1$H NMR (400 MHz, DMSO-d$_6$) δ 8.15 (bs, 3H), 7.86 (bs, 2H), 7.75 (dd, J=8.3, 7.8 Hz, 1H), 7.64-7.53 (m, 2H), 5.62 (m, 1H), 3.96 (qd, J=10.8, 2.8 Hz, 2H), 3.23 (q, J=10.1 Hz, 2H), 3.11-2.77 (m, 4H), 2.77-2.58 (m, 1H), 2.46-2.30 (m, 1H), 1.50 (d, J=6.7 Hz, 3H). ES/MS 523.2 (M+H$^+$).

(S)-5-chloro-2-(1-((2,6-diamino-5-chloropyrimidin-4-yl) amino)ethyl)-3-(4-(2,2,2-trifluoroethyl)piperazin-1-yl) quinazolin-4(3H)-one (Compound 108). $^1$H NMR (400 MHz, DMSO-d$_6$) δ 7.89 (d, J=7.3 Hz, 1H), 7.75 (dd, J=8.0 Hz, 1H), 7.59 (dd, J=8.2, 1.2 Hz, 1H), 7.56 (dd, J=7.8, 1.2 Hz, 1H), 7.54 (br, 3H), 5.57 (m, 1H), 4.11-3.82 (m, 2H), 3.39-3.09 (m, 2H), 2.97 (d, J=10.4 Hz, 2H), 2.92 (d, J=11.2 Hz, 1H), 2.85 (d, J=10.6 Hz, 1H), 2.73-2.58 (m, 1H), 2.43-2.26 (m, 1H), 1.51 (d, J=6.7 Hz, 3H). ES/MS 532.1 (M+H$^+$).

(S)-2-amino-4-((1-(5-chloro-4-oxo-3-(4-(2,2,2-trifluoroethyl)piperazin-1-yl)-3,4-dihydroquinazolin-2-yl)ethyl) amino)-6-methylpyrimidine-5-carbonitrile (Compound 109). $^1$H NMR (400 MHz, DMSO-d$_6$) δ 8.26 (s, 1H), 7.74 (dd, J=8.3, 7.8 Hz, 1H), 7.61 (bs, 2H), 7.56 (m, 2H), 5.63 (m, 1H), 3.96 (m, 2H), 3.21 (q, J=10.1 Hz, 2H), 3.10-2.79 (m, 4H), 2.64 (td, J=11.0, 2.4 Hz, 1H), 2.35 (s, 3H), 2.34-2.25 (m, 1H), 1.52 (d, J=6.7 Hz, 3H). ES/MS 522.2 (M+H$^+$).

(S)-2-amino-4-chloro-6-((1-(5-chloro-4-oxo-3-(4-(2,2,2-trifluoroethyl)piperazin-1-yl)-3,4-dihydroquinazolin-2-yl) ethyl)amino)pyrimidine-5-carbonitrile (Compound 110). $^1$H NMR (400 MHz, DMSO-d$_6$) δ 8.02 (d, J=7.1 Hz, 1H), 7.74 (dd, J=8.2, 7.8 Hz, 1H), 7.66 (bs, 1H), 7.56 (m, 2H), 7.40 (bs, 1H), 5.61 (m, 1H), 4.15-3.84 (m, 2H), 3.20 (q, J=10.0 Hz, 2H), 3.10-2.80 (m, 4H), 2.64 (td, J=11.5, 2.5 Hz, 1H), 2.30 (td, J=11.3, 2.9 Hz, 1H), 1.50 (d, J=6.7 Hz, 3H). ES/MS 542.1 (M+H$^+$).

(S)-2,4-diamino-6-((1-(5-chloro-3-(4-(2,2-difluoroethyl) piperazin-1-yl)-4-oxo-3,4-dihydroquinazolin-2-yl)ethyl) amino)pyrimidine-5-carbonitrile (Compound 111). $^1$H NMR (400 MHz, DMSO-d$_6$) δ 7.99 (bs, 2H), 7.79 (bs, 4H), 7.75 (dd, J=8.3, 7.8 Hz, 1H), 7.57 (dd, J=8.4, 1.2 Hz, 1H), 7.56 (dd, J=7.6, 1.2 Hz, 1H), 6.29 (m, 1H), 5.64 (m, 1H), 4.06 (m, 2H), 3.21-3.00 (m, 7H), 2.77 (m, 1H), 1.50 (d, J=6.7 Hz, 3H). ES/MS 505.2 (M+H$^+$).

(S)-5-chloro-2-(1-((2,6-diamino-5-chloropyrimidin-4-yl) amino)ethyl)-3-(4-(2,2-difluoroethyl)piperazin-1-yl)quinazolin-4(3H)-one (Compound 112). $^1$H NMR (400 MHz, DMSO-d$_6$) δ 7.85 (d, J=7.4 Hz, 1H), 7.75 (dd, J=8.2, 7.8 Hz, 1H), 7.61-7.55 (m, 2H), 7.57 (bs, 1H), 7.50 (bs, 3H), 6.25 (t, J=55.1 Hz, 1H), 5.59 (qd, J=7.2, 6.4 Hz, 1H), 4.03 (m, 2H), 3.05 (m, 6H), 2.72-2.60 (m, 1H), 2.46-2.26 (m, 1H), 1.51 (d, J=6.7 Hz, 3H). ES/MS 514.1 (M+H$^+$).

(S)-2-amino-4-chloro-6-((1-(5-chloro-3-(4-(2,2-difluoroethyl)piperazin-1-yl)-4-oxo-3,4-dihydroquinazolin-2-yl) ethyl)amino)pyrimidine-5-carbonitrile (Compound 113). $^1$H NMR (400 MHz, DMSO-d$_6$) δ 8.02 (d, J=7.2 Hz, 1H), 7.74 (dd, J=8.3, 7.7 Hz, 1H), 7.69 (bs, 1H), 7.57 (dd, J=8.4, 1.2 Hz, 1H), 7.56 (dd, J=7.6, 1.2 Hz, 1H), 7.37 (bs, 1H), 6.32 (t, J=54.7 Hz, 1H), 5.63 (qd, J=7.2, 6.8 Hz, 1H), 4.08 (dt, J=22.7, 11.5 Hz, 2H), 3.38-3.00 (m, 6H), 2.99-2.62 (m, 1H), 2.50 (m, 1H), 1.50 (d, J=6.7 Hz, 3H). ES/MS 524.1 (M+H$^+$).

(S)-2-amino-4-((1-(5-chloro-3-(4-(2,2-difluoroethyl)piperazin-1-yl)-4-oxo-3,4-dihydroquinazolin-2-yl)ethyl) amino)-6-methylpyrimidine-5-carbonitrile (Compound 114). $^1$H NMR (400 MHz, DMSO-d$_6$) δ 8.16 (s, 1H), 7.75 (dd, J=8.4, 7.6 Hz, 1H), 7.59 (bs, 3H), 7.59-7.53 (m, 2H), 6.33 (t, J=54.7 Hz, 1H), 5.65 (dq, J=6.8 Hz, 1H), 4.10 (dt, J=22.4, 11.6 Hz, 2H), 3.18 (s, 6H), 2.95-2.70 (m, 1H), 2.68-2.52 (m, 1H), 2.35 (s, 3H), 1.52 (d, J=6.7 Hz, 3H). ES/MS 504.2 (M+H$^+$).

(S)-5-chloro-3-(4-(2,2-difluoroethyl)piperazin-1-yl)-2-(1-(thiazolo[5,4-d]pyrimidin-7-ylamino)ethyl)quinazolin-4 (3H)-one (Compound 115). $^1$H NMR (400 MHz, DMSO-d$_6$) δ 9.32 (s, 1H), 8.66 (d, J=6.9 Hz, 1H), 8.42 (s, 1H), 7.70 (dd, J=8.0 Hz, 1H), 7.53 (dd, J=8.0, 1.2 Hz, 1H), 7.52 (dd, J=8.0, 1.2 Hz, 1H), 6.37 (t, J=54.5 Hz, 1H), 5.90 (m, 1H), 4.17 (ddd, J=23.2, 11.2 Hz, 2H), 3.57-3.13 (m, 6H), 3.13-2.61 (m, 2H), 1.62 (d, J=6.8 Hz, 3H). ES/MS 507.1 (M+H$^+$).

(S)-2,4-diamino-6-((1-(3-(4-benzylpiperazin-1-yl)-5-chloro-8-fluoro-4-oxo-3,4-dihydroquinazolin-2-yl)ethyl) amino)

amino)pyrimidine-5-carbonitrile (Compound 116). ¹H NMR (400 MHz, DMSO-d₆) δ 10.09 (s, 1H), 7.72 (dd, J=9.6, 8.7 Hz, 1H), 7.57 (dd, J=8.7, 4.4 Hz, 1H), 7.50 (s, 5H), 7.34 (bs, 2H), 7.12 (bs, 2H), 5.73 (m, 1H), 4.34 (d, J=12.7 Hz, 1H), 4.22 (d, J=14.2 Hz, 1H), 4.16 (m, 2H), 3.53 (d, J=11.8 Hz, 1H), 3.45-3.20 (m, 4H), 2.91 (m, 1H), 1.49 (d, J=6.7 Hz, 3H). ES/MS 549.2 (M+H⁺).

(S)-3-(4-benzylpiperazin-1-yl)-5-chloro-2-(1-((2,6-diamino-5-chloropyrimidin-4-yl)amino)ethyl)-8-fluoroquinazolin-4(3H)-one (Compound 117). ¹H NMR (400 MHz, DMSO-d₆) δ 10.22 (s, 1H), 7.71 (dd, J=9.6, 8.7 Hz, 1H), 7.57 (dd, J=8.8, 4.4 Hz, 1H), 7.50 (s, 5H), 7.28 (bs, 2H), 5.61 (m, 1H), 4.43-4.07 (m, 5H), 3.59-3.50 (m, 1H), 3.46-3.29 (m, 3H), 2.93 (m, 1H), 1.53 (d, J=6.8 Hz, 3H). ES/MS 558.2 (M+H⁺).

(S)-2-amino-4-((1-(3-(4-benzylpiperazin-1-yl)-5-chloro-8-fluoro-4-oxo-3,4-dihydroquinazolin-2-yl)ethyl)amino)-6-methylpyrimidine-5-carbonitrile (Compound 118). ¹H NMR (400 MHz, DMSO-d₆) δ 10.09 (s, 1H), 7.83 (d, J=7.4 Hz, 1H), 7.71 (dd, J=9.6, 8.7 Hz, 1H), 7.57 (dd, J=8.7, 4.4 Hz, 1H), 7.50 (s, 5H), 7.30 (bs, 1H), 5.72 (m, 1H), 4.35 (d, J=12.7 Hz, 1H), 4.23 (d, J=11.5 Hz, 1H), 4.20-4.04 (m, 2H), 3.54 (d, J=11.7 Hz, 1H), 3.43-3.22 (m, 4H), 2.81 (m, 1H), 2.32 (s, 3H), 1.52 (d, J=6.8 Hz, 3H). ES/MS 548.2 (M+H⁺).

2,4-diamino-6-(((1S)-1-(5-chloro-4-oxo-3-(1-(2,2,2-trifluoroethyl)pyrrolidin-3-yl)-3,4-dihydroquinazolin-2-yl)ethyl)amino)pyrimidine-5-carbonitrile (Compound 119). ¹H NMR (400 MHz, DMSO-d₆) δ 8.15 (bs, 1H), 7.86 (bs, 2H), 7.79-7.73 (m, 1H), 7.62-7.56 (m, 2H), 5.69-5.59 (m, 1H), 4.71 (m, 1H), 3.44 (m, 2H), 3.19 (m, 2H), 3.06 (m, 2H), 2.38-2.06 (m, 2H), 1.53 (m, 3H). ES/MS 508.1 (M+H⁺).

(S)-2-(1-((9H-purin-6-yl)amino)ethyl)-5-chloro-3-(1-methylpiperidin-4-yl)quinazolin-4(3H)-one (Compound 120). ¹H NMR (400 MHz, DMSO-d₆) δ 9.63 (s, 1H), 8.44 (br, 1H), 8.30 (m, 2H), 7.74 (dd, J=8.0 Hz, 1H), 7.53 (m, 2H), 5.81 (m, 1H), 4.67 (s, 1H), 3.62 (m, 1H), 3.44 (m, 1H), 3.29-3.03 (m, 3H), 2.78 (d, 3H), 2.75 (m, 1H), 2.20-1.98 (m, 2H), 1.67 (d, J=6.5 Hz, 3H). ES/MS 439.2 (M+H⁺).

(S)-2-(1-((6-amino-5-((5-fluoropyridin-2-yl)ethynyl)pyrimidin-4-yl)amino)ethyl)-3-(azetidin-3-yl)-5-chloroquinazolin-4(3H)-one (Compound 132). ES/MS 491.1 (M+H⁺).

(S)-5-chloro-2-(1-(imidazo[2,1-f][1,2,4]triazin-4-yl)pyrrolidin-2-yl)-3-(piperazin-1-yl)quinazolin-4(3H)-one (Compound 133). ES/MS 452.0 (M+H⁺).

(S)-4-amino-6-((1-(5-chloro-3-(1'-methyl-[1,4'-bipiperidin]-4-yl)-4-oxo-3,4-dihydroquinazolin-2-yl)ethyl)amino)pyrimidine-5-carbonitrile (Compound 134). ES/MS 522.2 (M+H⁺).

2-((S)-1-((9H-purin-6-yl)amino)ethyl)-5-chloro-3-(1-ethylpyrrolidin-3-yl)quinazolin-4(3H)-one (Compound 135). ES/MS 439.1 (M+H⁺).

2,4-diamino-6-(((S)-1-(5-chloro-4-oxo-3-((S)-tetrahydrofuran-3-yl)-3,4-dihydroquinazolin-2-yl)ethyl)amino)pyrimidine-5-carbonitrile (Compound 136). ¹H NMR (400 MHz, DMSO-d₆) δ 8.21 (d, J=7.6 Hz, 1H), 7.80 (s, 1H), 7.76-7.65 (m, 1H), 7.54 (ddt, J=9.0, 7.8, 1.2 Hz, 2H), 7.17-7.05 (m, 1H), 6.71 (dt, J=7.5, 1.0 Hz, 1H), 5.62 (p, J=6.6 Hz, 1H), 4.73-4.58 (m, 1H), 4.12 (q, J=7.7 Hz, 1H), 3.95-3.82 (m, 3H), 3.79 (td, J=7.9, 4.0 Hz, 1H), 2.29 (ddt, J=12.1, 7.9, 4.3 Hz, 1H), 1.90 (tt, J=11.9, 7.9 Hz, 1H), 1.48 (d, J=6.3 Hz, 3H). ES/MS 427.1 (M+H⁺).

2,4-diamino-6-(((S)-1-(5-chloro-4-oxo-3-((R)-tetrahydrofuran-3-yl)-3,4-dihydroquinazolin-2-yl)ethyl)amino)pyrimidine-5-carbonitrile (Compound 137). ¹H NMR (400 MHz, DMSO-d₆) δ 8.16 (s, 1H), 7.86 (s, 2H), 7.75 (ddd, J=8.0, 7.3, 1.2 Hz, 1H), 7.64-7.52 (m, 2H), 7.16 (ddd, J=8.4, 7.2, 1.2 Hz, 1H), 6.80-6.70 (m, 1H), 5.65 (h, J=6.7 Hz, 1H), 4.73 (dp, J=15.8, 8.4, 7.8 Hz, 1H), 4.17 (qd, J=7.9, 3.3 Hz, 1H), 3.97-3.81 (m, 2H), 3.76 (t, J=8.4 Hz, 1H), 2.35 (ddd, J=11.8, 7.8, 4.0 Hz, 1H), 2.19-2.04 (m, 1H), 1.59-1.51 (d, 3H). ES/MS 427.1 (M+H⁺).

(S)-2,4-diamino-6-((cyclopropyl(5,8-dichloro-3-cyclobutyl-4-oxo-3,4-dihydroquinazolin-2-yl)methyl)amino)pyrimidine-5-carbonitrile (Compound 138).

BIOLOGICAL EXAMPLES

The compounds of formula (I) were characterized for their enzymatic activity against the PI3K isoforms. The activities were measured using a time-resolved fluorescence resonance energy transfer (TR-FRET) assay. TR-FRET monitored the formation of 3,4,5-inositol triphosphate molecule that competed with fluorescently labeled PIPS for binding to the GRP-1 pleckstrin homology domain protein. An increase in phosphatidylinositide 3-phosphate product resulted in a decrease in TR-FRET signal as the labeled fluorophore was displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2× Km ATP (75-500 μM), 2 μM PIP2, 5% glycerol, 5 mM MgCl₂, 50 mM NaCl, 0.05% (v/v) Chaps, 1 mM dithiothreitol, and 1% (v/v) DMSO at the following concentrations for each isoform: PI3Kα, PI3Kβ, and PI3Kδ between 25 and 50 pM, and PI3Kγ at 2 nM. The compounds of Table 1 and Compound X ((S)-2,4-diamino-6-((1-(5-chloro-4-oxo-3-phenyl-3,4-dihydroquinazolin-2-yl)ethyl)amino)pyrimidine-5-carbonitrile) were added to the assay solution and incubated for 30 minutes at 25° C. The reactions were terminated with a final concentration of 10 mM EDTA, 10 nM labeled-PIPS, and 35 nM Europium labeled GRP-1 detector protein before reading TR-FRET on an Envision plate reader (Ex: 340 nm; Em: 615/665 nm; 100 is delay and 500 is read window).

The results were normalized based on positive (1 μM wortmanin) and negative (DMSO) controls, and the IC₅₀ values for PI3Kα, β, δ, and γ were calculated from the fit of the dose-response curves to a four-parameter equation. These assays generally produced results within 3-fold of the reported mean.

Table 2 summarizes the results of IC₅₀ (nM) values for PI3K isoforms β, δ, and γ. The results indicate that certain compounds of formula (I) inhibit both PI3Kδ and PI3Kβ. Also, Compound X exhibited PI3Kδ IC₅₀ of 0.2 nM, PI3Kβ IC₅₀ of 11 nM, and PI3Kγ IC₅₀ of 7 nM. The PI3Kγ/PI3Kβ ratio for Compound X is 0.6. The results indicate that certain compounds have greater selectivity for PI3Kβ over PI3Kγ compared to compound X. Compounds in Table 1a were analyzed using the same assay, and the results are summarized in Table 2a.

TABLE 2

The IC₅₀ values (nM) for PI3K isoforms β, δ, and γ.

| Compound | IC₅₀ (β) | IC₅₀ (δ) | IC₅₀ (γ) |
|---|---|---|---|
| 1 | 30 | 21 | 1740 |
| 2 | 950 | 260 | >10000 |

TABLE 2-continued

The IC$_{50}$ values (nM) for PI3K isoforms β, δ, and γ.

| Compound | IC$_{50}$ (β) | IC$_{50}$ (δ) | IC$_{50}$ (γ) |
|---|---|---|---|
| 3 | 8 | 12 | 580 |
| 4 | 290 | 82 | >10000 |
| 5 | 190 | 19 | >10000 |
| 6 | 460 | 68 | >10000 |
| 7 | 2 | 0.8 | 860 |
| 8 | 62 | 2 | >10000 |
| 9 | 9 | 2 | >10000 |
| 10 | 22 | 4 | >10000 |
| 11 | 4 | 4 | >10000 |
| 12 | 660 | 56 | >10000 |
| 13 | 180 | 33 | >10000 |
| 14 | 0.4 | 0.3 | 480 |
| 15 | 2 | 0.6 | 650 |
| 16 | 2 | 6 | 2600 |
| 17 | 3 | 4 | 2800 |
| 18 | 63 | 9 | >10000 |
| 19 | 3 | 1 | 1200 |
| 20 | 40 | 20 | >10000 |
| 21 | 2 | 0.7 | 890 |
| 22 | 15 | 5 | >10000 |
| 23 | 3 | 5 | >10000 |
| 24 | 2 | 3 | >10000 |
| 25 | 100 | 25 | >10000 |
| 26 | 2 | 2 | >10000 |
| 27 | 5600 | 830 | >10000 |
| 28 | 170 | 22 | 6400 |
| 29 | 91 | 31 | 3100 |
| 30 | 350 | 140 | >10000 |
| 31 | 78 | 19 | >10000 |
| 32 | 32 | 150 | >10000 |
| 33 | 4 | 14 | 7400 |
| 34 | 83 | 10 | >10000 |
| 35 | 570 | 93 | >10000 |
| 36 | 6 | 56 | 5700 |
| 37 | 39 | 3 | >10000 |
| 38 | 220 | 6 | 1500 |
| 39 | 4 | 3 | 5400 |
| 40 | 200 | 26 | >10000 |
| 41 | 210 | 24 | >10000 |
| 42 | 45 | 8 | >10000 |
| 43 | 30 | 4 | >10000 |
| 44 | 2 | 1 | 1800 |
| 46 | 2 | 1 | 2600 |
| 47 | 48 | 5 | >10000 |
| 48 | 3 | 1 | 3300 |
| 49 | 19 | 2 | >10000 |
| 50 | 15 | 2 | >10000 |
| 52 | 8 | 3 | 3100 |
| 53 | 27 | 6 | >10000 |
| 53 | 4 | 3 | 7000 |
| 54 | 4 | 2 | 1900 |
| 55 | 14 | 1 | >10000 |
| 56 | 21 | 230 | >10000 |
| 57 | 1 | 1 | 710 |
| 58 | 10 | 2 | >10000 |
| 59 | 73 | 280 | >10000 |
| 60 | 130 | 5 | >10000 |
| 61 | 150 | 0.9 | 400 |
| 62 | 820 | 9 | 8400 |
| 63 | 5 | 2 | >10000 |
| 64 | 94 | 9 | >10000 |
| 65 | 42 | 8 | >10000 |
| 66 | 370 | 13 | >10000 |
| 67 | 22 | 2 | >10000 |
| 68 | 1 | 3 | 2100 |
| 69 | 3 | 1 | 7400 |
| 70 | 14 | 3 | >10000 |
| 71 | 3 | 2 | 3200 |
| 72 | 28 | 11 | >10000 |
| 73 | 19 | 8 | >10000 |
| 74 | 570 | 32 | >10000 |
| 75 | 37 | 15 | >10000 |
| 76 | 25 | 2 | >10000 |
| 77 | 1 | 1 | 2900 |
| 78 | 18 | 2 | >10000 |
| 79 | 78 | 7 | >10000 |
| 80 | 25 | 4 | >10000 |
| 81 | 520 | 35 | >10000 |
| 82 | 480 | 22 | >10000 |
| 83 | 270 | 8 | >10000 |
| 84 | 32 | 2 | >10000 |
| 85 | 160 | 7 | >10000 |
| 86 | 83 | 3 | >10000 |
| 87 | 10000 | 57 | >10000 |
| 88 | 120 | 54 | 5800 |
| 89 | 4500 | 50 | >10000 |
| 90 | 52 | 23 | 2000 |
| 91 | 59 | 22 | 930 |
| 92 | 41 | 27 | 1400 |
| 93 | 48 | 18 | 1300 |
| 94 | 56 | 32 | 2900 |
| 95 | 96 | 38 | 2000 |
| 96 | 10 | 15 | 1000 |
| 97 | 93 | 15 | 460 |
| 98 | 4 | 5 | 1200 |
| 99 | 720 | 14 | 1600 |
| 100 | 970 | 15 | 1300 |
| 101 | 44 | 21 | 4200 |
| 102 | 57 | 2 | >10000 |
| 103 | 2200 | 10 | >10000 |
| 104 | 10000 | 260 | >10000 |
| 105 | 1900 | 9 | >10000 |
| 106 | 260 | 11 | 710 |
| 107 | 520 | 16 | 630 |
| 108 | 6100 | 170 | >10000 |
| 109 | 290 | 14 | 660 |
| 110 | 1400 | 41 | 2800 |
| 111 | 530 | 24 | 730 |
| 112 | 7800 | 280 | >10000 |
| 113 | 600 | 42 | 1300 |
| 114 | 300 | 26 | 560 |
| 115 | 1800 | 37 | 5300 |
| 116 | 13 | 15 | 470 |
| 117 | 570 | 220 | >10000 |
| 118 | 14 | 17 | 650 |
| 119 | 360 | 14 | 2900 |
| 120 | 1200 | 14 | >10000 |

TABLE 2A

The IC$_{50}$ values (nM) for PI3K isoforms β, δ, and γ.

| Compound | IC$_{50}$ (β) | IC$_{50}$ (δ) | IC$_{50}$ (γ) |
|---|---|---|---|
| 121 | 134 | 2 | 190 |
| 122 | 1800 | 19 | 2200 |
| 124 | 1300 | 390 | >10000 |
| 125 | 5 | 6 | 350 |
| 126 | 5 | 4 | 4900 |
| 127 | 28 | 13 | >10000 |
| 128 | 10 | 14 | >10000 |
| 129 | 120 | 4 | 5000 |
| 130 | 62 | 1 | >10000 |
| 131 | 450 | 6 | >10000 |
| 132 | 1000 | 250 | >10000 |
| 133 | 900 | 75 | >10000 |
| 134 | 2200 | 35 | >10000 |
| 135 | 4700 | 70 | >10000 |
| 136 | 192 | 2 | 259 |
| 137 | 47 | 5 | 229 |
| 138 | 58 | 1 | 524 |

All of the U.S. patents, U.S. patent application publications, U.S. patent applications, foreign patents, foreign patent applications and non-patent publications referred to in this specification are incorporated herein by reference, in their entirety to the extent not inconsistent with the present description. From the foregoing it will be appreciated that, although specific embodiments of the invention have been described herein for purposes of illustration, various modifications may be made without deviating from the spirit and scope of the present application.

What is claimed:
1. A compound having the structure of formula (I):

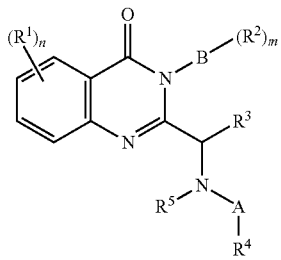

wherein
n is 0, 1, 2, or 3;
m is 0;
A is a single bond;
B is piperazinyl optionally substituted with halo, optionally substituted $C_{1-6}$ alkyl, optionally substituted $C_{3-8}$ heterocycloalkyl, $C_{1-6}$ haloalkyl, or optionally substituted $C_{3-8}$ cycloalkyl;
each $R^1$ is independently selected from halo, cyano, optionally substituted $C_{1-6}$ alkyl, optionally substituted $C_{1-6}$ haloalkyl, optionally substituted $C_{1-6}$ alkoxy, optionally substituted sulfonyl, optionally substituted $C_{3-8}$ aryl, optionally substituted $C_{3-8}$ heteroaryl, optionally substituted $C_{3-8}$ cycloalkyl, and optionally substituted $C_{3-8}$ heterocycloalkyl;
each $R^2$ is independently halo, optionally substituted $C_{1-6}$ alkyl, optionally substituted $C_{1-6}$ haloalkyl, or —$NH_2$;
$R^3$ is hydrogen, optionally substituted $C_{1-6}$ alkyl or $C_{3-8}$ cycloalkyl;
$R^4$ is a six- to twelve-membered heteroaryl having at least one aromatic group and at least two heteroatoms, wherein said heteroatom is N, wherein the heteroaryl is optionally substituted with one, two, or three members independently selected from halo, cyano, and —$NH_2$; and
$R^5$ is hydrogen,
or a pharmaceutically acceptable salt, isomer, or a mixture thereof.
2. The compound of claim 1, wherein
n is 1 or 2;
m is 0;
B is piperazinyl optionally substituted with one or two members independently selected from halo, $C_{1-6}$ alkyl, $C_{1-6}$ haloalkyl, $C_{3-8}$ heterocycloalkyl, and $C_{3-8}$ cycloalkyl, wherein $C_{3-8}$ heterocycloalkyl is optionally substituted with $C_{1-6}$ alkyl;
each $R^1$ is independently selected from halo, $C_{1-6}$ alkyl, and $C_{1-6}$ haloalkyl;
each $R^2$ is independently halo, —$NH_2$, $C_{1-6}$ alkyl, and $C_{1-6}$ haloalkyl;
$R^3$ is hydrogen or $C_{1-6}$ alkyl;
$R^4$ is a six- to twelve-membered heteroaryl having at least one aromatic ring and at least two nitrogen atoms, wherein the heteroaryl is optionally substituted with one, two, or three members independently selected from halo, cyano and —$NH_2$; and
$R^5$ is hydrogen,
or a pharmaceutically acceptable salt, isomer, or a mixture thereof.
3. The compound of claim 1, or a pharmaceutically acceptable salt, isomer, or a mixture thereof, wherein each $R^1$ is selected from chloro, bromo, fluoro, methyl, ethyl, and propyl.
4. The compound of claim 1, or a pharmaceutically acceptable salt, isomer, or a mixture thereof, wherein $R^3$ is selected from hydrogen, methyl, ethyl, propyl, butyl, cyclopropyl, and cyclobutyl.
5. The compound of claim 1, or a pharmaceutically acceptable salt, isomer, or a mixture thereof, wherein $R^4$ is a pyrimidinyl or pyrazinyl; wherein the pyrimidinyl or pyrazinyl is optionally substituted with two or three members independently selected from bromo, chloro, fluoro, cyano and —$NH_2$.
6. The compound of claim 1, or a pharmaceutically acceptable salt, isomer, or a mixture thereof, wherein $R^4$ is selected from purinyl, thiazolopyrimidinyl, pyridopyrimidinyl, thienopyrimidinyl, pyrrolopydmidinyl, furopyrimidinyl, and imidazotriazinyl, each of which is optionally substituted with one, two, or three members independently selected from bromo, chloro, fluoro, cyano and —$NH_2$.
7. A compound selected from the group consisting of:
(S)-2,4-diamino-6-(((5-chloro-3-(4-methylpiperazin-1-yl)-4-oxo-3,4-dihydroquinazolin-2-yl)(cyclopropyl)methyl)amino)pyrimidine-5-carbonitrile;
(S)-5-chloro-2-(cyclopropyl((2,6-diamino-5-chloropyrimidin-4-yl)amino)methyl)-3-(4-methylpiperazin-1-yl)quinazolin-4(3H)-one;
(S)-4-amino-6-((1-(5-chloro-3-(4-methylpiperazin-1-yl)-4-oxo-3,4-dihydroquinazolin-2-yl)ethyl)amino)pyrimidine-5-carbonitrile;
(S)-5-chloro-2-(1-((2,6-diamino-5-chloropyrimidin-4-yl)amino)ethyl)-8-fluoro-3-(piperazin-1-yl)quinazolin-4(3H)-one;
(S)-2-amino-4-((1-(5-chloro-8-fluoro-4-oxo-3-(piperazin-1-yl)-3,4-dihydroquinazolin-2-yl)ethyl)amino)-6-methylpyrimidine-5-carbonitrile;
(S)-3-amino-6-chloro-N-(1-(5-chloro-4-oxo-3-(piperazin-1-yl)-3,4-dihydroquinazolin-2-yl)ethyl)pyrazine-2-carboxamide;
(S)-3,5-diamino-6-chloro-N-(1-(5-chloro-4-oxo-3-(piperazin-1-yl)-3,4-dihydroquinazolin-2-yl)ethyl)pyrazine-2-carboxamide;
(S)-5-chloro-2-(1-(furo[3,2-d]pyrimidin-4-ylamino)ethyl)-3-(piperazin-1-yl)quinazolin-4(3H)-one;
(S)-5-chloro-2-(1-((5-chlorothieno[2,3-d]piperidin-4-yl)amino)ethyl)-3-(piperazin-1-yl)quinazolin-4(3H)-one;
(S)-2-amino-N-(1-(5-chloro-4-oxo-3-(piperazin-1-yl)-3,4-dihydroquinazolin-2-yl)ethyl)pyrazolo[1,5-a]pyrimidine-3-carboxamide;
(S)-2-(1-((6-amino-5-chloropyrimidin-4-yl)amino)ethyl)-5-chloro-3-(piperazin-1-yl)quinazolin-4(3H)-one;
(S)-2,4-diamino-6-((1-(5,8-di fluoro-4-oxo-3-(piperazin-1-yl)-3,4-dihydroquinazolin-2-yl)ethyl)amino)pyrimidine-5-carbonitrile;
(S)-5,8-difluoro-2-(1-(imidazo[2,1-f][1,2,4]triazin-4-ylamino)ethyl)-3-(piperazin-1-yl)quinazolin-4(3H)-one;
(S)-2-(cyclopropyl(imidazo[2,1-f][1,2,4]triazin-4-ylamino)methyl)-5,8-difluoro-3-(piperazin-1-yl)quinazolin-4(3H)-one;
(S)-5-chloro-2-(1-(imidazo[2,1-f][1,2,4]triazin-4-ylamino)propyl)-3-(piperazin-1-yl)quinazolin-4(3H)-one;

(S)-5-chloro-2-(cyclopropyl(imidazo[2,1-f][1,2,4]triazin-4-ylamino)methyl)-3-(piperazin-1-yl)quinazolin-4(3H)-one;

(S)-2-amino-4-((1-(5-chloro-4-oxo-3-(piperazin-1-yl)-3,4-dihydroquinazolin-2-yl)propyl)amino)-6-methylpyrimidine-5-carbonitrile;

(S)-2-amino-4-(((5-chloro-4-oxo-3-(piperazin-1-yl)-3,4-dihydroquinazolin-2-yl)(cyclopropyl)methyl)amino)-6-methylpyrimidine-5-carbonitrile;

(S)-5-chloro-2-(cyclopropyl(imidazo[2,1-f][1,2,4]triazin-4-ylamino)methyl)-8-fluoro-3-(piperazin-1-yl)quinazolin-4(3H)-one;

(S)-2,4-diamino-6-(((5-chloro-8-fluoro-4-oxo-3-(piperazin-1-yl)-3,4-dihydroquinazolin-2-yl)(cyclopropyl)methyl)amino)pyrimidine-5-carbonitrile;

(S)-5,8-dichloro-3-(piperazin-1-yl)-2-(1-(thiazolo[5,4-d]pyrimidin-7-ylamino)ethyl)quinazolin-4(3H)-one;

(S)-5-chloro-8-fluoro-3-(piperazin-1-yl)-2-(1-(thiazolo[5,4-d]pyrimidin-7-ylamino)ethyl)quinazolin-4(3H)-one;

(S)-5-chloro-2-(1-((6-chloropyrido[3,2-d]pyrimidin-4-yl)amino)ethyl)-8-fluoro-3-(piperazin-1-yl)quinazolin-4(3H)-one;

(S)-5,8-dichloro-2-(1-((6-chloropyrido[3,2-d]pyrimidin-4-yl)amino)ethyl)-3-(piperazin-1-yl)quinazolin-4(3H)-one;

(S)-2,4-diamino-6-((1-(5,8-dichloro-4-oxo-3-(piperazin-1-yl)-3,4-dihydroquinazolin-2-yl)ethyl)amino)pyrimidine-5-carbonitrile;

(S)-2,4-diamino-6-((1-(5-chloro-8-fluoro-4-oxo-3-(piperazin-1-yl)-3,4-dihydroquinazolin-2-yl)ethyl)amino)pyrimidine-5-carbonitrile;

(S)-4-amino-6-((1-(5-chloro-4-oxo-3-(piperazin-1-yl)-3,4-dihydroquinazolin-2-yl)ethyl)amino)pyrimidine-5-carbonitrile;

(S)-3-amino-N-(1-(5-chloro-4-oxo-3-(piperazin-1-yl)-3,4-dihydroquinazolin-2-yl)ethyl)pyrazine-2-carboxamide;

(S)-2,4-diamino-6-((1-(5-chloro-4-oxo-3-(piperazin-1-yl)-3,4-dihydroquinazolin-2-yl)ethyl)amino)pyrimidine-5-carbonitrile;

(S)-3-amino-N-(1-(5-chloro-4-oxo-3-(piperazin-1-yl)-3,4-dihydroquinazolin-2-yl)ethyl)-5,6-dimethylpyrazine-2-carboxamide;

(S)-5-chloro-2-(1-(imidazo[2,1-f][1,2,4]triazin-4-ylamino)ethyl)-3-(piperazin-1-yl)quinazolin-4(3H)-one;

(S)-2,4-diamino-6-((1-(5-chloro-4-oxo-3-(piperazin-1-yl)-3,4-dihydroquinazolin-2-yl)propyl)amino)pyrimidine-5-carbonitrile;

(S)-2-(1-((5-bromo-7H-pyrrolo[2,3-d]pyrimidin-4-yl)amino)ethyl)-5-chloro-3-(piperazin-1-yl)quinazolin-4(3H)-one;

(S)-5-chloro-3-(piperazin-1-yl)-2-(1-(thiazolo[5,4-d]pyrimidin-7-ylamino)ethyl)quinazolin-4(3H)-one;

(S)-5-chloro-2-(1-((6-chloropyrido[3,2-d]pyrimidin-4-yl)amino)ethyl)-3-(piperazin-1-yl)quinazolin-4(3H)-one;

(S)-5-chloro-2-(1-((2,6-diamino-5-chloropyrimidin-4-yl)amino)ethyl)-3-(piperazin-1-yl)quinazolin-4(3H)-one;

(S)-5-chloro-3-(piperazin-1-yl)-2-(1-(pyrido[3,2-d]pyrimidin-4-ylamino)ethyl)quinazolin-4(3H)-one;

(S)-4-amino-6-((1-(5-chloro-4-oxo-3-(piperazin-1-yl)-3,4-dihydroquinazolin-2-yl)-3-methylbutyl)amino)pyrimidine-5-carbonitrile;

(S)-2,4-diamino-6-((1-(5-chloro-4-oxo-3-(piperazin-1-yl)-3,4-dihydroquinazolin-2-yl)-3-methylbutyl)amino)pyrimidine-5-carbonitrile;

(S)-4-amino-6-((1-(5,8-dichloro-4-oxo-3-(piperazin-1-yl)-3,4-dihydroquinazolin-2-yl)ethyl)amino)pyrimidine-5-carbonitrile;

(S)-2,4-diamino-6-(((5-chloro-4-oxo-3-(piperazin-1-yl)-3,4-dihydroquinazolin-2-yl)(cyclopropyl)methyl)amino)pyrimidine-5-carbonitrile;

(S)-5-chloro-2-(cyclopropyl(thiazolo[5,4-d]pyrimidin-7-ylamino)methyl)-3-(piperazin-1-yl)quinazolin-4(3H)-one;

(S)-4-amino-6-((1-(5-chloro-4-oxo-3-(piperazin-1-yl)-3,4-dihydroquinazolin-2-yl)propyl)amino)pyrimidine-5-carbonitrile;

(S)-5-chloro-3-(piperazin-1-yl)-2-(1-(thiazolo[5,4-d]pyrimidin-7-ylamino)propyl)quinazolin-4(3H)-one;

(S)-2,4-diamino-6-((1-(5-chloro-3-(4-isopropylpiperazin-1-yl)-4-oxo-3,4-dihydroquinazolin-2-yl)ethyl)amino)pyrimidine-5-carbonitrile;

(S)-4-amino-6-(((5-chloro-4-oxo-3-(piperazin-1-yl)-3,4-dihydroquinazolin-2-yl)(cyclopropyl)methyl)amino)pyrimidine-5-carbonitrile;

(S)-2,4-diamino-6-((1-(5-chloro-3-(4-methylpiperazin-1-yl)-4-oxo-3,4-dihydroquinazolin-2-yl)ethyl)amino)pyrimidine-5-carbonitrile;

(S)-2,4-diamino-6-((1-(8-chloro-6-fluoro-4-oxo-3-(piperazin-1-yl)-3,4-dihydroquinazolin-2-yl)ethyl)amino)pyrimidine-5-carbonitrile;

(S)-2,4-diamino-6-((cyclopropyl(5,8-difluoro-4-oxo-3-(piperazin-1-yl)-3,4-dihydroquinazolin-2-yl)methyl)amino)pyrimidine-5-carbonitrile;

(S)-5-chloro-2-(1-(imidazo[2,1-f][1,2,4]triazin-4-yl)pyrrolidin-2-yl)-3-(piperazin-1-yl)quinazolin-4(3H)-one;

(S)-2,4-diamino-6-((1-(3-(4-benzylpiperazin-1-yl)-5-chloro-4-oxo-3,4-dihydroquinazolin-2-yl)ethyl)amino)pyrimidine-5-carbonitrile;

(S)-2,4-diamino-6-((1-(5-chloro-4-oxo-3-(4-(4-(trifluoromethyl)benzyl)piperazin-1-yl)-3,4-dihydroquinazolin-2-yl)propyl)amino)pyrimidine-5-carbonitrile;

(S)-2-amino-4-((1-(5-chloro-4-oxo-3-(4-(4-(trifluoromethyl)benzyl)piperazin-1-yl)-3,4-dihydroquinazolin-2-yl)propyl)amino)-6-methylpyrimidine-5-carbonitrile;

(S)-2-amino-4-(1(5-chloro-3-(4-(4-fluorobenzyl)piperazin-1-yl)-4-oxo-3,4-dihydroquinazolin-2-yl)propyl)amino)-6-methylpyrimidine-5-carbonitrile;

(S)-2,4-diamino-6-((1-(5-chloro-3-(4-(4-fluorobenzyl)piperazin-1-yl)-4-oxo-3,4-dihydroquinazolin-2-yl)propyl)amino)pyrimidine-5-carbonitrile;

(S)-2,4-diamino-6-((1-(5-chloro-3-(4-(4-methoxybenzyl)piperazin-1-yl)-4-oxo-3,4-dihydroquinazolin-2-yl)propyl)amino)pyrimidine-5-carbonitrile;

(S)-2,4-diamino-6-(((3-(4-benzylpiperazin-1-yl)-5-chloro-4-oxo-3,4-dihydroquinazolin-2-yl)(cyclopropyl)methyl)amino)pyrimidine-5-carbonitrile;

(S)-2,4-diamino-6-((1-(3-(4-benzylpiperazin-1-yl)-5-chloro-4-oxo-3,4-dihydroquinazolin-2-yl)propyl)amino)pyrimidine-5-carbonitrile;

(S)-2,4-diamino-6-((1-(3-(4-benzylpiperazin-1-yl)-5-chloro-8-fluoro-4-oxo-3,4-dihydroquinazolin-2-yl)propyl)amino)pyrimidine-5-carbonitrile;

(S)-2,4-diamino-6-((1-(3-(4-(2-(tert-butoxy)ethyl)piperazin-1-yl)-5-chloro-4-oxo-3,4-dihydroquinazolin-2-yl)ethyl)amino)pyrimidine-5-carbonitrile;

(S)-2,4-diamino-6-((1-(5-chloro-3-(4-(oxetan-3-yl)piperazin-1-yl)-4-oxo-3,4-dihydroquinazolin-2-yl)ethyl)amino)pyrimidine-5-carbonitrile;

(S)-2,4-diamino-6-((1-(5-chloro-3-(4-neopentylpiperazin-1-yl)-4-oxo-3,4-dihydroquinazolin-2-yl)ethyl)amino)pyrimidine-5-carbonitrile;

(S)-2,4-diamino-6-((1-(5-chloro-4-oxo-3-(4-(2,2,2-trifluoroethyl)piperazin-1-yl)-3,4-dihydroquinazolin-2-yl)ethyl)amino)pyrimidine-5-carbonitrile;

(S)-5-chloro-2-(1-((2,6-diamino-5-chloropyrimidin-4-yl)amino)ethyl)-3-(4-(2,2,2-trifluoroethyl)piperazin-1-yl)quinazolin-4(3H)-one;

(S)-2-amino-4-((1-(5-chloro-4-oxo-3-(4-(2,2,2-trifluoroethyl)piperazin-1-yl)-3,4-dihydroquinazolin-2-yl)ethyl)amino)-6-methylpyrimidine-5-carbonitrile;

(S)-2-amino-4-chloro-6-((1-(5-chloro-4-oxo-3-(4-(2,2,2-trifluoroethyl)piperazin-1-yl)-3,4-dihydroquinazolin-2-yl)ethyl)amino)pyrimidine-5-carbonitrile;

(S)-2,4-diamino-6-((1-(5-chloro-3-(4-(2,2-difluoroethyl)piperazin-1-yl)-4-oxo-3,4-dihydroquinazolin-2-yl)ethyl)amino)pyrimidine-5-carbonitrile;

(S)-5-chloro-2-(1-((2,6-diamino-5-chloropyrimidin-4-yl)amino)ethyl)-3-(4-(2,2-difluoroethyl)piperazin-1-yl)quinazolin-4(3H)-one;

(S)-2-amino-4-chloro-6-((1-(5-chlforo-3-(4-(2,2-difluoroethyl)piperazin-1-yl)-4-oxo-3,4-dihydroquinazolin-2-yl)ethyl)amino)pyrimidine-5-carbonitrile;

(S)-2-amino-4-((1-(5-chloro-3-(4-(2,2-difluoroethyl)piperazin-1-yl)-4-oxo-3,4-dihydroquinazolin-2-yl)ethyl)amino)-6-methylpyrimidine-5-carbonitrile;

(S)-5-chloro-3-(4-(2,2-difluoroethyl)piperazin-1-yl)-2-(1-(thiazolo[5,4-d]pyrimidin-7-ylamino)ethyl)quinazolin-4(3H)-one;

(S)-2,4-diamino-6-((1-(3-(4-benzylpiperazin-1-yl)-5-chloro-8-fluoro-4-oxo-3,4-dihydroquinazolin-2-yl)ethyl)amino)pyrimidine-5-carbonitrile;

(S)-3-(4-benzylpiperazin-1-yl)-5-chloro-2-(1-((2,6-diamino-5-chloropyrimidin-4-yl)amino)ethyl)-8-fluoroquinazolin-4(3H)-one;

(S)-2-amino-4-((1-(3-(4-benzylpiperazin-1-yl)-5-chloro-8-fluoro-4-oxo-3,4-dihydroquinazolin-2-yl)ethyl)amino)-6-methylpyrimidine-5-carbonitrile; and (R)-2,4-diamino-6-(2-(3-(4-benzylpiperazin-1-yl)-5-fluoro-4-oxo-3,4-dihydroquinazolin-2-yl)pyrrolidin-1-yl)pyrimidine-5-carbonitrile, or a pharmaceutically acceptable salt thereof.

8. The compound of claim 7, or a pharmaceutically acceptable salt thereof, wherein the compound is an atropisomer.

9. A pharmaceutical comprising the compound of claim 7, or a pharmaceutically acceptable salt thereof, and at least one pharmaceutically acceptable vehicle.

10. A kit comprising the compound of claim 7, or a pharmaceutically acceptable salt thereof, and a label and/or instructions for use.

11. A compound selected from the table below:

| Compound | Structure | Compound | Structure |
|---|---|---|---|
| 1 | 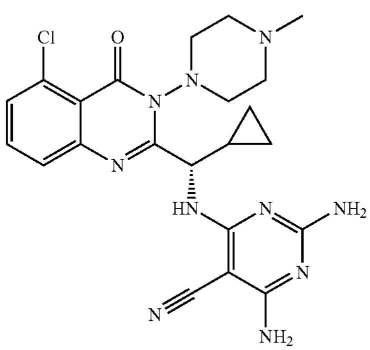 [SMILES: CN1CCN(n2c([C@@H](Nc3nc(N)nc(N)c3C#N)C3CC3)nc3cccc(Cl)c3c2=O)CC1] | 61 | 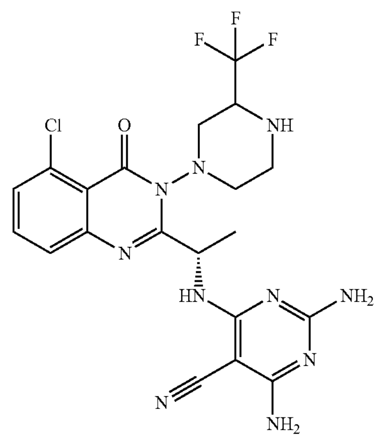 [SMILES: C[C@H](Nc1nc(N)nc(N)c1C#N)c1nc2cccc(Cl)c2c(=O)n1N1CCNC(C(F)(F)F)C1] |
| 2 | 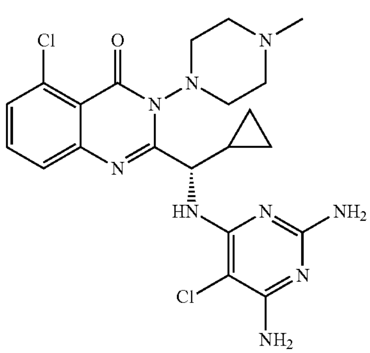 [SMILES: CN1CCN(n2c([C@@H](Nc3nc(N)nc(N)c3Cl)C3CC3)nc3cccc(Cl)c3c2=O)CC1] | 62 | 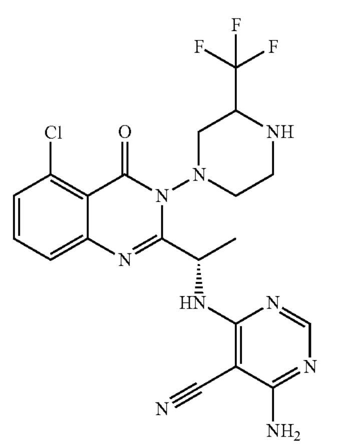 [SMILES: C[C@H](Nc1ncnc(N)c1C#N)c1nc2cccc(Cl)c2c(=O)n1N1CCNC(C(F)(F)F)C1] |

-continued

| Compound | Structure | Compound | Structure |
|---|---|---|---|
| 3 | 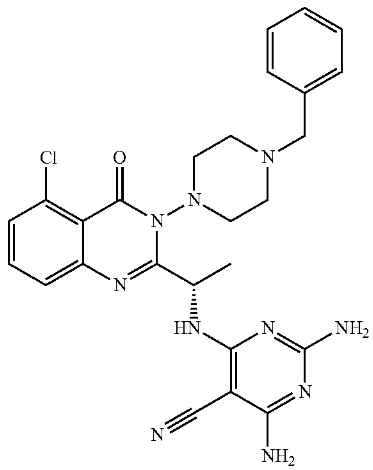 [SMILES: C[C@H](Nc1nc(N)nc(N)c1C#N)c1nc2cccc(Cl)c2c(=O)n1N1CCN(Cc2ccccc2)CC1] | 63 | 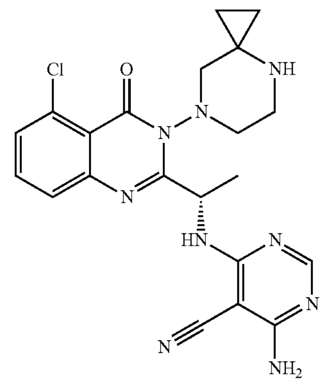 [SMILES: C[C@H](Nc1ncnc(N)c1C#N)c1nc2cccc(Cl)c2c(=O)n1N1CCNC2(CC2)C1] |
| 5 | 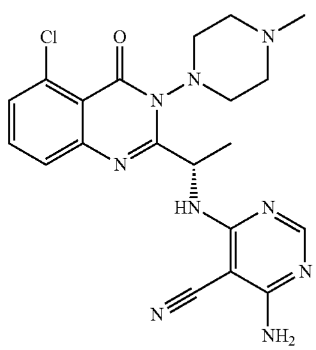 [SMILES: C[C@H](Nc1ncnc(N)c1C#N)c1nc2cccc(Cl)c2c(=O)n1N1CCN(C)CC1] | 65 | 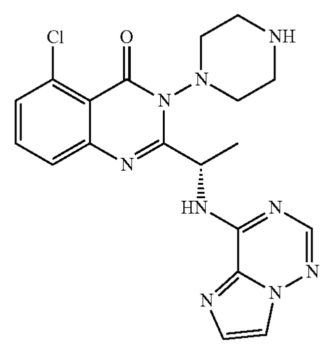 [SMILES: C[C@H](Nc1ncnn2ccnc12)c1nc2cccc(Cl)c2c(=O)n1N1CCNCC1] |
| 20 | 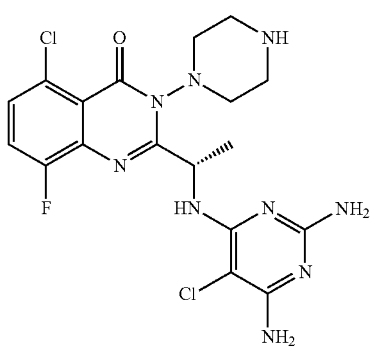 [SMILES: C[C@H](Nc1nc(N)nc(N)c1Cl)c1nc2c(F)ccc(Cl)c2c(=O)n1N1CCNCC1] | 68 | 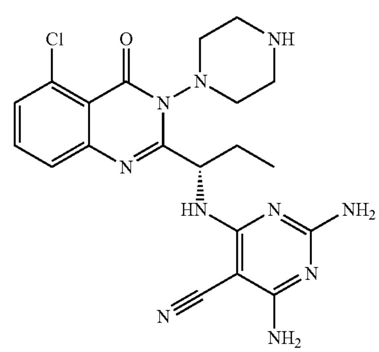 [SMILES: CC[C@H](Nc1nc(N)nc(N)c1C#N)c1nc2cccc(Cl)c2c(=O)n1N1CCNCC1] |
| 21 | 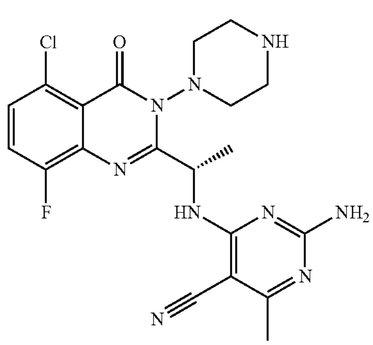 [SMILES: Cc1nc(N)nc(N[C@@H](C)c2nc3c(F)ccc(Cl)c3c(=O)n2N2CCNCC2)c1C#N] | 69 | 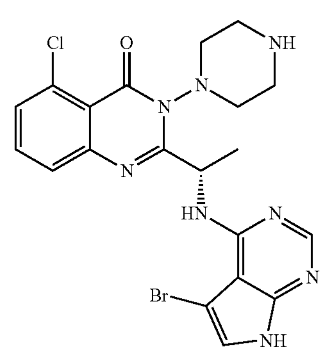 [SMILES: C[C@H](Nc1ncnc2[nH]cc(Br)c12)c1nc2cccc(Cl)c2c(=O)n1N1CCNCC1] |

-continued

| Compound | Structure | Compound | Structure |
|---|---|---|---|
| 70 | 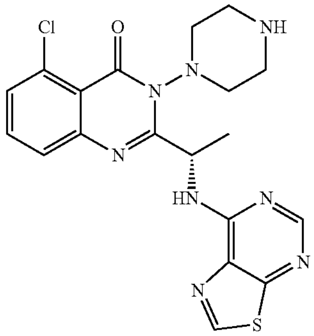 [SMILES: C[C@H](Nc1ncnc2scnc12)c1nc2cccc(Cl)c2c(=O)n1N1CCNCC1] | 71 | 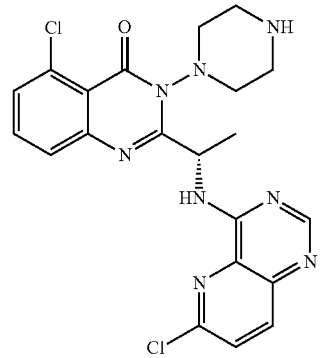 [SMILES: C[C@H](Nc1ncnc2ccc(Cl)nc12)c1nc2cccc(Cl)c2c(=O)n1N1CCNCC1] |
| 72 | 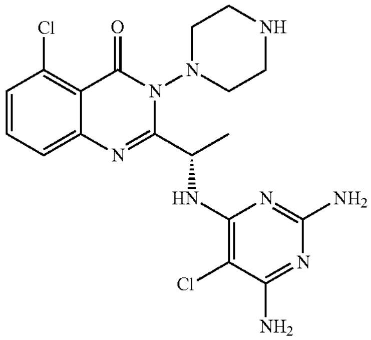 [SMILES: C[C@H](Nc1nc(N)nc(N)c1Cl)c1nc2cccc(Cl)c2c(=O)n1N1CCNCC1] | 73 | 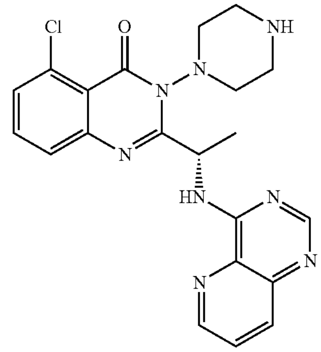 [SMILES: C[C@H](Nc1ncnc2cccnc12)c1nc2cccc(Cl)c2c(=O)n1N1CCNCC1] |
| 74 | 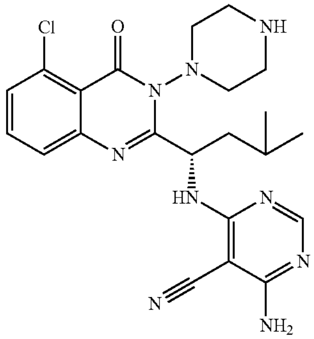 [SMILES: CC(C)C[C@H](Nc1ncnc(N)c1C#N)c1nc2cccc(Cl)c2c(=O)n1N1CCNCC1] | 75 | 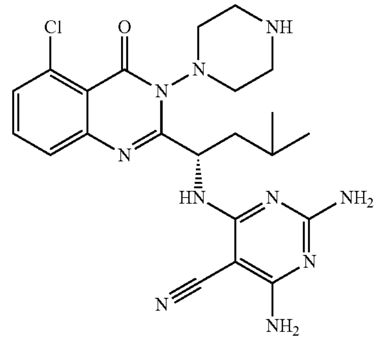 [SMILES: CC(C)C[C@H](Nc1nc(N)nc(N)c1C#N)c1nc2cccc(Cl)c2c(=O)n1N1CCNCC1] |
| 76 | 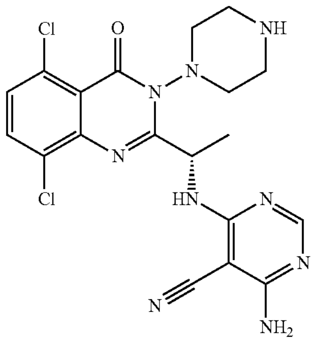 [SMILES: C[C@H](Nc1ncnc(N)c1C#N)c1nc2c(Cl)ccc(Cl)c2c(=O)n1N1CCNCC1] | 77 | 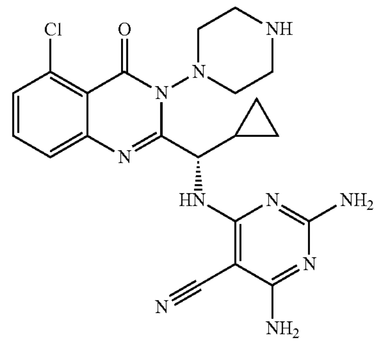 [SMILES: N#Cc1c(N)nc(N)nc1N[C@H](c1nc2cccc(Cl)c2c(=O)n1N1CCNCC1)C1CC1] |

-continued

| Compound | Structure | Compound | Structure |
| --- | --- | --- | --- |
| 78 | 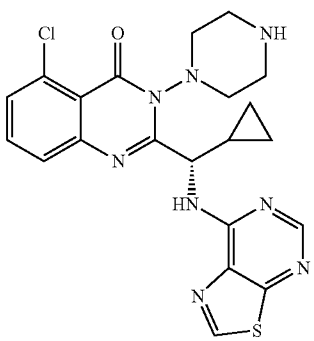 [SMILES: O=c1c2c(Cl)cccc2nc([C@@H](Nc2ncnc3scnc23)C2CC2)n1N1CCNCC1] | 79 | 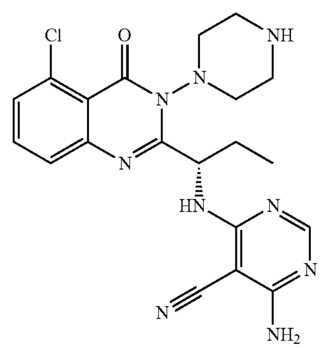 [SMILES: CC[C@H](Nc1ncnc(N)c1C#N)c1nc2cccc(Cl)c2c(=O)n1N1CCNCC1] |
| 80 | 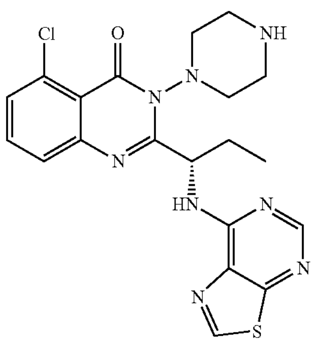 [SMILES: CC[C@H](Nc1ncnc2scnc12)c1nc2cccc(Cl)c2c(=O)n1N1CCNCC1] | 7 | 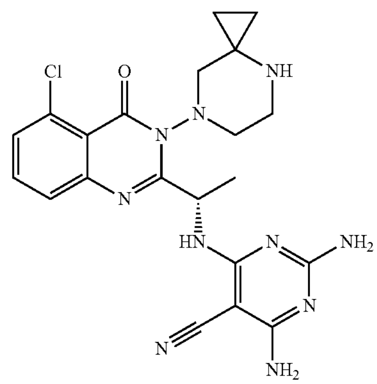 [SMILES: C[C@H](Nc1nc(N)nc(N)c1C#N)c1nc2cccc(Cl)c2c(=O)n1N1CCNC2(CC2)C1] |
| 88 | 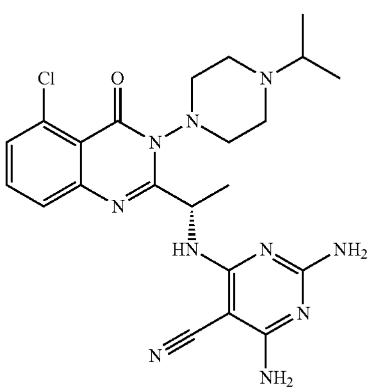 [SMILES: CC(C)N1CCN(n2c([C@H](C)Nc3nc(N)nc(N)c3C#N)nc3cccc(Cl)c3c2=O)CC1] | 89 | 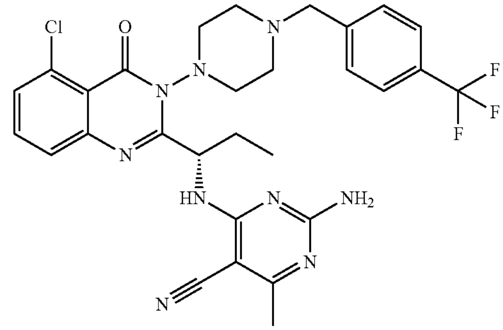 [SMILES: CC[C@H](Nc1nc(N)nc(C)c1C#N)c1nc2cccc(Cl)c2c(=O)n1N1CCN(Cc2ccc(C(F)(F)F)cc2)CC1] |
| 90 | 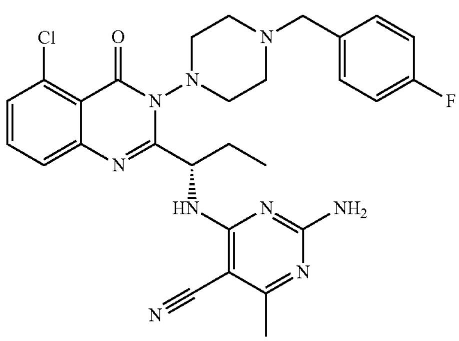 [SMILES: CC[C@H](Nc1nc(N)nc(C)c1C#N)c1nc2cccc(Cl)c2c(=O)n1N1CCN(Cc2ccc(F)cc2)CC1] | 91 | 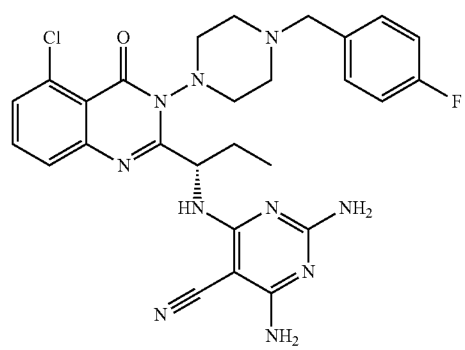 [SMILES: CC[C@H](Nc1nc(N)nc(N)c1C#N)c1nc2cccc(Cl)c2c(=O)n1N1CCN(Cc2ccc(F)cc2)CC1] |

-continued

| Compound | Structure | Compound | Structure |
| --- | --- | --- | --- |
| 118 | 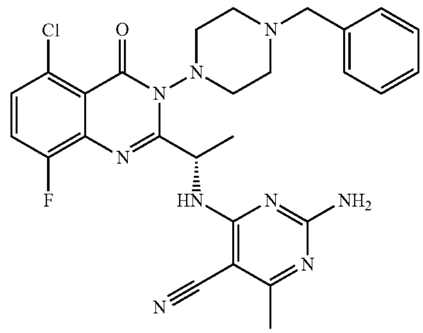 [SMILES: Cc1nc(N)nc(N[C@@H](C)c2nc3c(F)ccc(Cl)c3c(=O)n2N2CCN(Cc3ccccc3)CC2)c1C#N] | 92 | 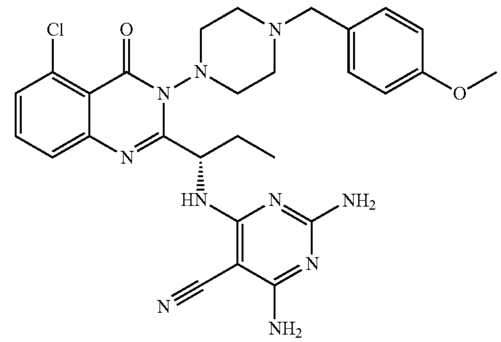 [SMILES: CC[C@H](Nc1nc(N)nc(N)c1C#N)c1nc2cccc(Cl)c2c(=O)n1N1CCN(Cc2ccc(OC)cc2)CC1] |
| 33 | 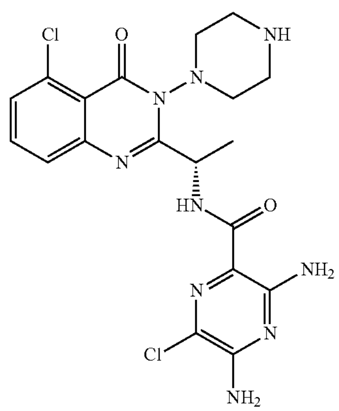 [SMILES: C[C@H](NC(=O)c1nc(Cl)c(N)nc1N)c1nc2cccc(Cl)c2c(=O)n1N1CCNCC1] | 93 | 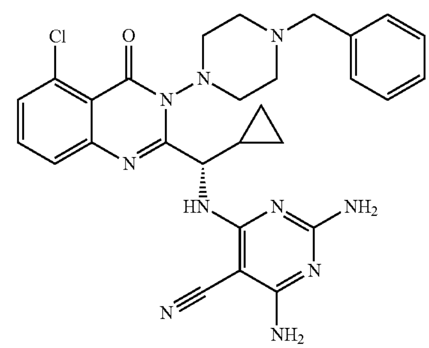 [SMILES: N#Cc1c(N)nc(N)nc1N[C@H](c1nc2cccc(Cl)c2c(=O)n1N1CCN(Cc2ccccc2)CC1)C1CC1] |
| 34 | 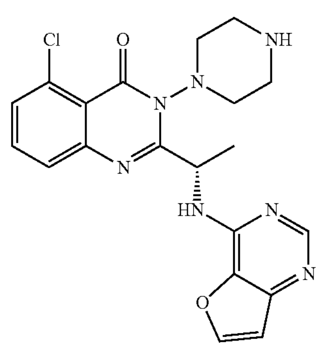 [SMILES: C[C@H](Nc1ncnc2ccoc12)c1nc2cccc(Cl)c2c(=O)n1N1CCNCC1] | 94 | 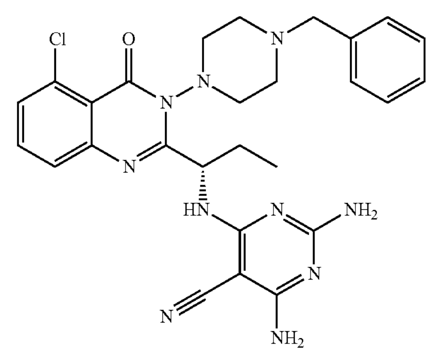 [SMILES: CC[C@H](Nc1nc(N)nc(N)c1C#N)c1nc2cccc(Cl)c2c(=O)n1N1CCN(Cc2ccccc2)CC1] |
| 35 | 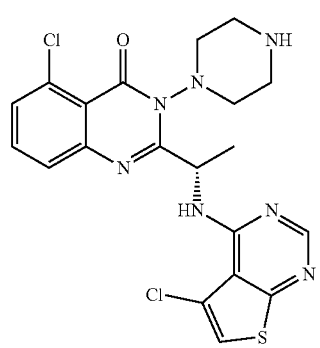 [SMILES: C[C@H](Nc1ncnc2scc(Cl)c12)c1nc2cccc(Cl)c2c(=O)n1N1CCNCC1] | 95 | 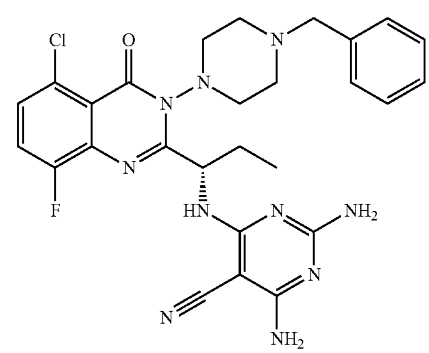 [SMILES: CC[C@H](Nc1nc(N)nc(N)c1C#N)c1nc2c(F)ccc(Cl)c2c(=O)n1N1CCN(Cc2ccccc2)CC1] |

-continued

| Compound | Structure | Compound | Structure |
|---|---|---|---|
| 36 | 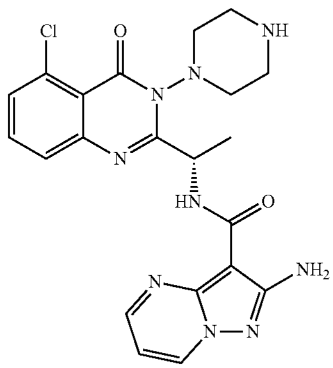 [SMILES: C[C@H](NC(=O)c1c(N)nn2cccnc12)c1nc2cccc(Cl)c2c(=O)n1N1CCNCC1] | 96 | 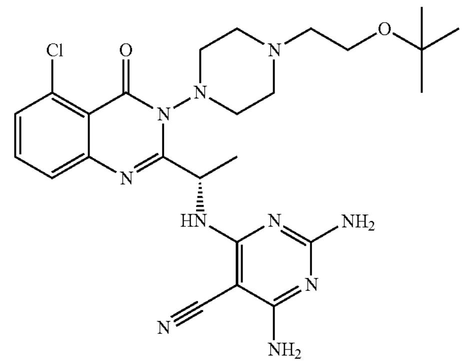 [SMILES: C[C@H](Nc1nc(N)nc(N)c1C#N)c1nc2cccc(Cl)c2c(=O)n1N1CCN(CCOC(C)(C)C)CC1] |
| 37 | 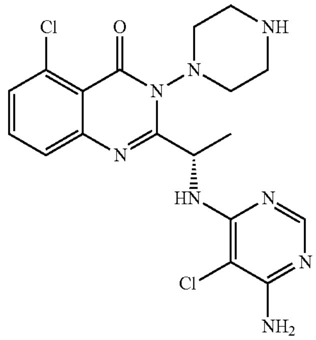 [SMILES: C[C@H](Nc1ncnc(N)c1Cl)c1nc2cccc(Cl)c2c(=O)n1N1CCNCC1] | 97 | 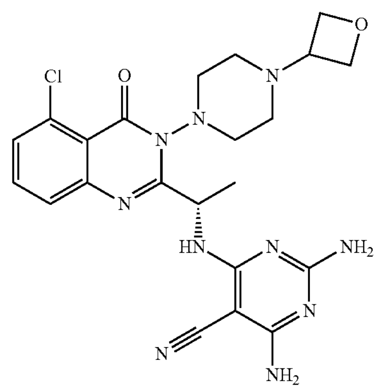 [SMILES: C[C@H](Nc1nc(N)nc(N)c1C#N)c1nc2cccc(Cl)c2c(=O)n1N1CCN(C2COC2)CC1] |
| 39 | 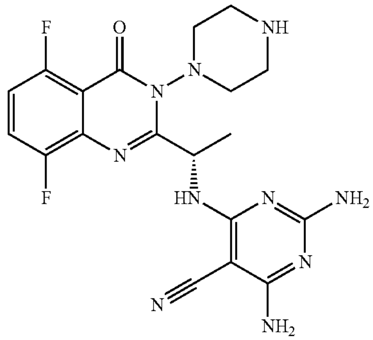 | 98 | 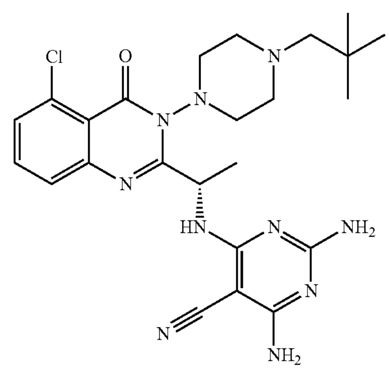 [SMILES: C[C@H](Nc1nc(N)nc(N)c1C#N)c1nc2cccc(Cl)c2c(=O)n1N1CCN(CC(C)(C)C)CC1] |
| 40 | 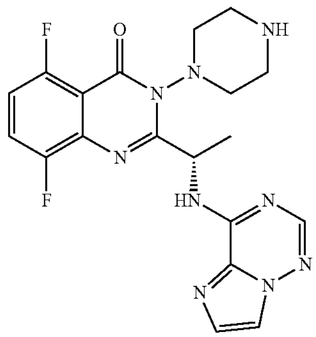 [SMILES: C[C@H](Nc1ncnn2ccnc12)c1nc2c(F)ccc(F)c2c(=O)n1N1CCNCC1] | 41 | 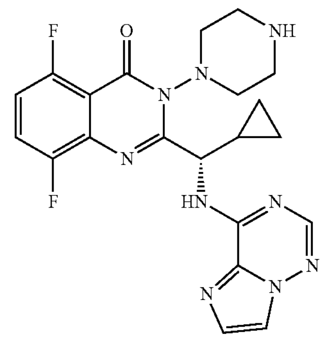 [SMILES: O=c1c2c(F)ccc(F)c2nc([C@@H](Nc2ncnn3ccnc23)C2CC2)n1N1CCNCC1] |

-continued

| Compound | Structure | Compound | Structure |
| --- | --- | --- | --- |
| 42 | 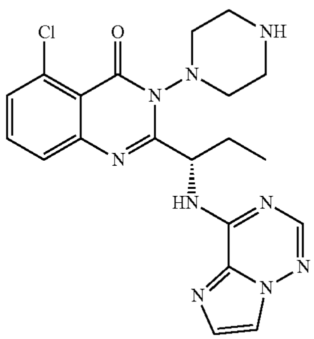 [SMILES: CC[C@H](Nc1ncnn2ccnc12)c1nc2cccc(Cl)c2c(=O)n1N1CCNCC1] | 102 | 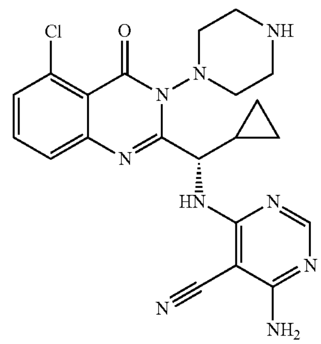 [SMILES: N#Cc1c(N)ncnc1N[C@H](c1nc2cccc(Cl)c2c(=O)n1N1CCNCC1)C1CC1] |
| 43 | 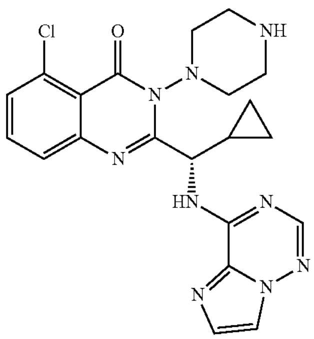 [SMILES: O=c1c2c(Cl)cccc2nc([C@@H](Nc2ncnn3ccnc23)C2CC2)n1N1CCNCC1] | 44 | 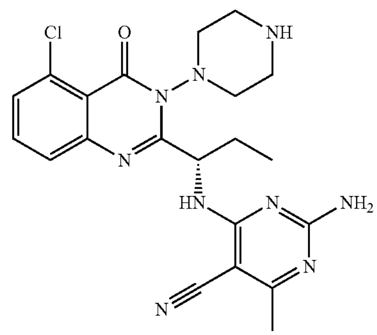 [SMILES: CC[C@H](Nc1nc(N)nc(C)c1C#N)c1nc2cccc(Cl)c2c(=O)n1N1CCNCC1] |
| 46 | 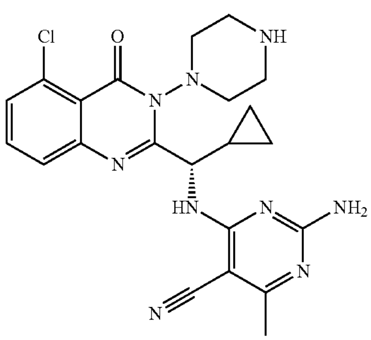 [SMILES: Cc1nc(N)nc(N[C@H](c2nc3cccc(Cl)c3c(=O)n2N2CCNCC2)C2CC2)c1C#N] | 47 | 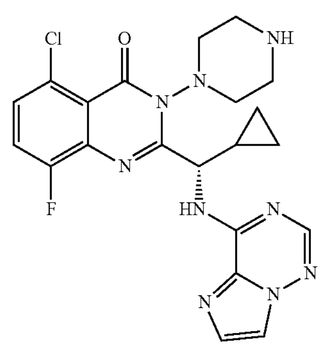 [SMILES: O=c1c2c(Cl)ccc(F)c2nc([C@@H](Nc2ncnn3ccnc23)C2CC2)n1N1CCNCC1] |
| 48 | 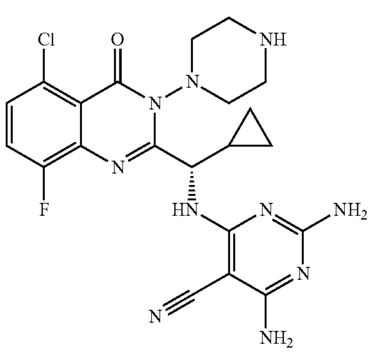 [SMILES: N#Cc1c(N)nc(N)nc1N[C@H](c1nc2c(F)ccc(Cl)c2c(=O)n1N1CCNCC1)C1CC1] | 107 | 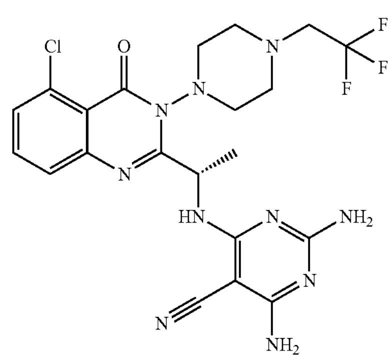 [SMILES: C[C@H](Nc1nc(N)nc(N)c1C#N)c1nc2cccc(Cl)c2c(=O)n1N1CCN(CC(F)(F)F)CC1] |

| Compound | Structure | Compound | Structure |
|---|---|---|---|
| 49 | 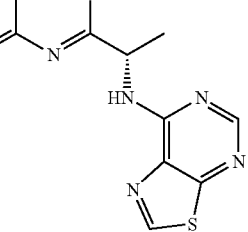 | 108 | 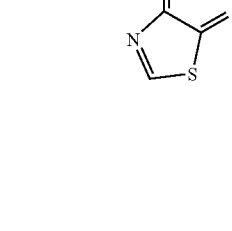 |
| 50 | 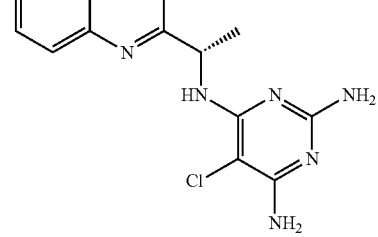 | 109 | 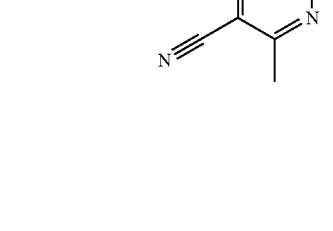 |
| 51 | 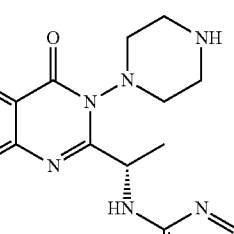 | 110 | 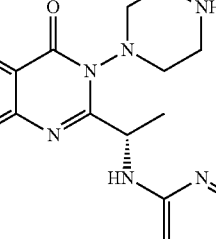 |
| 52 | 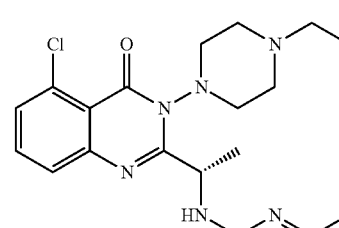 | 111 | 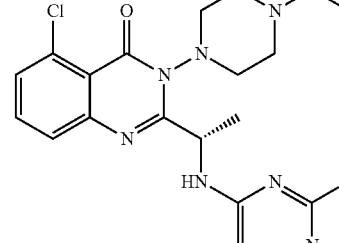 |

-continued

| Compound | Structure | Compound | Structure |
|---|---|---|---|
| 53 | 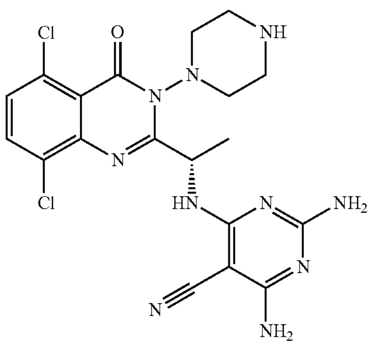 | 112 | 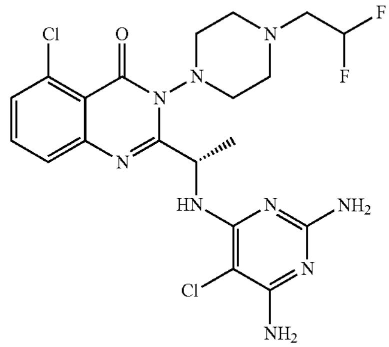 [SMILES: C[C@H](Nc1nc(N)nc(N)c1Cl)c1nc2cccc(Cl)c2c(=O)n1N1CCN(CC(F)F)CC1] |
| 54 | 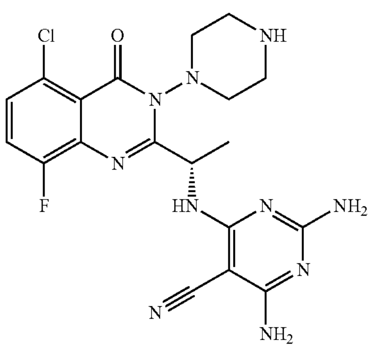 | 113 | 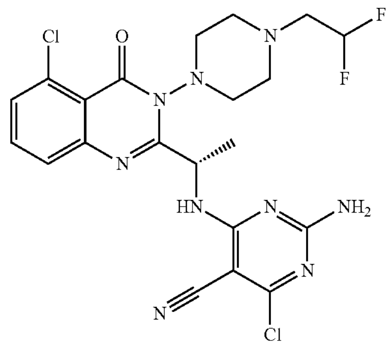 [SMILES: C[C@H](Nc1nc(N)nc(Cl)c1C#N)c1nc2cccc(Cl)c2c(=O)n1N1CCN(CC(F)F)CC1] |
| 55 | 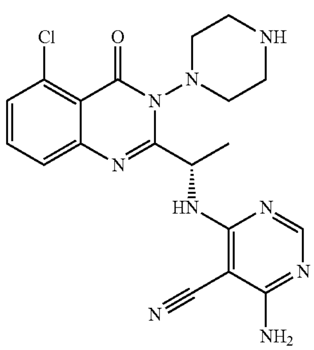 [SMILES: C[C@H](Nc1ncnc(N)c1C#N)c1nc2cccc(Cl)c2c(=O)n1N1CCNCC1] | 114 | 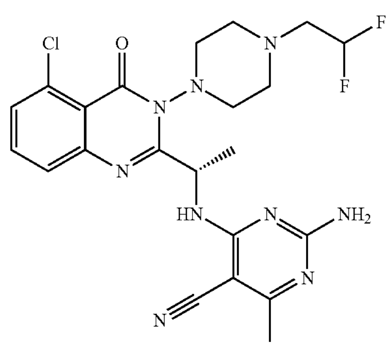 [SMILES: Cc1nc(N)nc(N[C@@H](C)c2nc3cccc(Cl)c3c(=O)n2N2CCN(CC(F)F)CC2)c1C#N] |
| 56 | 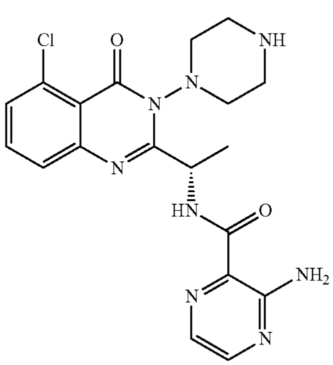 [SMILES: C[C@H](NC(=O)c1nccnc1N)c1nc2cccc(Cl)c2c(=O)n1N1CCNCC1] | 115 | 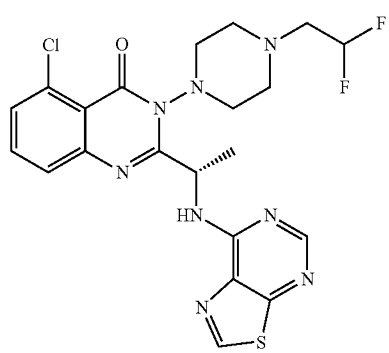 [SMILES: C[C@H](Nc1ncnc2scnc12)c1nc2cccc(Cl)c2c(=O)n1N1CCN(CC(F)F)CC1] |

-continued

| Compound | Structure | Compound | Structure |
|---|---|---|---|
| 57 | (5-chloro-quinazolinone with N-piperazinyl, 2-(1-aminoethyl) linked to 2,6-diamino-5-cyanopyrimidine) | 116 | (5-chloro-8-fluoro-quinazolinone with N-(4-benzylpiperazinyl), 2-(1-aminoethyl) linked to 2,6-diamino-5-cyanopyrimidine) |
| 59 | (5-chloro-quinazolinone with N-piperazinyl, 2-(1-aminoethyl) linked to 3-amino-5,6-dimethylpyrazine-2-carboxamide) | 117 | (5-chloro-8-fluoro-quinazolinone with N-(4-benzylpiperazinyl), 2-(1-aminoethyl) linked to 2,6-diamino-5-chloropyrimidine) | or a pharmaceutically acceptable salt thereof.

* * * * *